United States Patent
Ojima et al.

(10) Patent No.: US 11,739,047 B2
(45) Date of Patent: Aug. 29, 2023

(54) ALPHA-TRUXILLIC ACID DERIVATIVES AND PHARMACEUTICAL COMPOSITIONS THEREOF

(71) Applicant: The Research Foundation for The State University of New York, Albany, NY (US)

(72) Inventors: Iwao Ojima, Port Jefferson, NY (US); Dale Deutsch, Stony Brook, NY (US); Martin Kaczocha, Dix Hills, NY (US); Kongzhen Hu, Port Jefferson, NY (US); Simon Tong, Great Neck, NY (US); Matthew Elmes, Stony Brook, NY (US); Su Yan, Stony Brook, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 359 days.

(21) Appl. No.: 17/174,030

(22) Filed: Feb. 11, 2021

(65) Prior Publication Data

US 2021/0179535 A1 Jun. 17, 2021

Related U.S. Application Data

(62) Division of application No. 16/080,493, filed as application No. PCT/US2017/021711 on Mar. 10, 2017, now Pat. No. 10,968,163.

(60) Provisional application No. 62/307,262, filed on Mar. 11, 2016.

(51) Int. Cl.
| | |
|---|---|
| *C07C 69/753* | (2006.01) |
| *C07C 61/04* | (2006.01) |
| *C07C 69/757* | (2006.01) |
| *C07C 205/55* | (2006.01) |
| *C07D 249/06* | (2006.01) |
| *C07D 309/06* | (2006.01) |
| *C07C 233/25* | (2006.01) |
| *C07D 215/06* | (2006.01) |

(52) U.S. Cl.
CPC ............ *C07C 69/753* (2013.01); *C07C 61/04* (2013.01); *C07C 69/757* (2013.01); *C07C 205/55* (2013.01); *C07C 233/25* (2013.01); *C07D 215/06* (2013.01); *C07D 249/06* (2013.01); *C07D 309/06* (2013.01); C07C 2601/04 (2017.05); C07C 2601/14 (2017.05); C07C 2601/16 (2017.05); C07C 2602/10 (2017.05); C07C 2603/18 (2017.05)

(58) Field of Classification Search
CPC .............................. C07C 61/04; C07C 69/753
See application file for complete search history.

(56) References Cited

U.S. PATENT DOCUMENTS

| | | | |
|---|---|---|---|
| 2009/0163545 A1 | 6/2009 | Goldfarb | |
| 2019/0062261 A1 | 2/2019 | Ojima et al. | |

FOREIGN PATENT DOCUMENTS

| | | |
|---|---|---|
| CN | 101838239 A | 9/2010 |
| EP | 1118324 A1 | 7/2013 |
| ES | 2189602 A1 | 7/2003 |
| WO | WO 2003/043624 A1 | 5/2003 |
| WO | WO 2014/015276 A1 | 1/2014 |

OTHER PUBLICATIONS

Apr. 12, 2016 Office Action issued in connection with the U.S. Appl. No. 14/413,621.
Apr. 25, 2019 Office Action issued in connection with U.S. Appl. No. 16/080,493.
Arendaruk, A. P. and Skoldinov, A. P. (1960). Cyclobutanedicarboxylic acids. III. Basic esters of α-truxillic acid. Zhurnal Obshchei Khimii, 30, 2743-2745 (CAS Registry No. 857215-35-1, 860416-41-7 only).
Arendaruk, A. P. et al. (1967). Studies on cyclobutanedicarboxylic acids v. synthesis of bisquaternary salts of alkylamine esters and amides of the stereoisomeric truxillic acids. Institute of Pharmacology and Chemotherapy, Academy of Medical Sciences of the USSR, Moscow, 8, 445-448.
Arendaruk, A. P. et al. (1986) Chemical Abstract Service, CAPLUS No. 1986:625826.
Berger, W. T. et al. (2012). Targeting fatty acid binding protein (FABP) anandamide transporters—A novel strategy for development of anti-inflammatory and anti-nociceptive drugs. PLOS ONE, 7(2), 1-12.
Chi, Y. et al. (2005). Anti-inflammatory activities of α-truxillic acid derivatives and their monomer components. Biological and Pharmaceutical Bulletin, 28(9), 1776-1778.
Chi, Y. et al. (2006). Antinociceptive activities of α-truxillic acid and ß-truxinic acid derivatives. Biological and Pharmaceutical Bulletin, 29(3), 580-584.
Examination Report No. 1, dated Jun. 22, 2020 in connection with Australian Patent Application No. 2017230790.
Feb. 17, 2016 European Search Report issued in connection with the European Patent Application No. 13820647.9.
First Examination Report, dated Jun. 5, 2020 in connection with Indian Patent Application No. 201817038406.

(Continued)

*Primary Examiner* — Theodore R. Howell
(74) *Attorney, Agent, or Firm* — Gary J. Gershik

(57) ABSTRACT

The present invention provides a compound, and method of inhibiting the activity of a Fatty Acid Binding Protein (FABP) comprising contacting the FABP with a compound, said compound having the structure: Formula (I)

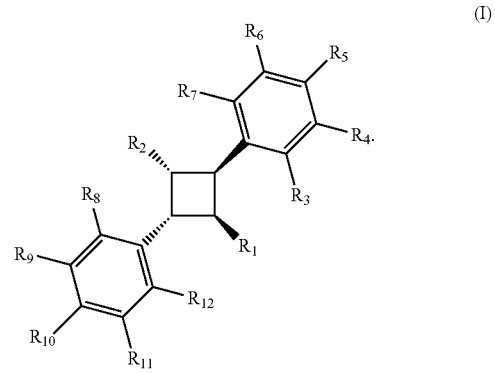

20 Claims, 2 Drawing Sheets

(56) References Cited

OTHER PUBLICATIONS

Ford, C. W. and Hartley, R. D. (1990). Cyclodimers of p-coumaric and ferulic acids in the cell walls of tropical grasses. Journal of the Science of Food and Agriculture, 50(1), 29-43.
Gutekunst, W. et al. (2011) Total Synthesis and Structural Revision of the Poperaborenines via Sequential Cyclobutane C-H Arylation. Journal of the American Chemical Society, vol. 133, No. 47, pp. 19076-19079.
Huong, D. et al. (2008) Two New Bis-styryl Compounds from *Miliusa balansae*. Z. naturforsch, vol. 63b, pp. 335-338.
Ichikawa, M. et al. (2004) . Total synthesis of (-)-Incarvilline, (+)-Incarvine C, and (-)-Incarvillateine. Journal of the American Chemical Society, 126, 16553-16558.
International Search Report dated Jun. 29, 2017 in connection with PCT International Application No. PCT/US2017/021711.
Jan. 29, 2019 Office Action issued in connection with the European Patent Application No. 13820647.9.
Jul. 15, 2016 Office Action issued in connection with the U.S. Appl. No. 14/413,621.
Jul. 3, 2019 Office Action issued in connection with U.S. Appl. No. 16/080,493.
Jun. 25, 2019 Response to Apr. 25, 2019 Office Action issued in connection with U.S. Appl. No. 16/080,493.
Jun. 28, 2018 Office Action issued in connection with the European Patent Application No. 13820647.9.
Jun. 8, 2020 Non-Final Office Action issued in connection with U.S. Appl. No. 16/080,493.
Krauze-Baranowska, M. (2002). Truxillic and truxinic acids—Occurrence in plant kingdom. Acta Poloniae Pharmaceutica—Drug Research, 59(5), 403-410.
Mar. 23, 2017 Office Action issued in connection with the European Patent Application No. 13820647.9.
Mar. 23, 2020 Amendment in response dated Oct. 23, 2019 Final Office Action issued in connection with U.S. Appl. No. 16/080,493.
Nakamura, M. et al. (1999). Strong antinociceptive effect of incarvillateine, a novel monoterpene alkaloid from Incarvillea sinensis. Journal of Natural Products, 62, 1293-1294.
Notice of Allowance, including Notice of Allowability, dated Oct. 29, 2020 in connection with U.S. Appl. No. 16/080,493.
Notification Concerning Transmittal of Copy of International Preliminary Report on Patentability (Chapter I of the Patent Cooperation Treaty), including an International Preliminary Report on Patentability and Written Opinion of the International Searching Authority, dated Jan. 29, 2015 by The International Bureau of WIPO in connection with PCT International Application No. PCT/US2013/051337, filed Jul. 19, 2013.
Notification of Transmittal of the International Search Report and the Written Opinion of the International Searching Authority, or the Declaration, including an International Search Report and Written Opinion of the International Searching Authority, dated Dec. 26, 2013 in connection with PCT International Application No. PCT/US2013/051337, filed Jul. 19, 2013.
Nov. 13, 2017 Office Action issued in connection with the European Patent Application No. 13820647.9.
Nov. 6, 2015 Office Action issued in connection with the U.S. Appl. No. 14/413,621.
Oct. 23, 2019 Final Office Action issued in connection with U.S. Appl. No. 16/080,493.
Oct. 3, 2019 Amendment in Response dated Jul. 3, 2019 Office Action issued in connection with U.S. Appl. No. 16/080,493.
Oct. 8, 2020 Communication in response dated Jun. 8, 2020 Non-Final Office Action issued in connection with U.S. Appl. No. 16/080,493.
Official Action dated May 28, 2020 in connection with Eurasian Patent Application No. 201892045, including English language translation.
Pera, N. H. et al. (1972). Truxillic acid amides. Chimica Therapeutica, 7(1), 42-44 (CAS Registry No. 37518-16-4, 37518-17-5 only).
Response to Communication pursuant to Rules 70(2) and 70a(2) EPC, filed Jun. 1, 2020 in connection with European Patent Application No. 17764162.8.
Rupp, M. et al. (2010). From machine learning to natural product derivatives that selectively activate transcription factor PPARγ. ChemMedChem, 5, 191-194.
Schenck, F. (1930). Resolution of some ester acids of the γ-truxillic acids into the optical components. Berichte der Deutschen Chemischen Gesellschaft [Abteilung] B: Abhandlungen, 63B, 2706-2712 (CAS Registry No. 321863-32-5 only).
Steri, R. et al. (2010). Truxillic acid derivatives act as peroxisome proliferator-activated receptor γ activators. Bioorganic & Medicinal Chemistry Letters, 20(9), 2920-2923.
Supplementary European Search Report, issued by the European Patent Office dated Sep. 20, 2019 in connection with European Patent Application No. EP 17784162.
Takeda, R. et al. "The First Isolation of Lignans, Megacerotonic Acid, and Anthocerotonic Acid, from Non-Vascular Plants, Anthocerotae (Hornworts)," Tetrahedron Letters, 1990, vol. 23, No. 29, pp. 4159-4162.
Takeda, R. et al. (1990). Phenolic compounds from Anthocerotae. Proceedings of the Phytochemical Society of Europe, 29, 201-207 (CAS Registry No. 130396-77-9).
Written Opinion (form PCT/ISA/237) dated Jun. 29, 2017 in connection with PCT International Application No. PCT/US2017/021711.
Yang, H. et al. (2011). Novel photolabile diblock copolymers bearing truxillic acid derivative junctions. Macromolecules, 44, 159-165.

AEA (Anandamide) FAAH (fatty acid amide hydrolase)
FABP (fatty acid binding protein), CB (cannabinoid receptor)

ALPHA-TRUXILLIC ACID DERIVATIVES AND PHARMACEUTICAL COMPOSITIONS THEREOF

CROSS-REFERENCE TO RELATED APPLICATIONS

This application is a divisional of U.S. application Ser. No. 16/080,493, filed Aug. 28, 2018, now allowed, a § 371 national stage of PCT International Application No. PCT/US2017/021711, filed Mar. 10, 2017, claiming the benefit of U.S. Provisional Application No. 62/307,262, filed Mar. 11, 2016, the entire contents of each of which are hereby incorporated by reference herein.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

GOVERNMENT SUPPORT

This invention was made with government support under grant number DA035923 awarded by the National Institutes of Health. The government has certain rights in the invention.

BACKGROUND OF THE INVENTION

Lipids, owing to their water insolubility, require a variety of fatty acid binding protein (FABP) chaperones or transporters to carry them throughout cells (Furuhashi, M et al. 2008). The FABPs are part of the pathway of anandamide inactivation by the fatty acid amide hydrolase (FAAH), an enzyme localized inside the cell on the endoplasmic reticulum. The endocannabinoid anandamide (arachidonoyl ethanolamide or AEA) is an uncharged neuromodulatory lipid that is inactivated through its cellular uptake by FABPs and subsequent hydrolysis by FAAH into ethanolamine and arachidonic acid.
Exhibit B Cannabinoids such as anandamide have broad effects on the central nervous system (CNS) and influence, for example, movement, memory, nociception, endocrine regulation, thermoregulation, sensory perception, cognitive functions, and mood. Similarly, genetic and pharmacological studies have revealed a broad role for endocannabinoid signaling in a variety of physiological processes, including neuromodulator release, motor learning, synaptic plasticity, appetite, and pain sensation. Anandamide produces most of its pharmacological effects by binding and activating the cannabinoid receptor (CB-1 and CB-2) within the CNS. The increase in extracellular anandamide caused by the inhibition of FABPs triggers activation of the cannabinoid receptor type 1 (CB-1) pathway leading to the relief of neurogenic and inflammatory pain.

Recently, it was shown that anandamide (an endocannabinoid) uses FABPs such as FABP5 (E-FABP) and FABP7 (B-FABP) as intracellular transporters (Kaczocha, M. et al. 2009). FABPs are drug targets similar to FAAH since inhibitors of each decrease hydrolysis of anandamide and its uptake into cells, raising the levels of extracellular anandamide (FIG. 1) (Howlett, A. C. et al. 2011; Kaczocha, M. et al. 2012; Ahn, K. et al. 2009). Few specific FABP inhibitors have been described. There are those that were specifically designed for FABP4, such as BMS309403, which are important for the protective effects that they exert in metabolic syndrome and atherosclerosis (Barf, T. et al. 2009; Sulsky, R. et al. 2007). BMS309403 also binds other FABPs, such as FABP5 and FABP7, that carry anandamide, as do other inhibitors originally designed to inhibit a putative anandamide transmembrane transporter (Kaczocha, M. et al. 2012).

SUMMARY OF THE INVENTION

The present invention provides a compound of having the structure:

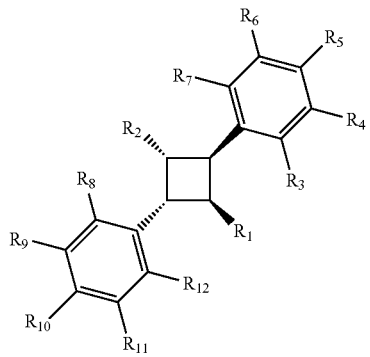

wherein
one of $R_1$ or $R_2$ is —C(=O)OH and the other of $R_1$ or $R_2$ is —C(=O)$OR_{13}$ or —C(=O)O-alkyl-$R_{14}$,
wherein
$R_{13}$ is cycloalkyl, aryl or heteroaryl, and
$R_{14}$ is $CF_3$, cycloalkyl, cycloheteroalkyl, aryl or heteroaryl; and
$R_3$, $R_4$, $R_5$, $R_6$, $R_7$, $R_8$, $R_9$, $R_{10}$, $R_{11}$ and $R_{12}$ are each independently, H—$OR_{15}$ or halogen
wherein $R_{15}$ is H, $C_{1-10}$ alkyl, $C_{2-10}$ alkenyl, $C_{2-10}$ alkynyl, aryl, or heteroaryl,
wherein when one of $R_1$ or $R_2$ is —C(=O)OH and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)$OR_{13}$ where $R_{13}$ is 1-naphthalene or 2-naphthalene or —C(=O)O-alkyl-$R_{14}$ where the alkyl is a branched $C_2$ alkyl and the $R_{14}$ is phenyl,
or an enantiomer or racemate thereof;
or a pharmaceutically acceptable salt thereof.

BRIEF DESCRIPTION OF THE FIGURES

FIG. 2: Bar graphs demonstrating latency (sec) of baseline, Freund's complete adjuvant (CFA), vehicle, Compound A, Compound B, Compound C, and Compound D; and compound (µg/mL) of Compound B and Compound A. Compound A refers to Compound 3, Compound B is a methyl ester of Compound 3, Compound C refers to Compound 3a, Compound D refers to Compound 4a.

DETAILED DESCRIPTION OF THE INVENTION

Figure 1:
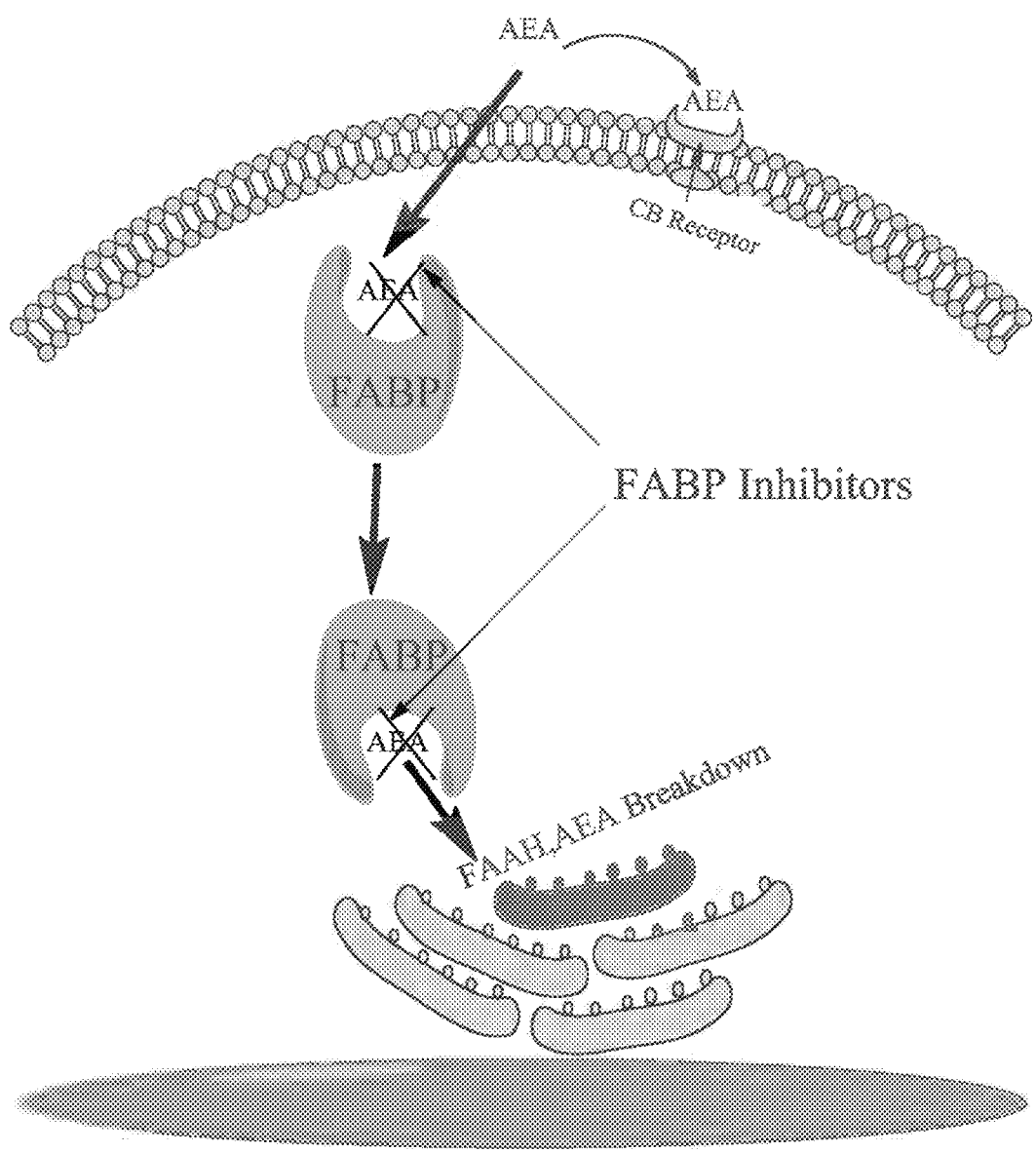
FIG. 1: Scheme demonstrating anandamide inactivation and FABP drug target. Anandamide crosses the membrane by diffusion but requires FABPs for transport through the cytoplasm to the endoplasmic reticulum for breakdown by FAAH. FABP inhibitors prevent AEA from being delivered to FAAH for breakdown resulting in increased AEA levels at the receptor.
Figure 2:
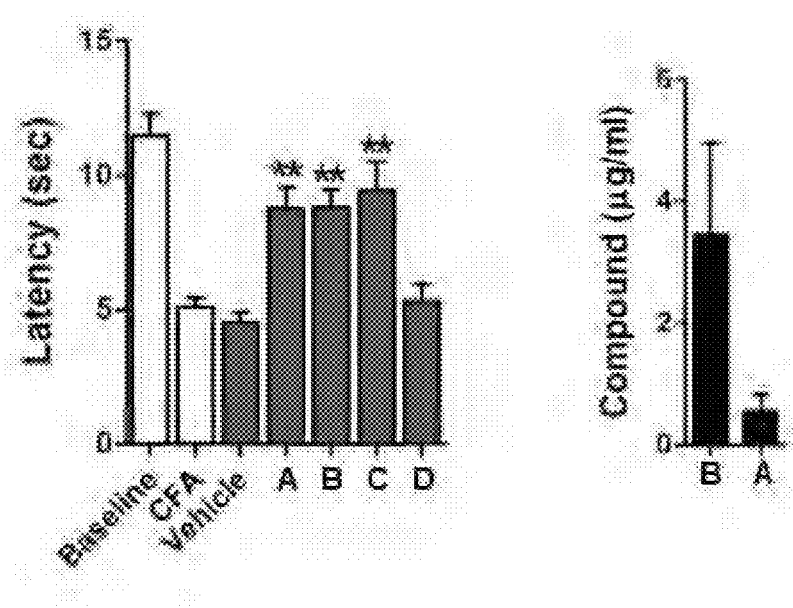

The present invention provides a compound of having the structure:

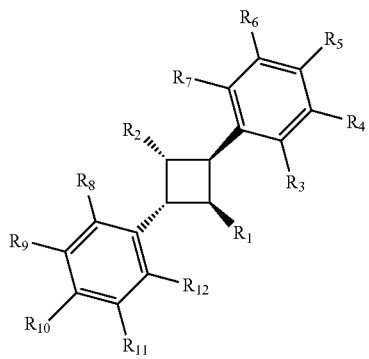

wherein
one of $R_1$ or $R_2$ is —C(=O)OH and the other of $R_1$ or $R_2$ is —C(=O)O$R_{13}$ or —C(=O) O-alkyl-$R_{14}$,
wherein
$R_{13}$ is cycloalkyl, aryl or heteroaryl, and
$R_{14}$ is $CF_3$, cycloalkyl, cycloheteroalkyl, aryl or heteroaryl; and
$R_3$, $R_4$, $R_5$, $R_6$, $R_7$, $R_8$, $R_9$, $R_{10}$, $R_{11}$ and $R_{12}$ are each independently, H—O$R_{15}$ or halogen
wherein $R_{15}$ is H, $C_{1-10}$ alkyl, $C_{2-10}$ alkenyl, $C_{2-10}$ alkynyl, aryl, or heteroaryl,
wherein when one of $R_1$ or $R_2$ is —C(=O)OH and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)O$R_{13}$ where $R_{13}$ is 1-naphthalene or 2-naphthalene or —C(=O)O-alkyl-$R_{14}$ where the alkyl is a branched $C_2$ alkyl and the $R_{14}$ is phenyl,
or an enantiomer or racemate thereof;
or a pharmaceutically acceptable salt or ester thereof.

The present invention provides a compound of having the structure:

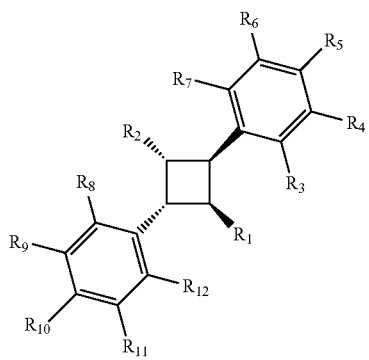

wherein
one of $R_1$ or $R_2$ is —C(=O)OH and the other of $R_1$ or $R_2$ is —C(=O)O$R_{13}$ or —C(=O) O-alkyl-$R_{14}$,
wherein
$R_{13}$ is cycloalkyl, aryl or heteroaryl, and
$R_{14}$ is $CF_3$, cycloalkyl, aryl or heteroaryl; and
$R_3$, $R_4$, $R_5$, $R_6$, $R_7$, $R_8$, $R_9$, $R_{10}$, $R_{11}$ and $R_{12}$ are each independently, H—O$R_{15}$ or halogen
wherein $R_{15}$ is H, $C_{1-10}$ alkyl, $C_{2-10}$ alkenyl, $C_{2-10}$ alkynyl, aryl, or heteroaryl,
wherein when one of $R_1$ or $R_2$ is —C(=O)OH and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)O$R_{13}$ where $R_{13}$ is 1-naphthalene or 2-naphthalene or —C(=O)O-alkyl-$R_{14}$ where the alkyl is a branched $C_2$ alkyl and the $R_{14}$ is phenyl,
or an enantiomer or racemate thereof;
or a pharmaceutically acceptable salt thereof.

In some embodiments, the compound wherein when one of $R_1$ or $R_2$ is —C(=O)OH and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)O$R_{13}$ where $R_{13}$ is tolyl, 1-naphthalene or 2-naphthalene or —C(=O)O-alkyl-$R_{14}$ where the alkyl is a branched $C_2$ alkyl and the $R_{14}$ is phenyl.

In some embodiments, the compound wherein when one of $R_1$ or $R_2$ is —C(=O)OH and the other of $R_1$ or $R_2$ is —C(=O)O$R_{13}$ where $R_{13}$ is 1-naphthalene or 2-naphthalene, then one of $R_3$, $R_4$, $R_5$, $R_6$, $R_7$, $R_8$, $R_9$, $R_{10}$, Ru and $R_{12}$ is other than —H.

In some embodiments, the compound wherein when one of $R_1$ or $R_2$ is —C(=O)OH and the other of $R_1$ or $R_2$ is —C(=O)O$R_{13}$ where $R_{13}$ is 1-naphthalene or 2-naphthalene, then two of $R_3$, $R_4$, $R_5$, $R_6$, $R_7$, $R_8$, $R_9$, $R_1$, $R_{11}$ and $R_{12}$ is other than —H.

In some embodiments, the compound wherein when one of $R_1$ or $R_2$ is —C(=O)OH and the other of $R_1$ or $R_2$ is —C(=O)O$R_{13}$ where $R_{13}$ is 1-naphthalene or 2-naphthalene, then four of $R_3$, $R_4$, $R_5$, $R_6$, $R_7$, $R_8$, $R_9$, $R_{10}$, $R_{11}$ and $R_{12}$ is other than —H.

In some embodiments, the compound wherein
one of $R_1$ or $R_2$ is —C(=O) $R_{13}$,
wherein $R_{13}$ is cycloalkyl, aryl or heteroaryl; and
the other of $R_1$ or $R_2$ is —C(=O)OH.

In some embodiments, the compound wherein
one of $R_1$ or $R_2$ is —C(=O)O-alkyl-$R_{14}$,
wherein $R_{14}$ is $CF_3$, cycloalkyl, aryl or heteroaryl; and
the other of $R_1$ or $R_2$ is —C(=O)OH.

In some embodiments, the compound wherein
one of $R_1$ or $R_2$ is —C(=O)O—($C_{1-6}$ alkyl) —$R_{14}$,
wherein $R_{14}$ is $CF_3$, cycloalkyl, aryl or heteroaryl; and
the other of $R_1$ or $R_2$ is —C(=O)OH.

In some embodiments, the compound wherein
one of $R_1$ or $R_2$ is —C(=O)O—$CH_3$—$R_{14}$,
wherein $R_{14}$ is $CF_3$, cycloalkyl, aryl or heteroaryl; and
the other of $R_1$ or $R_2$ is —C(=O)OH.

In some embodiments, the compound wherein the aryl is a substituted aryl.

In some embodiments, the compound wherein the aryl is substituted with a halogen, —OH, heteroaryl, $C_2$-$C_6$ alkynyl or —O(alkyl).

In some embodiments, the compound wherein the aryl is substituted with a amide, aryl or hydroxyaryl.

In some embodiments, the compound wherein the aryl is substituted with a F, Cl, Br, —OH, triazolyl, $C_2$ alkylnyl or —O$CH_3$.

In some embodiments, the compound wherein the aryl is substituted with a F, Cl, Br, —OH, I, —NHC(O)$CH_3$, triazolyl, $C_2$ alkylnyl, phenyl, o-hydroxyphenyl or —O$CH_3$.

In some embodiments, the compound wherein the heteroaryl is a substituted heteroaryl.

In some embodiments, the compound wherein the heteroaryl is substituted with a halogen, —OH, heteroaryl, $C_2$-$C_6$ alkynyl or —O(alkyl).

In some embodiments, the compound wherein the heteroaryl is substituted with an amide, aryl or hydroxyaryl.

In some embodiments, the compound wherein the heteroaryl is substituted with an F, Cl, Br, —OH, triazolyl, $C_2$ alkylnyl or —OCH$_3$.

In some embodiments, the compound wherein the heteroaryl is substituted with a F, Cl, Br, —OH, I, —NHC(O)CH$_3$, triazolyl, $C_2$ alkylnyl, phenyl, O-hydroxyphenyl or —OCH$_3$.

In some embodiments, the compound wherein the cycloalkyl is a substituted cycloalkyl.

In some embodiments, the compound wherein the cycloalkyl is substituted with an phenyl or a fused benzo group.

In some embodiments, the compound wherein the cycloalkyl is:

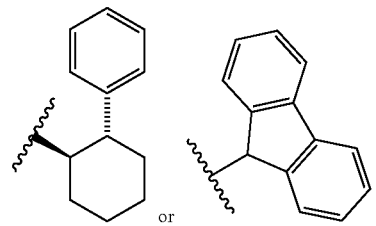

In some embodiments, the compound wherein the cycloalkyl is:

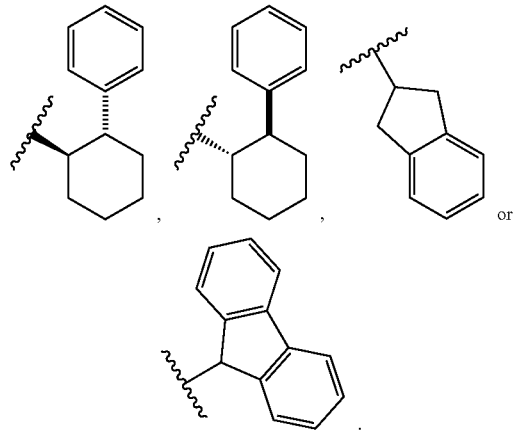

In some embodiments, the compound wherein the cycloalkyl is:

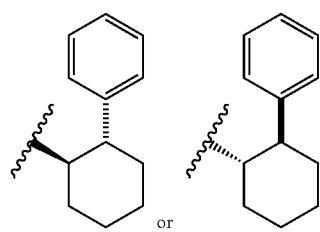

In some embodiments, the compound wherein the cycloalkyl is:

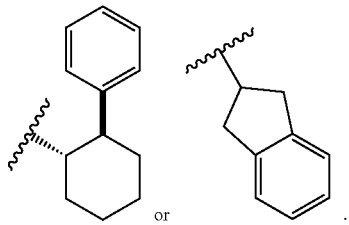

In some embodiments, the compound wherein one of $R_1$ or $R_2$ is

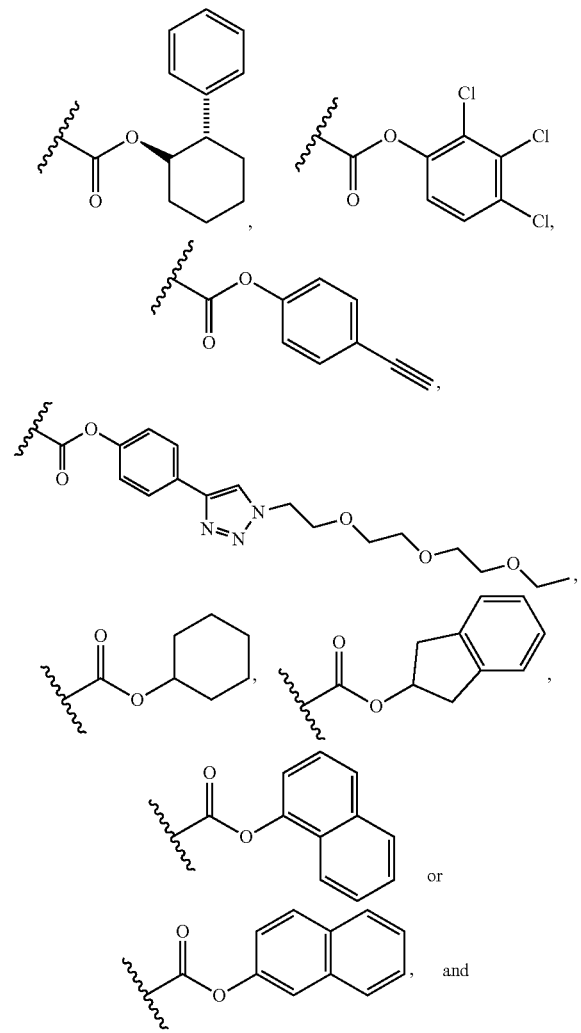

the other of $R_1$ or $R_2$ is —C(=O) OH.

In some embodiments, the compound wherein one of $R_1$ or $R_2$ is

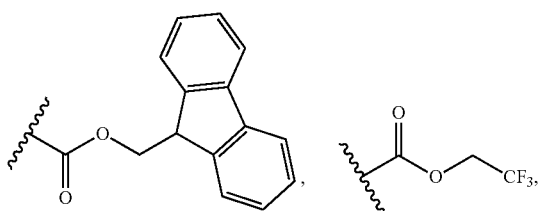

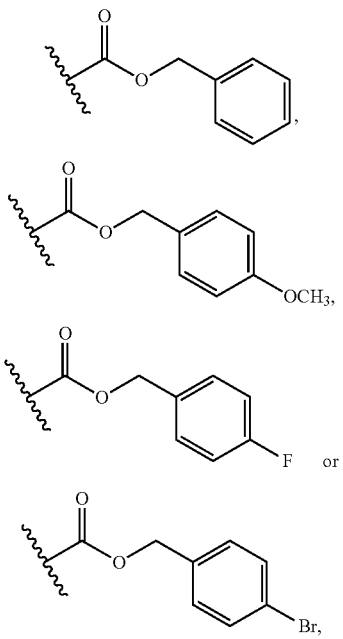

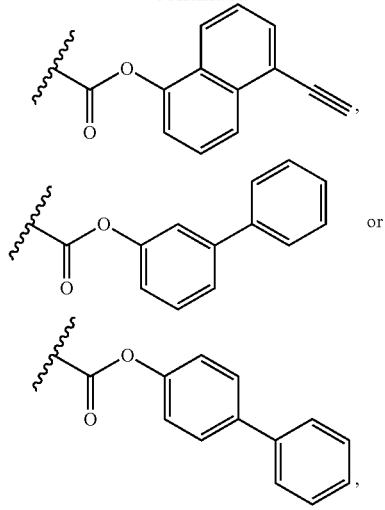

and
the other of $R_1$ or $R_2$ is —C(=O)OH.

In some embodiments, the compound wherein one of $R_1$ or $R_2$ is

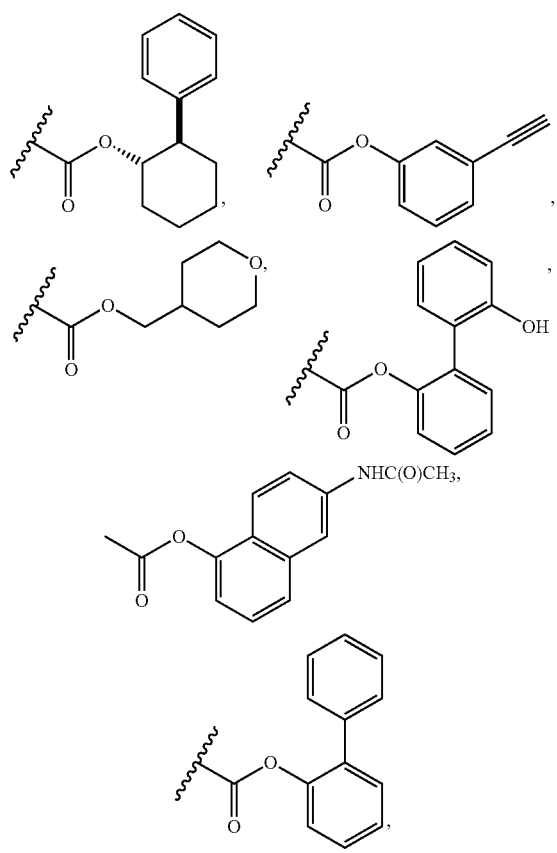

and
the other of $R_1$ or $R_2$ is —C(=O)OH.

In some embodiments, the compound wherein $R_3$, $R_4$, $R_5$, $R_6$, $R_7$, $R_8$, $R_9$, $R_{10}$, $R_{11}$ and $R_{12}$ are each independently, —H, halogen or —OR$_{15}$, wherein $R_{15}$ is —H or $C_{1-10}$ alkyl.

In some embodiments, the compound wherein $R_3$, $R_4$, $R_5$, $R_6$, $R_7$, $R_8$, $R_9$, $R_{10}$, $R_{11}$ and $R_{12}$ are each independently, —H, F, $C_1$, Br or —OR$_{15}$, wherein $R_{15}$ is —H or $C_{1-6}$ alkyl.

In some embodiments, the compound wherein $R_3$, $R_4$, $R_5$, $R_6$, $R_7$, $R_8$, $R_9$, $R_{10}$, $R_{11}$ and $R_{12}$ are each independently, —H, $C_1$ or —OR$_{15}$, wherein $R_{15}$ is —H or CH$_3$.

In some embodiments, the compound wherein $R_3$, $R_4$, $R_5$, $R_6$, $R_7$, $R_8$, $R_9$, $R_{10}$, $R_{11}$ and $R_{12}$ are each independently, —H or —NO$_2$.

In some embodiments, the compound wherein one of $R_3$, $R_4$, $R_5$, $R_6$, $R_7$, $R_8$, $R_9$, $R_{10}$, $R_{11}$ and $R_1$ is other than —H.

In some embodiments, the compound wherein two of $R_3$, $R_4$, $R_5$, $R_6$, $R_7$, $R_8$, $R_9$, $R_{10}$, $R_{11}$ and $R_{12}$ are other than —H.

In some embodiments, the compound wherein four of $R_3$, $R_4$, $R_5$, $R_6$, $R_7$, $R_8$, $R_9$, $R_{10}$, $R_{11}$ and $R_{12}$ are other than —H.

In some embodiments, the compound wherein $R_3$, $R_4$, $R_6$, $R_7$, $R_8$, $R_9$, $R_{10}$ and $R_{12}$ are each —H; and $R_5$ and $R_{10}$ are each halogen or —OR$_{15}$,
  wherein $R_{15}$ is —H, $C_{1-10}$ alkyl, $C_{2-10}$ alkenyl, $C_{2-10}$ alkynyl, aryl, or heteroaryl.

In some embodiments, the compound wherein $R_3$, $R_4$, $R_6$, $R_7$, $R_8$, $R_9$, $R_{11}$ and $R_{12}$ are each —H; and $R_5$ and $R_{10}$ are each —OR$_{15}$,
  wherein $R_{15}$ is —H or $C_{1-10}$ alkyl.

In some embodiments, the compound wherein $R_3$, $R_4$, $R_6$, $R_7$, $R_8$, $R_9$, $R_{11}$ and $R_{12}$ are each —H; and $R_5$ and $R_{10}$ are each —OR$_{15}$,
  wherein $R_{15}$ is —H or $C_{1-6}$ alkyl.

In some embodiments, the compound wherein $R_3$, $R_4$, $R_6$, $R_7$, $R_8$, $R_9$, $R_{11}$ and $R_{12}$ are each —H; and $R_5$ and $R_{10}$ are each —OR$_{15}$,
  wherein $R_{15}$ is —H or CH$_3$.

In some embodiments, the compound wherein $R_4$, $R_5$, $R_6$, $R_9$, $R_{10}$ and $R_{11}$ are each —H; $R_3$ and $R_{12}$ are each —H, halogen or —OR$_{15}$; and $R_7$ and $R_8$ are each halogen or —OR$_{15}$,
  wherein $R_{15}$ is —H, $C_{1-10}$ alkyl, $C_{2-10}$ alkenyl, $C_{2-10}$ alkynyl, aryl, or heteroaryl.

In some embodiments, the compound wherein $R_4$, $R_5$, $R_6$, $R_9$, $R_{10}$ and $R_{11}$ are each —H; $R_3$ and $R_{12}$ are each —H, halogen or —OR$_{15}$; and $R_7$ and $R_8$ are each halogen or —OR$_{15}$,
  wherein $R_{15}$ is —H or $C_{1-10}$ alkyl.

In some embodiments, the compound wherein $R_3$, $R_4$, $R_5$, $R_6$, $R_9$, $R_{10}$, $R_{11}$ and $R_{12}$ are each —H; and $R_7$ and $R_8$ are each F, Br, $C_1$ or —$OR_{11}$, wherein $R_{15}$ is —H or $C_{1-6}$ alkyl.

In some embodiments, the compound wherein $R_3$, $R_4$, $R_6$, $R_7$, $R_8$, $R_9$, $R_{11}$ and $R_{12}$ are each —H; and $R_5$ and $R_{10}$ are each $C_1$ or —$OR_{15}$, wherein $R_{15}$ is —H or $CH_3$.

In some embodiments, the compound wherein $R_3$, $R_4$, $R_7$, $R_8$, $R_9$ and $R_{12}$ are each —H; and $R_5$, $R_6$, $R_{10}$ and $R_{11}$ are each halogen or —$OR_{15}$, wherein $R_{15}$ is —H, $C_{1-10}$ alkyl, $C_{2-10}$ alkenyl, $C_{2-10}$ alkynyl, aryl, or heteroaryl.

In some embodiments, the compound wherein $R_3$, $R_4$, $R_7$, $R_8$, $R_9$ and $R_{12}$ are each —H; and $R_5$, $R_6$, $R_{10}$ and $R_{11}$ are each —$OR_{15}$, wherein $R_1$ is —H or $C_{1-10}$ alkyl.

In some embodiments, the compound wherein $R_3$, $R_4$, $R_7$, $R_8$, $R_9$ and $R_{12}$ are each —H; and $R_5$, $R_6$, $R_{10}$ and $R_{11}$ are each —$OR_{15}$, wherein $R_{15}$ is —H or $C_{1-6}$ alkyl.

In some embodiments, the compound wherein $R_3$, $R_4$, $R_7$, $R_8$, $R_9$ and $R_{12}$ are each —H; and $R_5$, $R_6$, $R_{10}$ and $R_{11}$ are each —$OR_{15}$, wherein $R_{15}$ is —H or $CH_3$.

In some embodiments, the compound wherein $R_3$, $R_4$, $R_5$, $R_6$, $R_5$, $R_9$, $R_{10}$ and $R_{1a}$ are each —H; and $R_7$ and $R_{12}$ are each $NO_2$.

In some embodiments, the compound wherein one of $R_1$ or $R_2$ is —C(=O)OH and the other of $R_1$ or $R_2$ is —C(=O)$OR_{13}$ or —C(=O)O-alkyl-$R_{14}$, wherein $R_{13}$ is cycloalkyl or aryl, and $R_{14}$ is $CF_3$ or aryl; and $R_3$, $R_4$, $R_5$, $R_6$, $R_7$, $R_8$, $R_9$, $R_{10}$, $R_{11}$ and $R_{12}$ are each independently, H or —$OR_{15}$, wherein $R_{15}$ is H or $C_{1-10}$ alkyl, or an enantiomer or racemate thereof;

or a pharmaceutically acceptable salt thereof.

In some embodiments, the compound wherein one of $R_1$ or $R_2$ is —C(=O)OH and the other of $R_1$ or $R_2$ is —C(=O)$OR_{13}$ or —C(=O) O-alkyl-$R_{14}$, wherein $R_{13}$ is cycloalkyl or aryl, and $R_{14}$ is $CF_3$, cycloheteroalkyl or aryl; and $R_3$, $R_4$, $R_5$, $R_6$, $R_7$, $R_8$, $R_9$, $R_{10}$, $R_{11}$ and $R_{12}$ are each independently, H or —$OR_{15}$, wherein $R_{15}$ is H or $C_{1-10}$ alkyl, or an enantiomer or racemate thereof;

or a pharmaceutically acceptable salt thereof.

In some embodiments, the compound wherein $R_3$ is identical to $R_8$, $R_4$ is identical to $R_9$, $R_5$ is identical to $R_{10}$, $R_6$ is identical to $R_{11}$ and $R_7$ is identical to $R_{12}$.

In some embodiments, the compound wherein $R_3$, $R_7$ and $R_5$ are identical to $R_{12}$, $R_4$, $R_6$, and $R_9$ are identical to $R_{11}$, and $R_5$ is identical to $R_{10}$.

In some embodiments, the compound having the structure

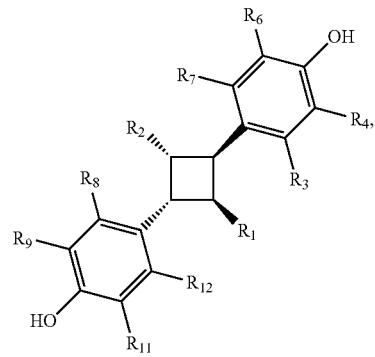

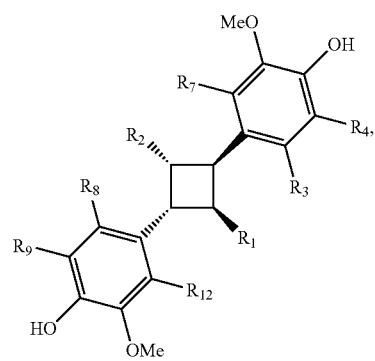

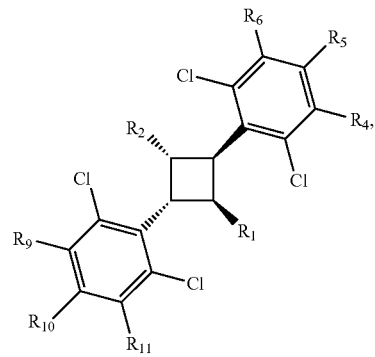

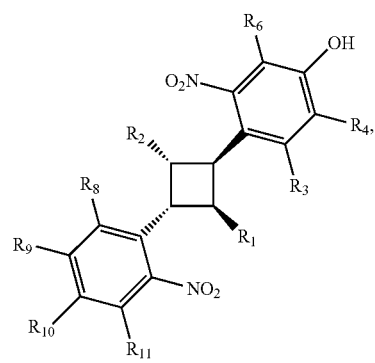

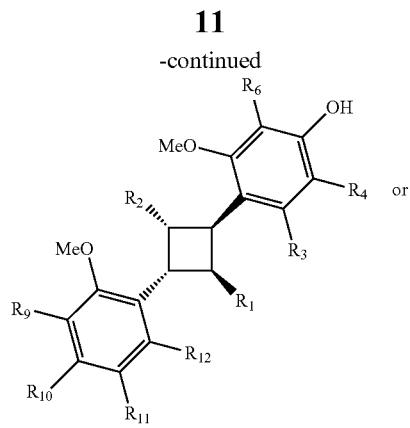
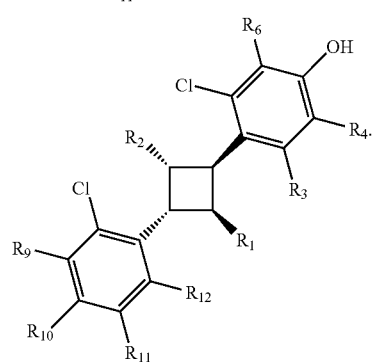
In some embodiments, the compound having the structure:
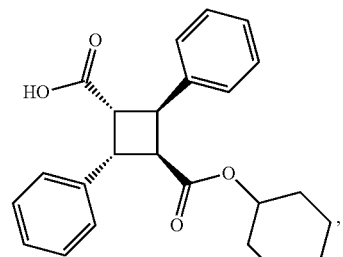
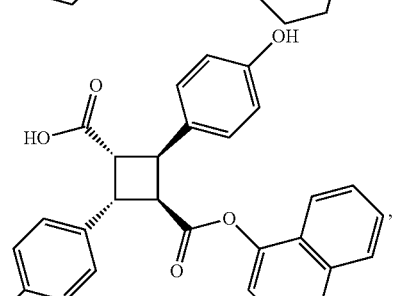
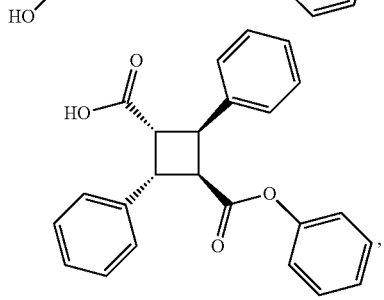
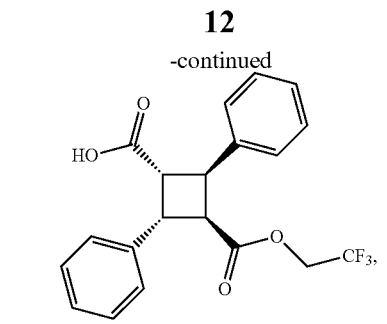
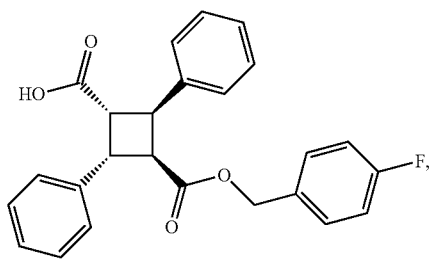
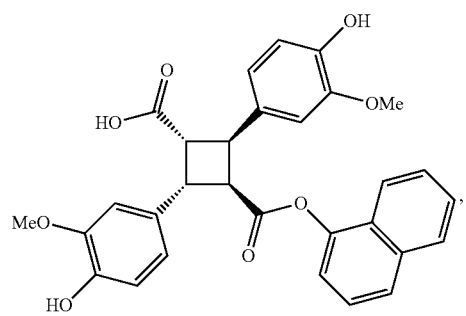
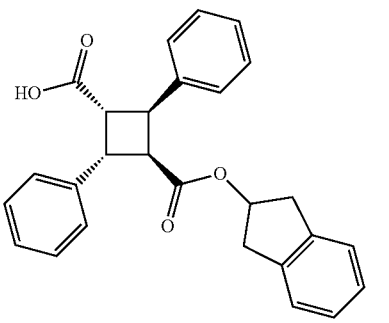
or
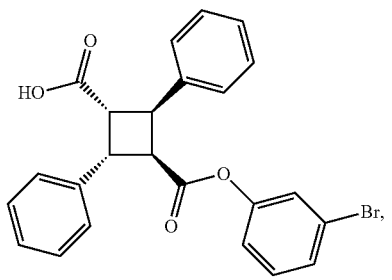
or an enantiomer or racemate thereof;
or a pharmaceutically acceptable salt thereof.

In some embodiments, the compound having the structure:
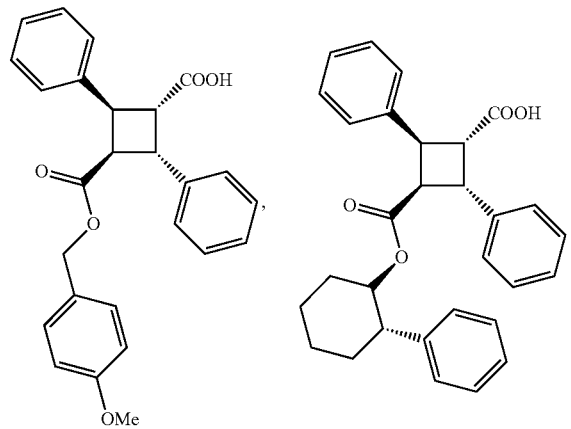
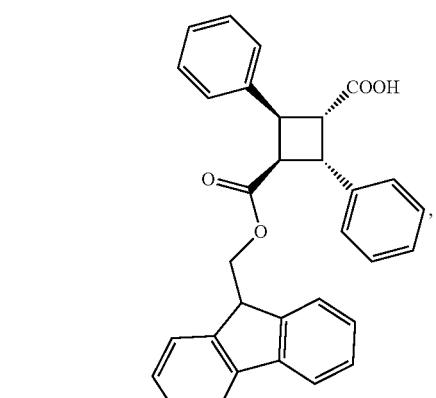
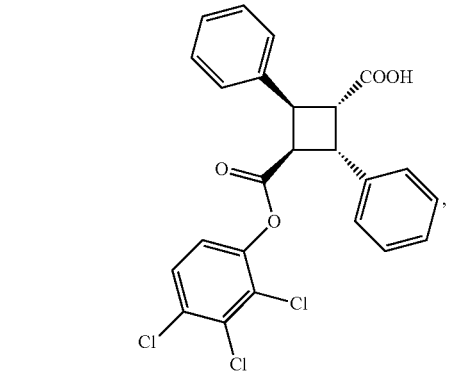
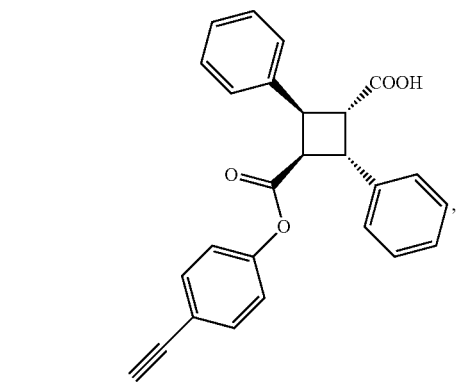
-continued
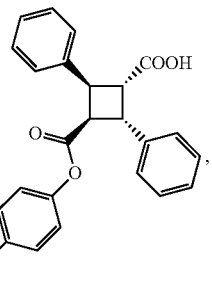
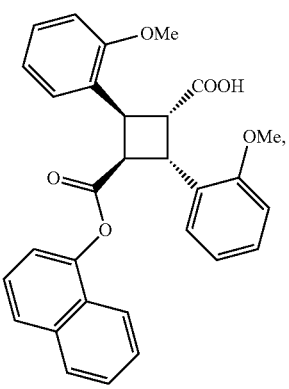
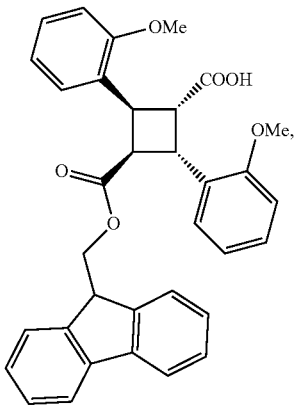
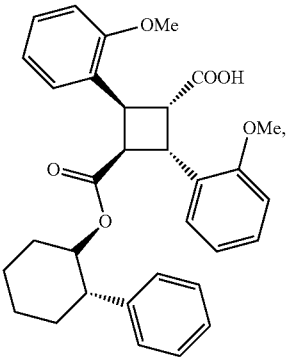

-continued
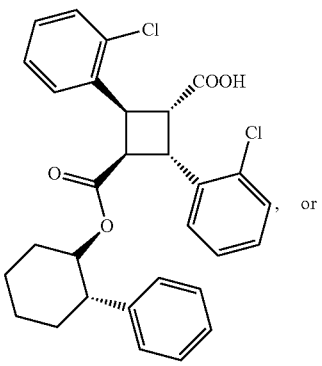
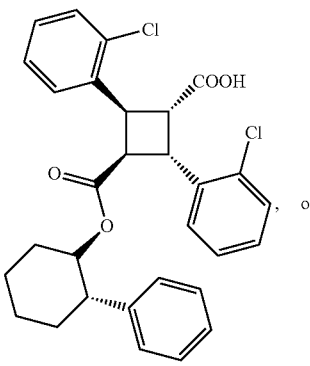
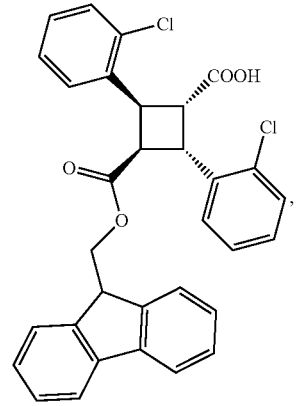 [SMILES: O=C(O)[C@H]1[C@H](c2ccccc2Cl)[C@H](C(=O)OCC2c3ccccc3-c3ccccc32)[C@H]1c1ccccc1Cl]
or enantiomer or racemate thereof;
or a pharmaceutically acceptable salt thereof.
In some embodiments, the compound having the structure:
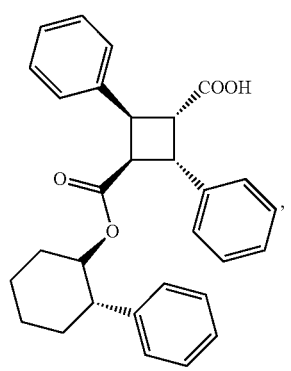
-continued
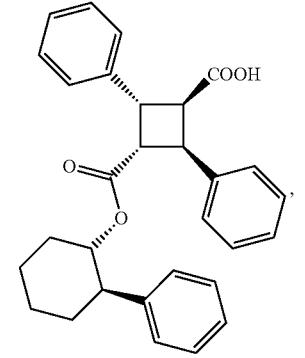
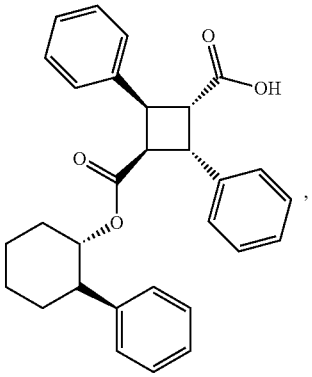
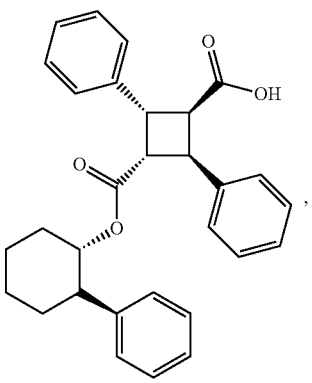
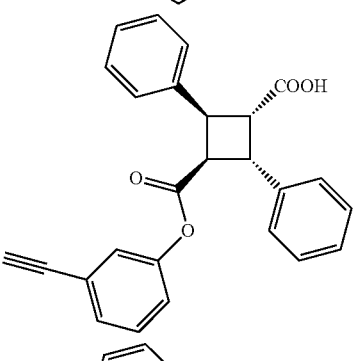
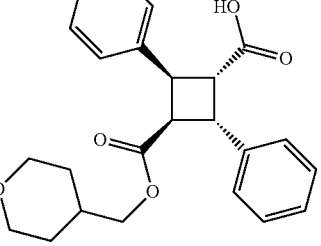

-continued
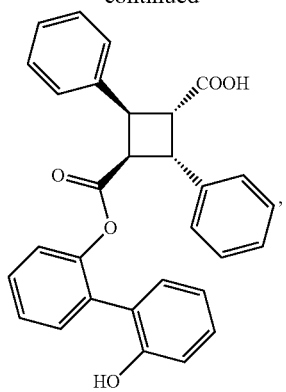
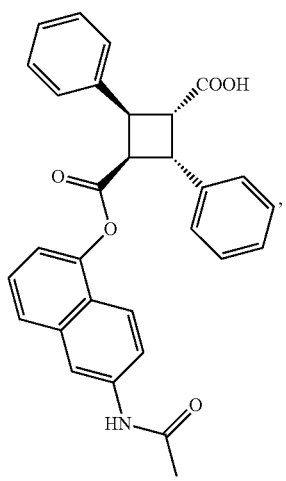
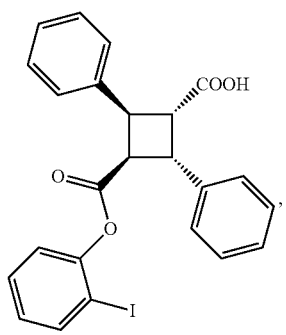
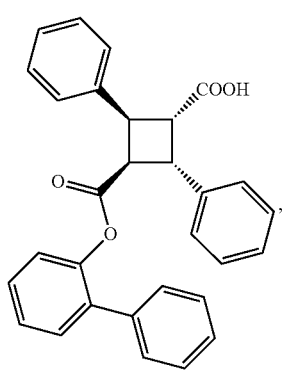
-continued
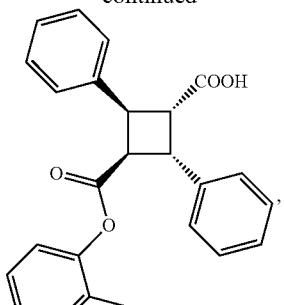
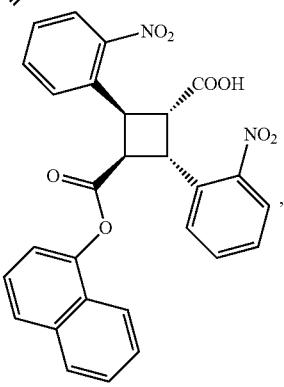
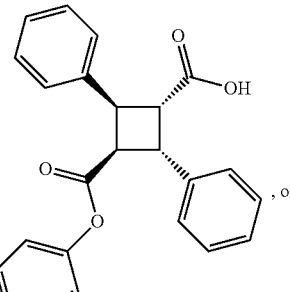
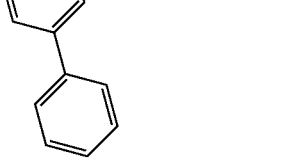, or
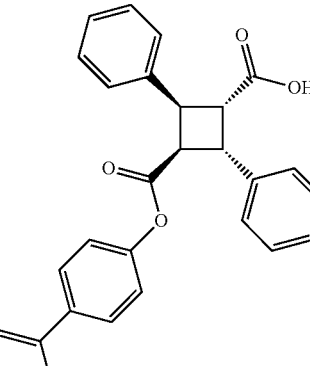
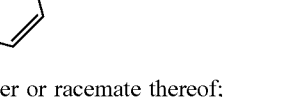
or enantiomer or racemate thereof;
or a pharmaceutically acceptable salt thereof.

In some embodiments, the compound wherein R$_{13}$ is

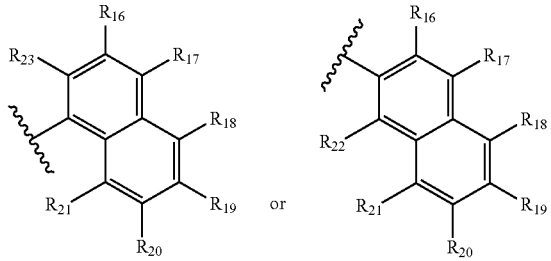

wherein each of R$_{16}$, R$_1$, RIB, R$_{19}$, R$_{20}$, R$_{21}$, R$_{22}$ and R$_{23}$ are each, independently, H, halogen, —NO$_2$, —CN, —NHR$_{24}$, —NR$_{24}$R$_{25}$, —SR$_{27}$, —SO$_2$R$_{28}$, —OR$_{29}$, —CO$_2$R$_{30}$, CF$_3$, -alkyl-NR$_{24}$R$_{25}$, -alykl-OR$_{29}$, C$_{1-10}$ alkyl, C$_{2-10}$ alkenyl, C$_{2-10}$ alkynyl, aryl, heteroaryl, or heterocyclyl;

wherein R$_{24}$, R$_{25}$, R$_{26}$, R$_{21}$, R$_{27}$, R$_{28}$, R$_{29}$ and R$_{30}$ are each, independently, H, CF$_3$, C$_{1-10}$ alkyl, C$_{2-10}$ alkenyl, C$_{2-10}$ alkynyl, heteroalkyl, cycloheteroalkyl, aryl, heteroaryl, or heterocyclyl.

In some embodiments, the compound wherein R$_{13}$ is

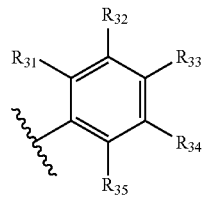

wherein each of R$_{31}$, R$_{32}$, R$_{33}$, R$_{34}$ and R$_{35}$ are each, independently, H, halogen, —NO$_2$, —CN, —NHR$_{24}$, —NR$_{24}$R$_{25}$, —SR$_{27}$, —SO$_2$R$_{28}$, —OR$_{29}$, —CO$_2$R$_{30}$, CF$_3$, -alkyl-NR$_{24}$R$_{25}$, -alkyl-OR$_{29}$, C$_{1-10}$ alkyl, C$_{2-10}$ alkenyl, C$_{2-10}$ alkynyl, aryl, heteroaryl, or heterocyclyl;

wherein R$_{24}$, R$_{25}$, R$_{26}$, R$_{21}$, R$_{27}$, R$_{28}$, R$_{29}$ and R$_{30}$ are each, independently, H, CF$_3$, C$_{1-10}$ alkyl, C$_{2-10}$ alkenyl, C$_{2-10}$ alkynyl, heteroalkyl, cycloheteroalkyl, aryl, heteroaryl, or heterocyclyl.

In some embodiments, the compound wherein R$_{14}$ is

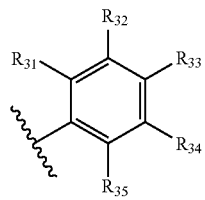

wherein each of R$_{31}$, R$_{32}$, R$_{33}$, R$_{34}$ and R$_{35}$ are each, independently, H, halogen, —NO$_2$, —CN, —NHR$_{24}$, —NR$_{24}$R$_{25}$, —SR$_{27}$, —SO$_2$R$_{28}$, —OR$_{29}$, —CO$_2$R$_{30}$, CF$_3$, -alkyl-NR$_{24}$R$_{25}$, -alykl-OR$_{29}$, C$_{1-10}$ alkyl, C$_{2-10}$ alkenyl, C$_{2-10}$ alkynyl, aryl, heteroaryl, or heterocyclyl;

wherein R$_{24}$, R$_{25}$, R$_{26}$, R$_{21}$, R$_{27}$, R$_{28}$, R$_{29}$ and R$_{30}$ are each, independently, H, CF$_3$, C$_{1-10}$ alkyl, C$_{2-10}$ alkenyl, C$_{2-10}$ alkynyl, heteroalkyl, cycloheteroalkyl, aryl, heteroaryl, or heterocyclyl.

In some embodiments, the compound wherein R$_{14}$ is

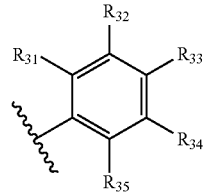

wherein each of R$_{31}$, R$_{32}$, R$_{34}$ and R$_{35}$ are each, independently, H, halogen, —NO$_2$, —CN, —NHR$_{24}$, —NR$_{24}$R$_{25}$, —SR$_{27}$, —SO$_2$R$_{26}$, —OR$_{29}$, —CO$_2$R$_3$>, CF$_3$, -alkyl-NR$_{24}$R$_{25}$, -alkyl-OR$_{29}$, C$_{1-10}$ alkyl, C$_{2-10}$ alkenyl, C$_{2-10}$ alkynyl, aryl, heteroaryl, or heterocyclyl;

wherein R$_{24}$, R$_{25}$, R$_{26}$, R$_{21}$, R$_{27}$, R$_{28}$, R$_{29}$ and R$_{30}$ are each, independently, H, CF$_3$, C$_{1-10}$ alkyl, C$_{2-10}$ alkenyl, C$_{2-10}$ alkynyl, heteroalkyl, cycloheteroalkyl, aryl, heteroaryl, or heterocyclyl; and R$_{33}$ is halo or —OR$_{29}$, wherein R$_{29}$ is H or C$_{1-10}$ alkyl, In some embodiments, the triazolo is substituted with a polyether.

In some embodiments, R$_{13}$ is other than naphthyl. In some embodiments, R$_{14}$ is other than naphthyl. In some embodiments, R$_{13}$ and R$_1$ are each other than naphthyl.

In some embodiments, R$_{13}$ is cycloalkyl, monoaryl or heteroaryl.

In some embodiments, R$_{14}$ is CF$_3$, cycloalkyl, cycloheteroalkyl, monoaryl or heteroaryl.

In some embodiments, wherein one of R$_1$ or R$_2$ is —C(=O)O-alkyl-R$_{14}$, wherein R$_{14}$ is CF$_3$, cycloalkyl, cycloheteroalkyl, aryl or heteroaryl, and the alkyl in —C(=O)O-alkyl-R$_{14}$ is unbranched.

The present invention also provides a pharmaceutical composition comprising the compound of the present invention and a pharmaceutically acceptable carrier.

The present invention also provides a salt of any of the above compounds.

The present invention also provides an ester of any of the above compounds.

The present invention also provides an enantiomer of any of the above compounds.

In some embodiments, a method of inhibiting the activity of a Fatty Acid Binding Protein (FABP) comprising contacting the FABP with the compound of the present invention.

In some embodiments, the method wherein the compound inhibits binding of an FABP ligand to the FABP.

In some embodiments, the method wherein the FABP ligand is an endocannabinoid ligand.

In some embodiments, the method wherein the FABP ligand is anandamide (AEA) or 2-arachidonoylglycerol (2-AG).

In some embodiments, the method of inhibiting the activity of a Fatty Acid Binding Protein (FABP) comprising contacting the FABP with a compound having the structure:

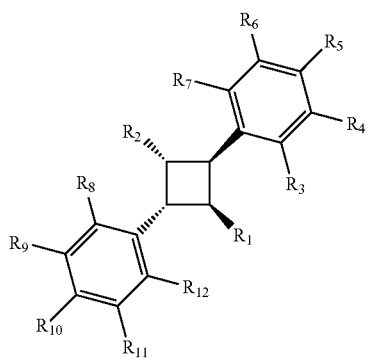

wherein
one of $R_1$ or $R_2$ is —C(=O)OH and the other of $R_1$ or $R_2$ is —C(=O)O$R_{13}$ or —C(=O) O-alkyl-$R_{14}$,
wherein
$R_{13}$ is H, cycloalkyl, aryl or heteroaryl, and
$R_{14}$ is $CF_3$, cycloalkyl, aryl or heteroaryl; and
$R_3$, $R_4$, $R_5$, $R_6$, $R_7$, $R_8$, $R_9$, $R_{10}$, $R_{11}$ and $R_{12}$ are each independently, H, halogen or —O$R_{15}$,
wherein $R_{15}$ is H, $C_{1-10}$ alkyl, $C_{2-10}$ alkenyl, $C_{2-10}$ alkynyl, aryl, or heteroaryl,
or its enantiomer or racemate;
or a pharmaceutically acceptable salt thereof.

In some embodiments, the method wherein the compound inhibits binding of an FABP ligand to the FABP.

In some embodiments, the method wherein the FABP ligand is an endocannabinoid ligand.

In some embodiments, the method wherein the FABP ligand is anandamide (AEA) or 2-arachidonoylglycerol (2-AG).

In some embodiments, the method wherein when one of $R_1$ or $R_2$ is —C(=O)OH and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O) O$R_{13}$ where $R_{13}$ is 1-naphthalene or 2-naphthalene or —C(=O)O-alkyl-$R_{14}$ where the alkyl is a branched $C_2$ alkyl and the $R_{14}$ is phenyl.

In some embodiments, the method wherein the compound has the structure:

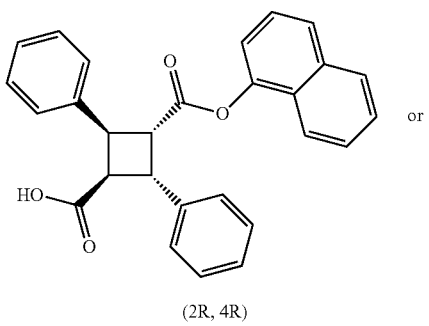

3A (2R, 4R)

or

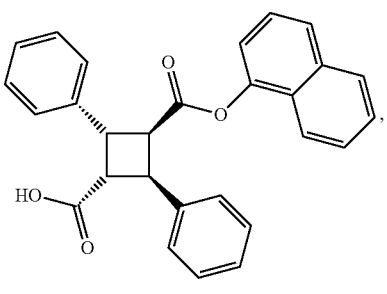

3B (2S, 4S)

or a pharmaceutically acceptable salt thereof.

Compound 3 refers to a racemic mixture of the above compounds 3A and 3B.

Compounds of the present invention include the following:

| Compound | Compound Structure | Compound | Compound Structure |
|---|---|---|---|
| 3f | (cyclobutane with two phenyl groups, COOH, and cyclohexyl ester) | 3m | (cyclobutane with two phenyl groups, COOH, and indanyl ester) |
| 4d | (cyclobutane with two 4-hydroxyphenyl groups, COOH, and dihydronaphthyl ester) | 3c | (cyclobutane with two phenyl groups, COOH, and 4-fluorobenzyl ester) |

-continued

| Compound | Compound Structure | Compound | Compound Structure |
|---|---|---|---|
| 3a | 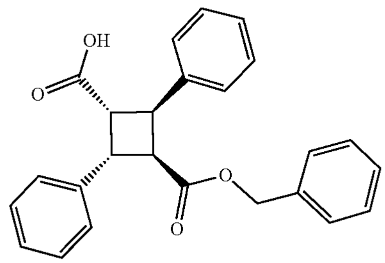 [SMILES: O=C(O)[C@H]1[C@@H](c2ccccc2)[C@H](C(=O)OCc2ccccc2)[C@@H]1c1ccccc1] | 3d | 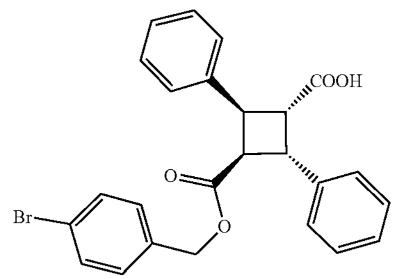 [SMILES: O=C(O)[C@H]1[C@H](c2ccccc2)[C@H](C(=O)OCc2ccc(Br)cc2)[C@H]1c1ccccc1] |
| 3r | 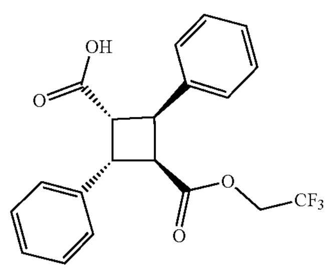 [SMILES: O=C(O)[C@H]1[C@@H](c2ccccc2)[C@H](C(=O)OCC(F)(F)F)[C@@H]1c1ccccc1] | 3l | 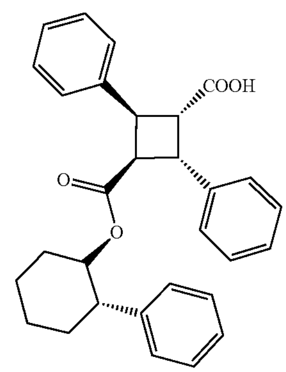 |
| 3b | 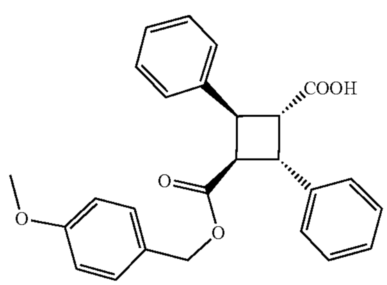 [SMILES: COc1ccc(COC(=O)[C@H]2[C@@H](c3ccccc3)[C@H](C(=O)O)[C@@H]2c2ccccc2)cc1] | 3f | 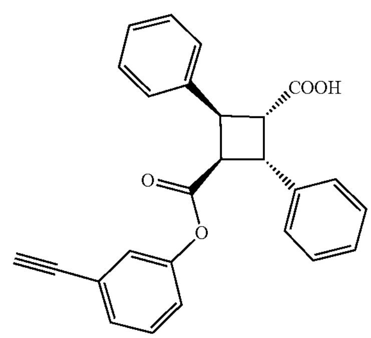 [SMILES: C#Cc1cccc(OC(=O)[C@H]2[C@@H](c3ccccc3)[C@H](C(=O)O)[C@@H]2c2ccccc2)c1] |
| 3l-A | 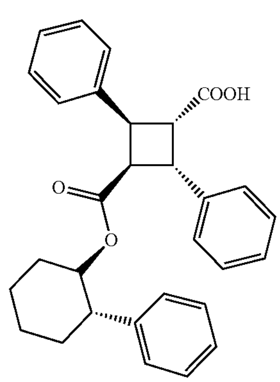 | 3t | 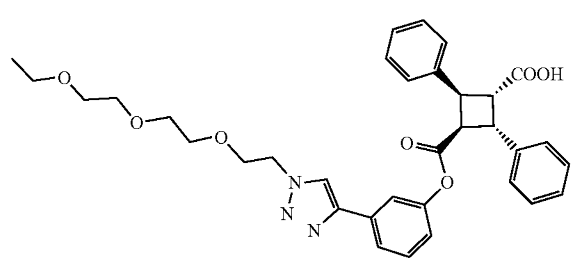 |

-continued

| Compound | Compound Structure | Compound | Compound Structure |
|---|---|---|---|
| 3l-B | 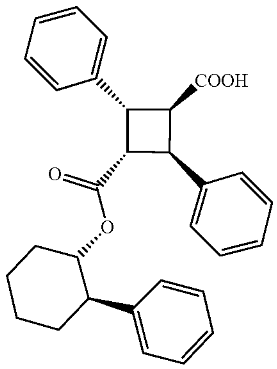 | 3j | 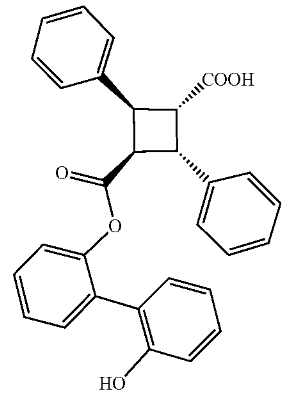 [SMILES: O=C(O)[C@H]1[C@H](c2ccccc2)[C@H](C(=O)Oc2ccccc2-c2ccccc2O)[C@H]1c1ccccc1] |
| 3q | 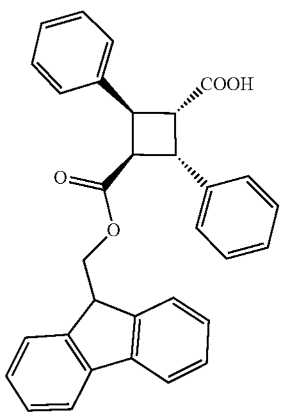 [SMILES: O=C(O)[C@H]1[C@H](c2ccccc2)[C@H](C(=O)OCC2c3ccccc3-c3ccccc32)[C@H]1c1ccccc1] | 3o | 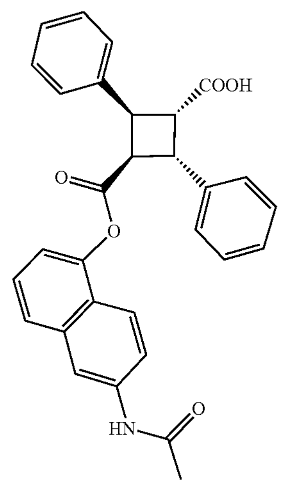 [SMILES: CC(=O)Nc1ccc2c(OC(=O)[C@H]3[C@@H](c4ccccc4)[C@H](C(=O)O)[C@@H]3c3ccccc3)cccc2c1] |
| 3k | 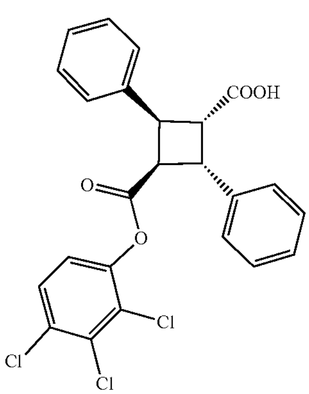 [SMILES: O=C(O)[C@H]1[C@H](c2ccccc2)[C@H](C(=O)Oc2ccc(Cl)c(Cl)c2Cl)[C@H]1c1ccccc1] | 3e | 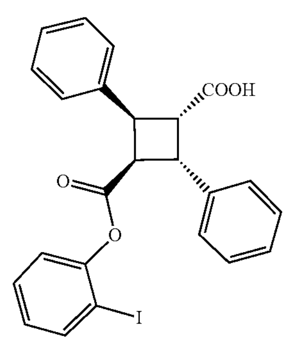 [SMILES: O=C(O)[C@H]1[C@H](c2ccccc2)[C@H](C(=O)Oc2ccccc2I)[C@H]1c1ccccc1] |

-continued

| Compound | Compound Structure | Compound | Compound Structure |
|---|---|---|---|
| 3g | 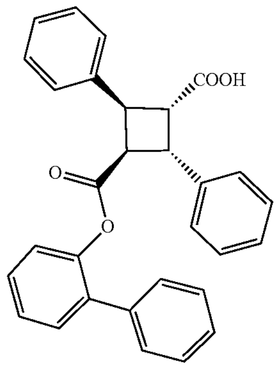 [SMILES: O=C(O)[C@H]1[C@H](c2ccccc2)[C@H](C(=O)Oc2ccccc2-c2ccccc2)[C@H]1c1ccccc1] | 4b | 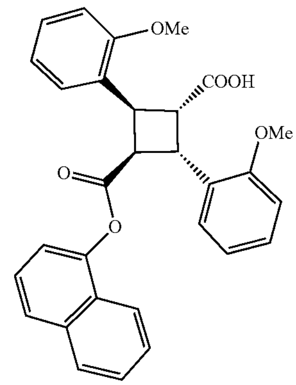 [SMILES: COc1ccccc1[C@H]1[C@H](C(=O)O)[C@H](c2ccccc2OC)[C@H]1C(=O)Oc1cccc2ccccc12] |
| 3p | 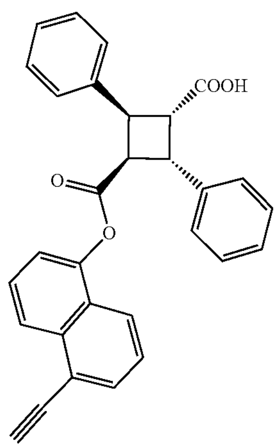 [SMILES: C#Cc1cccc2c(OC(=O)[C@H]3[C@@H](c4ccccc4)[C@H](C(=O)O)[C@@H]3c3ccccc3)cccc12] | 4a | 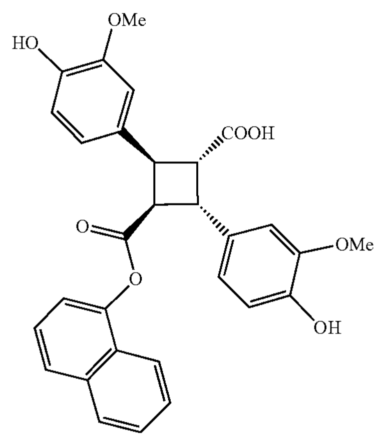 [SMILES: COc1cc([C@H]2[C@H](C(=O)O)[C@H](c3ccc(O)c(OC)c3)[C@H]2C(=O)Oc2cccc3ccccc23)ccc1O] |
| 4j | 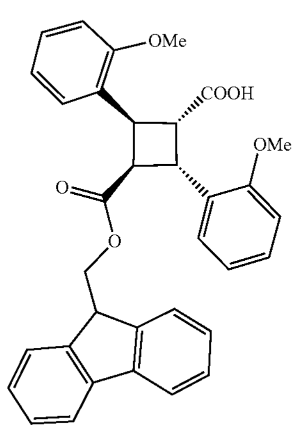 [SMILES: COc1ccccc1[C@H]1[C@H](C(=O)O)[C@H](c2ccccc2OC)[C@H]1C(=O)OCC1c2ccccc2-c2ccccc21] | 3i | 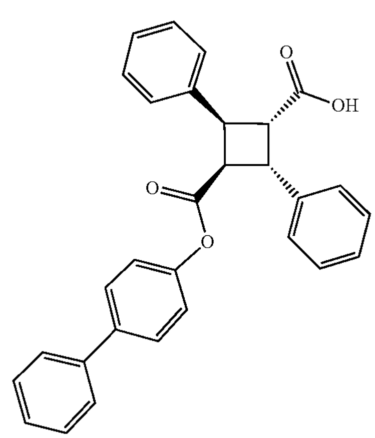 [SMILES: O=C(O)[C@H]1[C@H](c2ccccc2)[C@H](C(=O)Oc2ccc(-c3ccccc3)cc2)[C@H]1c1ccccc1] |

| Compound | Compound Structure | Compound | Compound Structure |
|---|---|---|---|
| 4e | (structure with OMe groups, COOH, cyclobutane, cyclohexyl-phenyl ester) | 3h | (structure with phenyl groups, COOH, cyclobutane, biphenyl ester) |
| 4g | (structure with 2,6-dichlorophenyl groups, COOH, cyclobutane, cyclohexyl-phenyl ester) | 4c | (structure with 2-nitrophenyl groups, COOH, cyclobutane, naphthyl ester) |
| 4f | (structure with 2-chlorophenyl groups, COOH, cyclobutane, cyclohexyl-phenyl ester) | 4k | (structure with 2-chlorophenyl groups, COOH, cyclobutane, fluorenylmethyl ester) |

In some embodiments, the compound is the (S, S) enantiomer. In some embodiments, the compound is the (R,R) enantiomer.

In some embodiments, the composition comprises a mixture of enantiomers enriched in (S,S) enantiomer. In some embodiments, the composition comprises a mixture of enantiomers enriched in (R,R) enantiomer.

In some embodiments, the method wherein the compound is the (S,S) enantiomer. In some embodiments, the method wherein the compound is the (R,R) enantiomer.

In some embodiments of the method of inhibiting the activity of a Fatty Acid Binding Protein (FABP), wherein the compound inhibits binding of an FABP ligand to the FABP.

In some embodiments of the method of inhibiting the activity of a Fatty Acid Binding Protein (FABP), wherein the FABP ligand is an endocannabinoid ligand.

In some embodiments of the method of inhibiting the activity of a Fatty Acid Binding Protein (FABP), wherein the FABP ligand is anandamide (AEA) or 2-arachidonoylglycerol (2-AG).

In some embodiments, a method of treating a neurological disorder which affects at least one of movement, memory, mood, appetite, nociception, endocrine regulation, thermoregulation, sensory perception, or cognitive functions.

In some embodiments, a method of treating a neurological disorder associated with drug addiction, depression, compulsive behavior, neuropathic pain, or a movement disorder.

In some embodiments, a method of treating drug addiction, depression, compulsive behavior, neuropathic pain, inflammatory pain, or a movement disorder.

In some embodiments, a method of treating pain, neuropathic pain, or inflammatory pain.

In some embodiments, a method of treating a subject afflicted with a neurological disorder which affects at least one of movement, memory, mood, appetite, nociception, endocrine regulation, thermoregulation, sensory perception, or cognitive functions, comprising administering to the subject a compound of the present application.

In some embodiments, a method of treating a subject afflicted with a neurological disorder associated with drug addiction, depression, compulsive behavior, neuropathic pain, or a movement disorder, comprising administering to the subject a compound of the present application.

In some embodiments, a method of treating a subject afflicted with drug addiction, depression, compulsive behavior, neuropathic pain, inflammatory pain, or a movement disorder, comprising administering to the subject a compound of the present application.

In some embodiments, a method of treating a subject afflicted with pain, neuropathic pain, or inflammatory pain, comprising administering to the subject a compound of the present application.

As used herein, the term "endocannabinoid" includes any molecule that activates cannabinoid receptors. Examples of such receptors are CB1 and CB2. Examples of endocannabinoids are arachidonoyl ethanolamide (AEA) and 2-arachidonoyl glycerol (2-AG).

As used herein, the term "fatty acid binding protein" or "FABP" refers to fatty acid binding proteins (FABPs) that function as intracellular carriers that shuttle cannabinoids (and by extension fatty acid amides (FAAs)) to FAAH where cannabinoids are hydrolyzed and degraded. Further, uptake of endocannabinoids (and by extension FAAs) by the cell and the subsequent hydrolysis of endocannabinoids (and by extension FAAs) are enhanced by FABPs, and inhibiting the interaction of endocannabinoids (and by extension FAAs) with FABPs reduces endocannabinoid (and by extension FAA) uptake and hydrolysis. FABPS include, for example, fatty acid binding protein 1 (FABP 1), fatty acid binding protein 2 (FABP 2), fatty acid binding protein 3 (FABP 3), fatty acid binding protein 4 (FABP 4), fatty acid binding protein 5 (FABP 5), fatty acid binding protein 6 (FABP 6), fatty acid binding protein 7 (FABP 7), fatty acid binding protein 8 (FABP 8), fatty acid binding protein 9 (FABP 9), fatty acid binding protein 10 (FABP 10), fatty acid binding protein 11 (FABP 11), fatty acid binding protein 5-like (FABP 5-like 1), fatty acid binding protein 5-like 2 (FABP 5-like 2), fatty acid binding protein 5-like 3 (FABP 5-like 3), fatty acid binding protein 5-like 4 (FABP 5-like 4), fatty acid binding protein 5-like 5 (FABP 5-like 5), fatty acid binding protein 5-like 6 (FABP 5-like 6), and fatty acid binding protein 5-like 7 (FABP 5-like 7) (see Chmurzynska et al. 2006 and PCT International Application Publication No. WO 2010/083532 A1, the contents of each of which are hereby incorporated by reference).

As used herein, the term "therapeutic agent" refers to any agent used to treat a disease or that provides a beneficial therapeutic effect to a subject.

As used herein, the phrase "inhibits the interaction" is employed herein to refer to any disruption, partial or total, of the natural effect of FABPs on the metabolism of endocannabinoids.

As used herein, the term "activity" refers to the activation, production, expression, synthesis, intercellular effect, and/or pathological or aberrant effect of the referenced molecule, either inside and/or outside of a cell. Such molecules include, but are not limited to, cytokines, enzymes, growth factors, pro-growth factors, active growth factors, and pro-enzymes. Molecules such as cytokines, enzymes, growth factors, pro-growth factors, active growth factors, and pro-enzymes may be produced, expressed, or synthesized within a cell where they may exert an effect. Such molecules may also be transported outside of the cell to the extracellular matrix where they may induce an effect on the extracellular matrix or on a neighboring cell. It is understood that activation of inactive cytokines, enzymes and pro-enzymes may occur inside and/or outside of a cell and that both inactive and active forms may be present at any point inside and/or outside of a cell. It is also understood that cells may possess basal levels of such molecules for normal function and that abnormally high or low levels of such active molecules may lead to pathological or aberrant effects that may be corrected by pharmacological intervention.

As used herein, "treating" means reducing, slowing, stopping, preventing, reversing, or in any way improving the progression of a disease or disorder or a symptom of the disease or disorder.

In some embodiments, the compounds of the present invention include all hydrates, solvates, and complexes of the compounds used by this invention.

In some embodiments, if a chiral center or another form of an isomeric center is present in a compound of the present invention, all forms of such isomer or isomers, including enantiomers and diastereomers, are intended to be covered herein.

In some embodiments, if a chiral center or another form of an isomeric center is present in a compound of the present invention, only enantiomeric forms are intended to be covered herein.

Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. Example 6 provides a method by which to obtain the individual enantiomers of each of the compound contained herein. A method by which to obtain the individual enantiomers is also described in WO 2014/015276, published Jan. 23, 2014, the contents of which are hereby incorporated by reference.

As used herein, "enantiomers" are non-identical, non-superimposible mirror images of each other. For any given chiral compound, only one pair of enantiomers exists. The enantiomers can be separated using known techniques, including those described in Pure and Applied Chemistry 69, 1469-1474, (1997) IUPAC.

In cases in which compounds have unsaturated carbon-carbon double bonds, both the cis (Z) and trans (E) isomers are within the scope of this invention.

The compounds of the subject invention may have spontaneous tautomeric forms. In cases wherein compounds may exist in tautomeric forms, such as keto-enol tautomers, each tautomeric form is contemplated as being included within this invention whether existing in equilibrium or predominantly in one form.

In the compound structures depicted herein, hydrogen atoms are not shown for carbon atoms having less than four bonds to non-hydrogen atoms.

However, it is understood that enough hydrogen atoms exist on said carbon atoms to satisfy the octet rule.

This invention also provides isotopic variants of the compounds disclosed herein, including wherein the isotopic atom is $^2H$ and/or wherein the isotopic atom $^{13}C$. Accordingly, in the compounds provided herein hydrogen can be enriched in the deuterium isotope. It is to be understood that the invention encompasses all such isotopic forms.

It is understood that the structures described in the embodiments of the methods hereinabove can be the same as the structures of the compounds described hereinabove.

It is understood that where a numerical range is recited herein, the present invention contemplates each integer between, and including, the upper and lower limits, unless otherwise stated.

Except where otherwise specified, if the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{11}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^1H$, $^2H$, or $^3H$. Furthermore, any compounds containing $^2H$ or $^3H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano, carbamoyl and aminocarbonyl and aminothiocarbonyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" includes both branched and straight-chain saturated aliphatic hydrocarbon groups having the specified number of carbon atoms and may be unsubstituted or substituted. Thus, $C_1$-$C_n$ as in "$C_1$-$C_n$ alkyl" is defined to include individual groups each having 1, 2, ..., n–1 or n carbons in a linear or branched arrangement. For example, $C_1$-$C_6$, as in "$C_1$-$C_6$ alkyl" is defined to include individual groups each having 1, 2, 3, 4, 5, or 6 carbons in a linear or branched arrangement, and specifically includes methyl, ethyl, n-propyl, isopropyl, n-butyl, t-butyl, pentyl, hexyl, and octyl.

As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. For example, "$C_2$-$C_6$ alkenyl" means an alkenyl radical having 2, 3, 4, 5, or 6 carbon atoms, and up to 1, 2, 3, 4, or 5 carbon-carbon double bonds respectively. Alkenyl groups include ethenyl, propenyl, butenyl and cyclohexenyl.

The term "alkynyl" refers to a hydrocarbon radical straight or branched, containing at least 1 carbon to carbon triple bond, and up to the maximum possible number of non-aromatic carbon-carbon triple bonds may be present, and may be unsubstituted or substituted. Thus, "$C_2$-$C_6$ alkynyl" means an alkynyl radical having 2 or 3 carbon atoms and 1 carbon-carbon triple bond, or having 4 or 5 carbon atoms and up to 2 carbon-carbon triple bonds, or having 6 carbon atoms and up to 3 carbon-carbon triple bonds. Alkynyl groups include ethynyl, propynyl and butynyl.

"Alkylene", "alkenylene" and "alkynylene" shall mean, respectively, a divalent alkane, alkene and alkyne radical, respectively. It is understood that an alkylene, alkenylene, and alkynylene may be straight or branched. An alkylene, alkenylene, and alkynylene may be unsubstituted or substituted.

As used herein, "heteroalkyl" includes both branched and straight-chain saturated aliphatic hydrocarbon groups having the specified number of carbon atoms and at least 1 heteroatom within the chain or branch.

As used herein, "heterocycle" or "heterocyclyl" as used herein is intended to mean a 5- to 10-membered nonaromatic ring containing from 1 to 4 heteroatoms selected from the group consisting of O, N and S, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

As herein, "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "monocycle" includes any stable polyatomic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl. As used herein, "bicycle" includes any stable polyatomic carbon ring of up to 10 atoms that is fused to a polyatomic carbon ring of up to 10 atoms with each ring being independently unsubstituted or substituted. Examples of such non-aromatic bicycle elements include but are not limited to: decahydronaphthalene. Examples of such aromatic bicycle elements include but are not limited to: naphthalene.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include phenyl, p-toluenyl (4-methylphenyl), naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

As used herein, the term "polycyclic" refers to unsaturated or partially unsaturated multiple fused ring structures, which may be unsubstituted or substituted.

The term "alkylryl" refers to alkyl groups as described above wherein one or more bonds to hydrogen contained therein are replaced by a bond to an aryl group as described above. It is understood that an "arylalkyl" group is connected to a core molecule through a bond from the alkyl group and that the aryl group acts as a substituent on the alkyl group. Examples of arylalkyl moieties include, but are not limited to, benzyl (phenylmethyl), p-trifluoromethylbenzyl (4-trifluoromethyl-phenylmethyl), 1-phenylethyl, 2-phenylethyl, 3-phenylpropyl, 2-phenylpropyl and the like.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "alkylheteroaryl" refers to alkyl groups as described above wherein one or more bonds to hydrogen contained therein are replaced by a bond to an heteroaryl group as described above. It is understood that an "alkylheteroaryl" group is connected to a core molecule through a bond from the alkyl group and that the heteroaryl group acts as a substituent on the alkyl group. Examples of alkylheteroaryl moieties include, but are not limited to, —CH$_2$—(C$_5$H$_4$N), —CH$_2$—CH$_2$—(C$_5$H$_4$N) and the like.

The term "heterocycle" or "heterocyclyl" refers to a mono- or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

The alkyl, alkenyl, alkynyl, aryl, heteroaryl and heterocyclyl substituents may be substituted or unsubstituted, unless specifically defined otherwise. In the compounds of the present invention, alkyl, alkenyl, alkynyl, aryl, heterocyclyl and heteroaryl groups can be further substituted by replacing one or more hydrogen atoms with alternative non-hydrogen groups. These include, but are not limited to, halo, hydroxy, mercapto, amino, carboxy, cyano and carbamoyl.

As used herein, the term "halogen" refers to F, Cl, Br, and I.

The terms "substitution", "substituted" and "substituent" refer to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and iso-propoxy; aryloxy groups, such as phenoxy; arylalkyloxy, such as benzyloxy (phenylmethoxy) and p-trifluoromethyl-benzyloxy (4-trifluoromethylphenylmethoxy); heteroary-loxy groups; sulfonyl groups, such as trifluoromethanesulfo-nyl, methanesulfonyl, and p-toluenesulfonyl; nitro, nitrosyl; mercapto; sulfanyl groups, such as methylsulfanyl, ethyl-sulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or pluraly. By independently substituted, it is meant that the (two or more) substituents can be the same or different.

The term "tolyl" refers to one of the three $CH_3C_6H_4$-isomeric groups derived from toluene.

The term "naphthalene" refers to a bicyclic aromatic hydrocarbon consisting of a fused pair of benzene rings.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity. The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

The compounds used in the method of the present invention may be prepared by techniques well known in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5$^{th}$ Edition (1996), March's Advanced Organic Chemistry: Reactions, Mechanisms, and Structure, Michael B. Smith, Jerry March, (Wiley-Interscience) 5$^{th}$ Edition (2007), and references therein, which are incorporated by reference herein. However, these may not be the only means by which to synthesize or obtain the desired compounds.

Another aspect of the invention comprises a compound used in the method of the present invention as a pharmaceutical composition.

In some embodiments, a pharmaceutical composition comprising the compound of the present invention and a pharmaceutically acceptable carrier.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, 30$^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds.

In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

The compounds of the present invention may also form salts with basic amino acids such a lysine, arginine, etc. and with basic sugars such as N-methylglucamine, 2-amino-2-deoxyglucose, etc. and any other physiologically non-toxic basic substance.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier as are slow-release vehicles.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antitumor agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or topically onto a site of disease or lesion, all using dosage forms well known to those of ordinary skill in the pharmaceutical arts.

The compounds used in the method of the present invention can be administered in admixture with suitable pharmaceutical diluents, extenders, excipients, or in carriers such as the novel programmable sustained-release multi-compartmental nanospheres (collectively referred to herein as a pharmaceutically acceptable carrier) suitably selected with respect to the intended form of administration and as consistent with conventional pharmaceutical practices. The unit will be in a form suitable for oral, nasal, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamellar vesicles, and multilamellar vesicles. Liposomes can be formed from a variety of phospholipids such as lecithin, sphingomyelin, proteolipids, protein-encapsulated vesicles or from cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropyl-methacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials such as solutol and/or ethanol to make them compatible with the type of injection or delivery system chosen.

The compounds and compositions of the present invention can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by topical administration, injection or other methods, to the afflicted area, such as a wound, including ulcers of the skin, all using dosage forms well known to those of ordinary skill in the pharmaceutical arts.

Specific examples of pharmaceutically acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

The term "prodrug" as used herein refers to any compound that when administered to a biological system generates the compound of the invention, as a result of spontaneous chemical reaction(s), enzyme catalyzed chemical reaction(s), photolysis, and/or metabolic chemical reaction(s). A prodrug is thus a covalently modified analog or latent form of a compound of the invention.

The active ingredient can be administered orally in solid dosage forms, such as capsules, tablets, powders, and chewing gum; or in liquid dosage forms, such as elixirs, syrups, and suspensions, including, but not limited to, mouthwash and toothpaste. It can also be administered parentally, in sterile liquid dosage forms.

Solid dosage forms, such as capsules and tablets, may be enteric-coated to prevent release of the active ingredient compounds before they reach the small intestine. Materials that may be used as enteric coatings include, but are not limited to, sugars, fatty acids, proteinaceous substances such as gelatin, waxes, shellac, cellulose acetate phthalate (CAP), methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), and methyl methacrylate-methacrylic acid copolymers.

The compounds and compositions of the invention can be coated onto stents for temporary or permanent implantation into the cardiovascular system of a subject.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Materials and Methods

Those having ordinary skill in the art of organic synthesis will appreciate that modifications to general procedures and synthetic routes contained in this application can be used to yield additional derivatives and structurally diverse compounds. Suitable organic transformations are described in in March's Advanced Organic Chemistry: Reactions, Mechanisms, and Structure (Wiley-Interscience; 6th edition, 2007), the content of which is hereby incorporated by reference.

High Throughput Fluorescence Displacement Assay with NBD-Stearate

FABP5 was purified and delipidated as described previously (Kaczocha, M. et al. 2012). FABP5 (30 µg), NBD-stearate (1 µM), and a competitor test compound were incubated in 30 mM Tris-HCl, 100 mM NaCl buffer (pH 7.6). Competitors included arachidonic acid, BMS309403, 48 test compounds from ChemDiv library, Compound 26 and Compound 49. The initial assay was run with buffer (30 mM Tris-HCl buffer), negative controls (buffer and NBD-stearate), positive controls (buffer, NBD-stearate, FABP5), and experimental wells with a variable test compound added (arachidonic acid or one of the 48 test compounds) at 10 µM. Test compounds that produced high inhibition and proved statistically significant were then added to the fluorescent assay at 10 µM and tested in triplicate to verify their success. The most effective test compound and BMS309403 were measured in increasing concentrations (0.01-50 µM), as were the Compound 26 and γ-truxillic acid 1-naphthyl ester, which were discovered following the test. The fluorescent assays were tested in the wells of Microtest 96-well Assay Plates, Optilux (BD Biosciences, Franklin Lakes, N.J.) and loss of fluorescence intensity was measured with a FLUOstar OPTIMA spectrofluorometer set to excitation and emission wavelengths of 460 nm and 544 nm, respectively. For the most effective test compounds, $IC_{50}$ values were calculated with GraphPad Prism. GraphPad Prism was also used to determine the $K_i$ of these select competitors from the equation $K_1=IC_{50}/(1+([NBD-stearate]/K_d))$. The $K_c$ of NBD-stearate for FABP5 had been determined previously through incubating FABP5 with increasing concentrations of NBD-stearate. One site binding analysis in GraphPad Prism indicated that the $K_d$ of NBD-stearate for FABP5 was 0.16 µM (Kaczocha, M. et al. 2012).

Patch-Clamp Electrophysiology in Brain Slices

DR neurons are visualized using an upright microscope (BX 51 WI, Olympus, Tokyo, Japan) equipped with a differential interference contrast and infrared imaging system. Somatic recordings from DR neurons are obtained with path electrodes (3-5 mΩ) back-filled with potassium gluconate based internal solution of the following composition: 120 mM potassium gluconate, 10 mM KCl, 10 mM $Na_2$-phosphocreatine, 10 mM HEPES, 1 mM $MgCl_2$, 1 mM EGTA, 2 mM $Na_2$-ATP, 0.25 mM Na-GTP, pH 7.3 (Adjusted with KOH; Osmolarity, 280 to 290 mOsmol/l). All the recordings were conducted in the presence of $GABA_A$ receptor antagonist picrotoxin (100 µM). Excitatory postsynaptic currents (EPSCs) are evoked with a single square stimulus (intensity, 1 to 10 V, duration, 100 to 200 µs) delivered via a glass stimulating electrode. EPSCs are amplified with a Multiclamp 700B (Molecular Devices, Union City, Calif., USA) and are acquired using pClamp 10 software (Molecular Devices).

Data Analysis

The amplitude of EPSCs is determined by measuring the average current during a 2-ms period at the peak of each EPSC and subtracted from the baseline current determined during a 5-ms time window before the stimulus. All EPSC amplitudes are normalized to the mean baseline amplitude recorded for at least 10 min before drug application. Results in the text and figures are presented as mean±SEM. Statistical analysis is conducted using the Student's paired t-test.

AEA Uptake

AEA uptake assays in wild-type and FABP5 knockdown HeLa cells are performed exactly as described (Kaczocha, M. et al. 2012).

FAAH Enzyme Assay

Enzyme assays measuring the hydrolysis of [$^{14}C$]AEA in the presence of compound or the FAAH inhibitor are carried out in HeLa homogenates expressing rat FAAH as described (Kaczocha, M. et al. 2009).

PPAR Transactivation

PPARα and PPARγ transactivation assays are performed in HeLa cells exactly as described (Kaczocha, M. et al. 2012). Briefly, cells are transfected with the PPAR reporter system, incubated with GW7647, rosiglitazone, or compound for 6 hrs, followed by measurement of luciferase and β-galactosidase activity using a luminometer as described (Kaczocha, M. et al. 2012).

Animals

Male $C_{57}B16$ mice (22-30 g, Taconic Farms) are used for all experiments. The animals are group housed at room temperature and kept on a 12:12 hour light:dark cycle with ad libitum access to water and food. The animals are habituated to the experimental room for one week before testing. All experiments are approved by the Stony Brook University Institutional Animal Care and Use Committee. The experimenter is blinded to the treatment conditions of each animal.

Carrageenan-Induced Paw Edema and Thermal Hyperalgesia

Paw edema is induced by injecting 1% λ-carrageenan (20 µl, in sterile saline) into the plantar surface of the left hind paw and a control solution of saline into the right hind paw using a 27 gauge needle. Paw diameters are measured before carrageenan injection and 4 hours after injection using digital electronic calipers (Fisher) and expressed to the nearest ±0.01 mm. The compound (20 mg/kg, i.p.) is dissolved in ethanol:emulphor:saline (1:1:18), requiring sonication and gentle heating for solubilization, and is administered 45 min prior to injection of carrageenan. The cannabinoid receptor antagonists, rimonabant and SR144528 (3 mg/kg, i.p.), in ethanol:emulphor:saline (1:1:18), are injected 15 min before the FABP inhibitor. Edema is reported as the change in paw diameter at 4 hr over the baseline. Changes in paw diameter of saline-injected contralateral paws are negligible. Thermal hyperalgesia measures the latency to withdraw the paw from a focused beam of radiant heat applied to the plantar surface of the hind paw using a Hargreaves plantar apparatus (Ugo Basile) set at an intensity of 3.0. For each mouse, the average latencies consisted of three trials spaced at least 5 minutes apart. The mice are habituated to the test chamber for 30 min. The cutoff time is set at 30 sec.

Formalin Test

Mice are habituated to the observation chamber (Plexiglas box, 25 cm×25 cm×25 cm) for 30 min prior to formalin injection. The mice subsequently receive an injection of formalin (2.5% in saline, 20 µl) into the plantar surface of the right hind paw using a 27 gauge needle. The animals are immediately placed back into the observation chamber and nocifensive behavior (time spent licking or biting the paw) is recorded for 60 min. The formalin test consists of two phases with the first phase (0-5 min) reflecting nociceptor activation and the second phase (15-45 min) reflecting an inflammatory pain response.

Statistical Analyses

Behavioral data are presented as means±S.E.M. for the vehicle and inhibitor-treated groups, each consisting of at least 6 animals. Statistical significance between vehicle and inhibitor groups are determined using unpaired t-tests or one-way ANOVA followed by Dunnett's post hoc analysis. In all cases, differences of p<0.05 are considered significant.

Example 1. Synthesis of α-Truxillic Acid Monoesters

Analytical Methods.

NMR spectra were recorded on either a Bruker Ascend 700 spectrometer operating at 700 MHz for 1H acquisitions and 175 MHz for $^{13}C$ acquisitions, a Bruker 500 Advance spectrometer operating at 500 MHz and 125 MHz for $^1H$ and $^{13}C$ acquisitions, respectively, a Bruker 400 Nanobay spectrometer operating at 400 MHz, 100 MHz, and 376 MHz for 1H, $^{13}C$, and $^{19}F$ acquisitions, respectively. Chemical shifts were referenced to the residual proton solvent peaks ($^1H$: CDCl$_3$, δ 7.26; (CD$_3$)$_2$SO, δ 2.50; CD$_3$OD, δ 3.31; CD$_3$CN, δ 1.94), solvent $^{13}C$ signals (CDCl$_3$, δ 77.16; (CD$_3$)$_2$SO, δ 39.52; CD$_3$OD, δ 49.00). Signals are listed in ppm, and multiplicity identified as s=singlet, br=broad, d=doublet, t=triplet, q=quartet, m=multiplet; coupling constants in Hz; integration. High-resolution mass spectra were performed at Mass Spectrometry Services at the Univ. of Illinois at Urbana-Champaign and were obtained using Waters Q-TOF Ultima ESI mass spectrometer. Concentration under reduced pressure was performed by rotary evaporation at 25-30° C. at appropriate pressure.

Materials.

All air- and moisture-insensitive reactions were carried out under an ambient atmosphere, magnetically stirred, and monitored by thin layer chromatography (TLC) using Agela Technologies TLC plates pre-coated with 250 μm thickness silica gel 60 F254 plates and visualized by fluorescence quenching under UV light. Flash chromatography was performed on SiliaFlash® Silica Gel 40-63 μm 60 Å particle size using a forced flow of eluent at 0.3-0.5 bar pressure. All air- and moisture-sensitive manipulations were performed using oven-dried glassware, including standard Schlenk and glovebox techniques under an atmosphere of nitrogen. Diethyl ether and THF were distilled from deep purple sodium benzophenone ketyl. Methylene chloride, chloroform and acetonitrile were dried over CaH$_2$ and distilled. Methylene chloride was degassed via three freeze-pump-thaw cycles. All other chemicals were used as received. All deuterated solvents were purchased from Cambridge Isotope Laboratories.

Chemical Synthesis

α-2,4-diphenylcyclobutene-1,3-dicarboxylic acid (1a)

E-cinnamic acid (1 g, 6.7 mmol) was placed in a pyrex dish and exposed to light at 350 nm and an intensity of 280 nW/cm$^2$ for 5 days with periodic shaking. This process was performed in the solid state and monitored by $^1H$ NMR. After completion of the photoreaction, the white solid was washed with diethylether (20 mL) to give α-truxillic acid.

In the same manner, other mono ester 1b to 1f were synthesized and characterized, starting from corresponding substituted (E)-cinnamic acid.

α-2,4-Bis(2-methoxylphenyl)cyclobutene-1,3-dicarboxylic acid (1b)

White solid; $^1H$ NMR (700 MHz, DMSO-d$_6$) δ 3.74-3.79 (m, 8H), 4.42 (dd, J=10.1, 7.6 Hz, 2H), 7.20-7.24 (m, 2H), 7.25-7.28 (m, 2H), 11.90 (s, 2H). $^{13}C$ NMR (175 MHz, DMSO-d$_6$) δ 36.0, 44.6, 55.4, 110.5, 120.1, 127.1, 127.5, 127.9, 157.2, 173.4.

α-2,4-Bis(2-chlorophenyl)cyclobutene-1,3-dicarboxylic acid (1c)

White solid; $^1H$ NMR (700 MHz, DMSO-d$_6$) δ 3.89 (d, J=6.3 Hz, 2H), 4.63 (d, J=6.3 Hz, 2H), 7.08 (td, J=7.6, 1.3 Hz, 2H), 7.12 (t, J=7.0 Hz, 2H), 7.19-7.24 (m, 2H), 7.33 (d, J=7.6 Hz, 2H), 12.58 (s, 2H).

α-2,4-Bis(2,6-dichlorophenyl)cyclobutene-1,3-dicarboxylic acid (1d)

White solid; mp (in progress); $^1H$ NMR (700 MHz, dmso-d$_6$) δ 3.90 (d, J=6.3 Hz, 2H), 4.64 (d, J=6.3 Hz, 2H), 7.06-7.06 (m, 4H), 7.20-7.25 (m, 2H), 7.33 (d, J=7.6 Hz, 2H), 12.59 (s, 2H).

α-2,4-Bis(2-bromophenyl)cyclobutene-1,3-dicarboxylic acid (1e)

white solid; mp; $^1H$ NMR (700 MHz, dmso-d$_6$) 3.86 (dd, J=4.0, 2.4 Hz, 2H), 4.63 (d, J=6.4 Hz, 2H), 6.99-7.04 (m, 2H), 7.16 (t, J=7.5 Hz, 2H), 7.33 (d, J=7.7 Hz, 2H), 7.40 (d, J=7.7 Hz, 2H), 12.58 (s, 2H); $^{13}C$ NMR (175 MHz, dmso-d$_6$) δ 42.6, 43.9, 124.7, 127.1, 128.5, 129.1, 132.3, 137.8, 173.6; HRMS (ESI) m/z: calcd for C$_{18}$H$_{15}$Br$_2$O$_4$H$^+$, 451.9259, found, 451.9261; (Δ=0.44 ppm)

Benzyl α-2,4-diphenylcyclobutane-1,3-dicarboxylate (3a) and dibenzyl α-2,4-diphenylcyclobutane-1,3-dicarboxylate (5a)

To α-truxillic acid (1a, 200 mg, 0.66 mmol) suspended in thionyl chloride (3 mL) was added three drops of DMF and the mixture was heated to reflux for 3 h with stirring. The excess thionyl chloride and DMF were removed in vacuo to give the corresponding α-truxillic acid dichloride (2a) as light yellow solid, which was used directly in the subsequent reaction. To a solution of 2a in THF (10 mL) were added benzyl alcohol (0.53 mmol, 0.8 eq) and pyridine (4.0 mmoles), and the reaction mixture was stirred for 2 h. The reaction was quenched by adding distilled water (10 mL) with stirring for 30 min. The resulted solution was diluted with ethyl acetate (15 mL) and washed with aqueous copper sulfate (5 mL×3) and water (5 mL×3). The organic layer was collected, dried over MgSO$_4$, and concentrated in vacuo. The crude mixture was purified by flash chromatography on silica gel (hexanes/AcOEt/AcOH=79/20/1) as the eluent to give mono-ester 3a and diester 5a.

3a, white solid; 61% yield; $^1H$ NMR (300 MHz, acetone-d$_6$) δ 7.50-7.19 (m, 13H), 7.05 (s, 2H), 4.83 (d, J=12.3 Hz, 1H), 4.66 (d, J=12.2 Hz, 1H), 4.55-4.41 (m, 2H), 4.10-3.96 (m, 2H); $^{13}C$ NMR (101 MHz, acetone-d$_6$) δ 172.20, 171.56, 139.37, 139.32, 135.97, 128.32, 128.27, 128.21, 128.08, 127.85, 127.75, 127.64, 126.95, 126.81, 65.92, 46.69, 46.23, 41.76, 41.47.

5a, white solid; 13% yield; 1H NMR (500 MHz, acetone-d$_6$) δ 3.99-4.17 (m, 2H), 4.52 (dd, J=10.38, 7.32 Hz, 2H), 4.64 (d, J=12.21 Hz, 2H), 4.81 (d, J=12.51 Hz, 2H), 6.98-7.08 (m, 4H), 7.23-7.30 (m, 7H), 7.30-7.36 (m, 4H), 7.36-7.45 (m, 4H); $^{13}C$ NMR (126 MHz, acetone-d$_6$) δ 42.6, 47.5, 66.9, 128.0, 128.7, 128.8, 129.1, 129.2, 129.3, 136.9, 140.1, 172.3; HRMS (ESI) m/z calculated for C$_{32}$H$_{28}$O$_4$H$^+$: 477.206, found 477.2059 (Δ=0.34 ppm)

In the same manner, other mono ester 3b to 3r and di-esters 5b to 5e were synthesized and characterized, starting from α-2,4-diphenylcyclobutene-1,3-dicarboxylic acid (1a).

4-Methoxybenzyl α-2,4-diphenylcyclobutane-1,3-dicarboxylate (3b) and di(4-methoxy)benzyl α-2,4-diphenylcyclobutane-1,3-dicarboxylate (5b)

3b, white solid; 40% yield; mp 99-102° C.; $^1$H NMR (500 MHz, acetone-d$_6$) δ 3.78 (s, 3H), 3.93-4.07 (m, 2H), 4.40-4.50 (m, 2H), 4.58 (d, J=11.9 Hz, 1H), 4.74 (d, J=11.9 Hz, 1H), 6.79-6.87 (m, 2H), 6.93-7.03 (m, 2H), 7.21-7.39 (m, 8H), 7.41 (d, J=7.32 Hz, 2H); $^{13}$C NMR (126 MHz, acetone-d$_6$) δ 42.4, 42.7, 47.1, 47.6, 55.6, 66.7, 114.6, 127.7, 127.8, 128.6, 128.7, 129.1, 129.2, 130.9, 140.3, 160.6, 172.5, 173.1; HRMS (ESI) m/z calcd for C$_{26}$H$_{24}$O$_5$H$^+$: 434.1962, found 434.1964 (Δ=0.42 ppm).

5b, white solid; 12% yield; mp 145-148° C.; $^1$H NMR (500 MHz, acetone-d$_6$) δ 3.78 (s, 6H), 3.97-4.08 (m, 2H), 4.47 (dd, J=10.38, 7.32 Hz, 2H), 4.56 (d, J=12.2 Hz, 2H), 4.73 (d, J=12.2 Hz, 2H), 6.78-6.86 (m, 4H), 6.93-7.01 (m, 4H), 7.23-7.30 (m, 2H), 7.30-7.40 (m, 8H); $^{13}$C NMR (126 MHz, acetone-d$_6$) δ 42.5, 47.5, 55.6, 66.7, 114.6, 127.9, 128.6, 129.3, 130.9, 140.1, 160.6, 172.3; HRMS (ESI) m/z calcd for C$_{26}$H$_{24}$O$_5$H$^+$: 554.2536, found 544.2537 (Δ=0.2 ppm)

4-Fluorobenzyl α-2,4-diphenylcyclobutane-1,3-dicarboxylate (3c) and di(4-fluorobenzyl) α-2,4-diphenylcyclobutane-1,3-dicarboxylate (5c)

3c: white solid; 34% yield; mp 145-148° C.; $^1$H NMR (500 MHz, acetone-d$_6$) δ 4.03 (dd, J=10.38, 7.32 Hz, 2H), 4.35-4.58 (m, 2H), 4.68 (d, J=12.21 Hz, 1H), 4.80 (d, J=12.21 Hz, 1H), 6.93-7.14 (m, 4H), 7.21-7.45 (m, 10H), 10.63 (br. s., 1H); $^{13}$C NMR (126 MHz, acetone-de) δ 42.4, 42.7, 47.2, 47.6, 66.1, 115.8, 116.0, 127.8, 127.9, 128.6, 128.7, 129.2, 129.3, 131.2, 131.3, 133.1, 140.2, 140.3, 162.4, 164.3, 172.4, 173.0; HRMS (ESI) m/z calculated for C$_{25}$H$_{21}$FO$_4$ (M+H)$^+$: 405.1497, found 405.1502 (Δ=1.3 ppm).

5c: White solid; 15% yield; mp 103-105° C.; $^1$H NMR (500 MHz, acetone-d$_6$) 4.06 (dd, J=10.53, 7.48 Hz, 2H), 4.51 (dd, J=10.38, 7.32 Hz, 2H), 4.66 (d, J=12.36 Hz, 2H), 4.78 (d, J=12.36 Hz, 2H), 6.93-7.17 (m, 8H), 7.20-7.44 (m, 10H); $^{13}$C NMR (126 MHz, acetone-d$_6$) δ 42.5, 47.4, 66.1, 115.8, 116.0, 128.0, 128.6, 129.3, 131.3, 131.3, 133.1, 133.1, 140.0, 162.4, 164.3, 172.2; HRMS (ESI) m/z calcd for C$_{32}$H$_{26}$F$_2$O$_4$H$^+$: 513.1872, found 513.1882 (Δ=2.0 ppm).

4-Bromobenzyl α-2,4-diphenylcyclobutane-1,3-dicarboxylate (3d)

White solid; 44% yield; mp 175-177° C.; $^1$H NMR (500 MHz, acetone-d$_6$) δ 3.92-4.11 (m, 2H), 4.40-4.57 (m, 2H), 4.69 (d, J=12.66 Hz, 1H), 4.78 (d, J=12.66 Hz, 1H), 6.96 (d, J=8.54 Hz, 2H), 7.20-7.29 (m, 2H), 7.32 (t, J=7.48 Hz, 4H), 7.35-7.40 (m, 2H), 7.40-7.49 (m, 4H); $^{13}$C NMR (126 MHz, acetone-d$_6$) δ 42.4, 42.7, 47.2, 47.5, 66.0, 122.3, 127.8, 127.9, 128.6, 128.7, 129.2, 129.3, 131.0, 132.3, 136.4, 140.2, 140.3, 172.4, 173.1; HRMS (ESI) m/z calcd for C$_{25}$H$_{21}$BrO$_4$H$^+$: 465.0696, found 465.0697 (Δ=0.27 ppm).

Di-tetrahydropyran-4-methyl α-2,4-diphenylcyclobutane-1,3-dicarboxylate (5d)

White solid; 21% yield; $^1$H NMR (500 MHz, acetone-d$_6$) δ 0.91-1.10 (m, 4H), 1.16-1.31 (m, 4H), 1.38-1.55 (m, 2H), 3.17 (tt, J=11.71, 2.33 Hz, 4H), 3.58 (d, J=6.41 Hz, 4H), 3.67-3.81 (m, 4H), 3.90-4.08 (m, 2H), 4.48 (dd, J=10.38, 7.32 Hz, 2H), 7.19-7.31 (m, 2H), 7.31-7.46 (m, 8H); $^{13}$C NMR (126 MHz, acetone-d$_6$) δ 35.2, 42.5, 47.7, 67.8, 67.8, 69.4, 127.9, 128.7, 129.3, 140.3, 172.3; HRMS (ESI) m/z calculated for C$_{30}$H$_{36}$O$_6$H$^+$: 493.2585, found 493.2591 (Δ=1.24 ppm).

Biphenyl-2-yl α-2,4-diphenylcyclobutane-1,3-dicarboxylate (3 g)

White solid; 21% yield; mp 195-196° C.; $^1$H NMR (500 MHz, acetone-d$_6$) δ 3.81 (dt, J=11.67, 10.49 Hz, 2H), 4.39 (t, J=10.07 Hz, 1H), 4.68 (t, J=10.68 Hz, 1H), 5.99 (dd, J=8.09, 1.07 Hz, 1H), 7.11-7.19 (m, 3H), 7.20-7.28 (m, 2H), 7.28-7.40 (m, 11H), 7.40-7.46 (m, 2H); $^{13}$C NMR (126 MHz, acetone-d$_6$) δ 42.3, 45.4, 46.8, 47.0, 123.4, 127.1, 127.4, 128.1, 128.4, 129.2, 129.3, 129.6, 129.8, 131.3, 135.8, 138.5, 139.2, 143.2, 148.7, 170.6, 172.9; HRMS (ESI) m/z calcd for C$_{30}$H$_{24}$C$_4$H$^+$: 449.1747, found 449.1754 (Δ=1.55 ppm).

Biphenyl-3-yl α-2,4-Diphenylcyclobutane-1,3-dicarboxylate (3h)

white solid; $^1$H NMR (500 MHz, acetone-d$_6$) δ 4.14 (dd, J=10.8, 7.2 Hz, 1H), 4.29-4.35 (m, 1H), 4.61 (dd, J=10.8, 7.2 Hz, 1H), 4.67 (dd, J=10.8, 7.2 Hz, 1H), 6.53 (t, J=1.9 Hz, 1H), 6.55-6.57 (m, 1H), 7.29 (d, J=7.4 Hz, 1H), 7.33 (d, J=7.9 Hz, 1H), 7.36-7.41 (m, 4H), 7.44-7.55 (m, 9H), 7.59 (d, J=7.5 Hz, 2H).

Di-biphenyl-3-yl α-2,4-diphenylcyclobutane-1,3-dicarboxylate (5e)

White solid; 1H NMR (500 MHz, acetone-d$_6$) δ4.45 (dd, J=10.8, 7.3 Hz, 2H), 4.81 (dd, J=10.6, 7.4 Hz, 2H), 6.53 (m, 2H), 6.54-6.58 (m, 2H), 7.34 (t, J=7.6 Hz, 2H), 7.39 (m, 4H), 7.43-7.55 (m, 14H), 7.65 (d, J=7.6 Hz, 4H).

2'-HO-biphenyl-2-yl α-2,4-diphenylcyclobutane-1,3-dicarboxylate (3j)

2'-TIPSO-biphenyl-2-yl α-2,4-diphenylcyclobutane-1,3-dicarboxylate (3j-i) was made in the same manner of 3a. The crude product was purified by column chromatography on silica gel using ethyl acetate/hexanes (30% to 50%) as eluent to afford 3j-i as white solid (59% yield). The TIPS protecting group of 3j-i was removed by TBAF in THF to give desired product 3j as a white solid (168 mg, 99%). Melting point: 55.0-57.0° C. $^1$H NMR (500 MHz, Acetone) δ 10.67 (s, 1H), 8.21 (s, 1H), 7.48 (d, J=7.4 Hz, 2H), 7.43 (t, J=7.5 Hz, 2H), 7.26 (ddddd, J=17.1, 15.4, 9.2, 6.6, 2.8 Hz, 12H), 7.11 (dd, J=7.5, 1.5 Hz, 1H), 7.03 (d, J=8.1 Hz, 1H), 6.93-6.87 (m, 1H), 6.15 (dd, J=8.0, 1.0 Hz, 1H), 4.51 (dd, J=10.5, 6.8 Hz, 1H), 4.37 (dd, J=10.4, 7.3 Hz, 1H), 4.11 (dd, J=10.5, 6.9 Hz, 1H), 3.99 (dd, J=10.5, 7.3 Hz, 1H). HRMS (ESI) m/z: calcd for C$_{30}$H$_{25}$O$_5$H$^+$, 465.1697, found, 465.1699 (Δ=0.43 ppm).

2,4,5-Tricholrobenzyl α-2,4-diphenylcyclobutane-1,3-dicarboxylate (3k)

White solid; 70% yield; mp 191-193° C.; $^1$H NMR (700 MHz, acetone-d$_6$) δ 4.14 (dd, J=10.7, 7.3 Hz, 1H), 4.38 (dd, J=10.7, 7.1 Hz, 1H), 4.60 (dd, J=10.7, 7.1 Hz, 1H), 4.68 (dd, J=10.7, 7.3 Hz, 1H), 6.03 (s, 1H), 7.27 (t, J=7.4 Hz, 1H), 7.36 (t, J=7.6 Hz, 2H), 7.41 (t, J=7.3 Hz, 1H), 7.48 (dt, J=15.1, 9.8 Hz, 4H), 7.57 (d, J=7.5 Hz, 2H), 7.70 (d, J=7.6 Hz, 1H), 10.75 (s, 1H); $^{13}$C NMR (175 MHz, acetone-d$_6$) δ 171.9, 169.2, 145.9, 139.1, 138.8, 130.9, 130.7, 129.8, 129.0, 128.8, 127.8, 127.5, 127.0, 126.3, 125.0, 46.5, 45.9, 42.0, 41.2; HRMS (ESI) m/z calcd for $C_{24}H_{18}Cl_3O_4H^+$: 475.0265; found, 475.0264 (Δ=0.21 ppm).

(1R,2S)-2-phenylcyclohexyl α-2,4-diphenylcyclobutane-1,3-dicarboxylate (3l)

White solid; 61% yield; mp 192-193° C.; $^1$H NMR (700 MHz, chloroform-d) δ 0.80 (qd, J=12.8, 3.7 Hz, 1H), 1.22-1.39 (m, 2H), 1.47-1.59 (m, 2H), 1.64-1.76 (m, 2H), 1.90 (d, J=13.4 Hz, 1H), 2.57 (td, J=12.3, 3.6 Hz, 1H), 3.65 (ddd, J=19.6, 9.9, 6.1 Hz, 2H), 3.96 (dd, J=10.0, 8.0 Hz, 1H), 4.24-4.32 (m, 1H), 4.69 (td, J=10.8, 4.2 Hz, 1H), 7.00 (d, J=6.9 Hz, 2H), 7.07 (d, J=7.6 Hz, 2H), 7.15 (d, J=7.1 Hz, 2H), 7.20-7.29 (m, 7H), 7.31 (dd, J=15.5, 8.0 Hz, 2H), 10.64 (s, 1H). 13C NMR (175 MHz, chloroform-d) δ 24.7, 25.8, 31.4, 33.7, 40.6, 42.3, 46.1, 47.3, 49.9, 76.9, 126.7, 126.8, 127.1, 127.3, 127.6, 128.5, 128.6, 138.6, 139.2, 143.2, 171.0, 177.7; HRMS (ESI) m/z: calcd for $C_{30}H_{31}O_4H^+$: 455.2217; found, 455.2221 (Δ 0.81 ppm).

Indan-2-yl α-2,4-diphenylcyclobutane-1,3-dicarboxylate (3m)

White solid; 34% yield; $^1$H NMR (500 MHz, acetone-d$_6$) δ 2.05 (dt, J=4.35, 2.25 Hz, 1H), 2.10 (dd, J=17.09, 2.44 Hz, 1H), 2.74 (dd, J=16.94, 2.59 Hz, 1H), 2.87 (dd, J=16.94, 6.26 Hz, 1H), 3.11 (dd, J=17.09, 6.41 Hz, 1H), 3.90 (dd, J=10.68, 6.71 Hz, 1H), 3.97-4.07 (m, 1H), 4.36-4.48 (m, 2H), 5.14-5.21 (m, 1H), 7.05-7.18 (m, 4H), 7.19-7.25 (m, 1H), 7.27-7.37 (m, 7H), 7.40 (d, J=7.32 Hz, 2H); $^{13}$C NMR (126 MHz, acetone-d$_6$) δ 39.8, 40.0, 42.3, 42.6, 46.9, 47.5, 76.0, 125.3, 125.5, 127.3, 127.4, 127.7, 127.9, 128.7, 128.7, 129.1, 129.2, 140.1, 140.4, 141.4, 173.1; HRMS (ESI) m/z calcd for $C_{27}H_{24}O_4H^+$: 413.1747, found 413.1749 (Δ 0.43 ppm).

Quinolin-8-yl α-2,4-diphenylcyclobutane-1,3-dicarboxylate (3n)

White solid; 39% yield; $^1$H NMR (700 MHz, acetone-d$_6$) δ 4.06 (t, J=10.4 Hz, 1H), 4.38 (t, J=10.4 Hz, 1H), 4.64 (t, J=10.4 Hz, 1H), 4.92 (t, J=10.4 Hz, 1H), 6.41 (d, J=7.5 Hz, 1H), 7.37 (t, J=7.4 Hz, 1H), 7.52-7.43 (m, 7H), 7.60 (dd, J=8.3, 4.2 Hz, 1H), 7.65 (dd, J=7.3, 4.3 Hz, 4H), 7.86 (d, J=8.2 Hz, 1H), 8.41 (dd, J=8.2, 1.5 Hz, 1H), 8.94 (dd, J=4.3, 1.5 Hz, 1H), 10.75 (s, 1H).

6-Acetamidonaphth-1-yl α-2,4-diphenylcyclobutane-1,3-dicarboxylate (3o)

$^1$H NMR (500 MHz, acetone-d$_6$) δ 2.13 (s, 3H), 4.15 (dd, J=10.1, 7.4 Hz, 1H), 4.54 (dd, J=10.7, 7.2 Hz, 1H), 4.68 (dd, J=10.7, 7.2 Hz, 1H), 6.33 (d, J=7.5 Hz, 1H), 7.14 (d, J=9.0 Hz, 1H), 7.28 (dd, J=14.9, 7.3 Hz, 2H), 7.36-7.44 (m, 4H), 7.47 (t, J=7.4 Hz, 2H), 7.55 (d, J=7.4 Hz, 2H), 7.62 (t, J=9.0 Hz, 3H), 8.37 (s, 1H), 9.34 (s, 1H).

5-Ethynylnaphth-1-yl α-2,4-diphenylcyclobutane-1,3-dicarboxylate (3p)

White solid; 44% yield; mp 220-221° C.; 1H NMR (500 MHz, acetone-d$_6$) δ 4.06 (s, 1H), 4.11 (dd, J=10.7, 7.2 Hz, 1H), 4.53 (dd, J=10.7, 7.2 Hz, 1H), 4.64 (dd, J=10.7, 7.2 Hz, 1H), 4.68 (dd, J=10.7, 7.2 Hz, 1H), 6.48 (d, J=7.5 Hz, 1H), 7.26 (m, 3H), 7.34 (t, J=7.6 Hz, 2H), 7.42 (m, 4H), 7.51 (d, J=7.5 Hz, 2H), 7.60 (d, J=7.2 Hz, 2H), 7.67 (d, J=6.8 Hz, 1H), 8.11 (d, J=8.4 Hz, 1H), 10.70 (s, 1H). 13C NMR (176 MHz, acetone-d$_6$) δ 41.61, 42.11, 46.41, 46.77, 80.96, 83.68, 118.80, 119.77, 122.72, 123.45, 125.70, 126.49, 126.72, 126.92, 127.46, 127.85, 128.26, 128.27, 128.80, 131.41, 134.15, 139.18, 139.47, 147.18, 170.69, 172.12.

9-Fluorenylmethyl α-2,4-diphenylcyclobutane-1,3-dicarboxylate (3q)

White solid; 35% yield; mp 180-181° C.; 1H NMR (700 MHz, chloroform-d) δ 3.85 (t, J=6.7 Hz, 1H), 4.00 (ddd, J=18.4, 10.8, 7.4 Hz, 2H), 4.08 (d, J=6.6 Hz, 2H), 4.37 (dd, J=10.8, 6.6 Hz, 1H), 4.47 (dd, J=10.8, 7.4 Hz, 1H), 7.25-7.39 (m, 12H), 7.40-7.48 (m, 4H), 7.80 (d, J=7.5 Hz, 2H); 13C NMR (700 MHz, chloroform-d) δ 41.6, 41.8, 46.3, 46.7, 47.2, 66.6, 120.1, 125.0, 125.1, 127.2, 127.4, 127.5, 128.6, 128.7, 138.3, 138.4, 141.3, 141.4, 143.6, 144.1, 171.9, 177.2. HRMS (ESI) m/z: calcd for $C_{32}H_{27}O_4H^+$: 475.1904; found, 475.1907 (Δ=0.63 ppm).

2,2,2-Trifluoroethyl α-2,4-diphenylcyclobutane-1,3-dicarboxylate (3r)

white solid, 51% yield; $^1$H NMR (300 MHz, acetone-d$_6$) δ 7.55-7.16 (m, 10H), 4.64-4.29 (m, 3H), 4.22-3.98 (m, 3H); 13C NMR (101 MHz, Acetone) δ 172.00, 170.31, 138.93, 138.72, 128.35, 128.24, 127.69, 127.46, 127.02, 126.94, 124.64, 121.89, 60.44, 60.08, 59.71, 59.36, 46.24, 46.00, 41.71, 41.36.

Cyclohexyl α-2,4-diphenylcyclobutane-1,3-dicarboxylate (3s)

White solid; 68% yield; 1H NMR (300 MHz, acetone-d$_6$): δ 0.88 (m, 1H), 1.22 (m, 5H), 1.42 (bs, 2H), 1.60 (m, 2H), 3.90-4.05 (m, 2H), 4.45 (m, 3H), 7.24-7.44 (m, 10H); 13C NMR (100 MHz, acetone-d$_6$) δ 23.207, 23.262, 25.081, 30.756, 31.188, 41.501, 41.660, 46.174, 46.789, 72.035, 126.753, 126.776, 127.756, 128.161, 128.184, 139.442, 139.573, 170.866, 172.183; HRMS (ESI) m/z calcd for $C_{24}H_{27}O_4H^+$: 379.1909, found 379.1909 (Δ 0 ppm).

3-[1-(3,6,9-trioxa-dodecanyl)-1,2,3-triazol-4-yl]phenyl α-2,4-diphenylcyclobutane-1,3-dicarboxylate (3t)

To a solution of 3f in THF (8 mL) and water (1.5 mL), was added cupric sulfate pentahydrate, ascorbic acid, and 1-azido-2-(2-(2-ethoxyethoxy)ethoxy)ethane and the reaction mixture was stirred at room temperature overnight. Upon completion, the reaction mixture was diluted with water and extracted thrice with DCM. The crude mixture was purified with flash column on silica gel with 3.5% methanol in DCM as the eluent to give 3t (180 mg, 94% yield) as white solid. mp 93-95° C.; 1H NMR (500 MHz, acetone-d$_6$) δ 1.07 (t, J=7.02 Hz, 6H), 3.39 (q, J=7.02 Hz, 4H), 3.43-3.49 (m, 4H), 3.49-3.55 (m, 4H), 3.55-3.61 (m, 4H), 3.61-3.71 (m, 4H), 3.93 (t, J=5.19 Hz, 4H), 4.06-4.19 (m, 2H), 4.27-4.36 (m, 2H), 4.54-4.72 (m, 8H), 6.28-6.43 (m, 2H), 6.96 (t, J=1.83 Hz, 2H), 7.21-7.32 (m, 4H), 7.33-7.44 (m, 6H), 7.44-7.54 (m, 8H), 7.57 (d, J=7.32 Hz, 4H), 7.69 (d, J=7.93 Hz, 2H), 8.22 (s, 2H); $^{13}$C NMR (126 MHz, acetone-d$_6$) δ 15.6, 42.3, 42.9, 47.0, 47.6, 51.0, 66.8, 70.1, 70.6, 71.2, 71.3, 119.5, 121.7, 122.4, 123.4, 127.8, 128.3, 128.7, 129.0, 129.2, 129.5, 130.4, 133.7, 140.1, 140.2, 146.8, 152.1, 171.3, 173.1; HRMS (ESI) m/z calculated for $C_{34}H_{37}N_3O_7H^+$: 600.2704, found 600.2705 (Δ=0.13 ppm).

1-Naphthyl α-2,4-di(3-methoxy-4-triehthylsiloxy) cyclobutane-1,3-dicarboxylate (4a-i)

White solid; 26% yield; 1H NMR (300 MHz, CDCl3) δ ppm 0.55-0.77 (m, 13H) 0.82-1.05 (m, 18H) 3.75 (s, 3H) 3.70 (s, 3H) 3.96 (dd, J=10.34, 7.36 Hz, 1H) 4.26 (dd, J=10.24, 7.26 Hz, 1H) 4.37-4.61 (m, 2H) 6.40 (d, J=7.45 Hz, 1H) 6.63-6.76 (m, 1H) 6.76-6.95 (m, 5H) 7.14-7.46 (m, 4H) 7.59 (d, J=8.01 Hz, 1H) 7.73 (d, J=8.01 Hz, 1H).

1-Naphthyl α-2,4-di(3-methoxy-4-hydroxy)cyclobutane-1,3-dicarboxylate (4a)

To a solution of 4a-i (56 mg, 0.08 mmoles), in 20:1 tetrahydrofuran: acetic acid (2.0 mL total), was added 1.0 M TBAF in THF (0.27 mmoles) and the reaction mixture was stirred at room temperature for two hours. After completion, the reaction mixture was diluted with ethyl acetate (30 mL), washed thrice with water (15 mL), and dried over anhydrous magnesium sulfate. The crude mixture was purified using flash column chromatography on silica gel with 3% methanol in dichlcromethane as the eluent to give 4a as white solid in 83% yield; $^1$H NMR (400 MHz, acetone-$d_6$) δ ppm 3.79 (s, 3H) 3.89 (s, 3H) 4.02 (dd, J=10.29, 7.53 Hz, 1H) 4.43 (dd, J=10.29, 7.53 Hz, 1H) 4.51-4.67 (m, 2H) 6.66 (d, J=7.53 Hz, 1H) 6.82 (d, J=8.03 Hz, 1H) 6.88-6.99 (m, 2H) 7.04 (br. s., 1H) 7.07-7.15 (m, 2H) 7.20 (s, 1H) 7.34 (d, J=7.78 Hz, 2H) 7.46 (s, 1H) 7.72 (d, J=8.03 Hz, 1H) 7.85 (s, 1H); HRMS (ESI) m/z calculated for $C_{30}H_{26}O_8H^+$: 515.1700, found 515.1743 (Δ=−8.34 ppm).

1-Naphthyl α-2,4-di(2-methoxylphenyl)cyclobutane-1,3-dicarboxylate (4b)

White solid; 35% yield; mp 183.5-185.0° C. 4H NMR (500 MHz, acetone-$d_6$) 3.90 (s, 1H), 4.16-4.21 (dd, J=8.00, 10.50 Hz, 1H), 4.46-4.49 (dd, J=8.00, 10.50 Hz, 1H), 4.85-4.88 (dd, J=8.00, 10.50 Hz, 1H), 4.85-4.88 (dd, J=8.00, 10.50 Hz, 1H), 4.91-4.95 (dd, J=8.00, 10.50 Hz, 1H), 6.45-6.49 (d, J=7.5 Hz, 1H), 7.01-7.04 (m, 2H), 7.07-7.12 (m, 2H), 7.28-7.31 (td, J=4.45, 24 Hz, 1H), 7.33-7.36 (t, J=7.70 Hz, 1H), 7.39-7.41 (m, 3H), 7.47-7.52 (m, 2H), 7.54-7.56 (d, J=7.00 Hz, 1H), 7.72-7.74 (d, J=8.00 Hz, 1H), 7.88-7.89 (d, J=8.00 Hz, 1H). $^{13}$C NMR (125 MHz, chloroform-d) δ 37.33, 37.62, 44.32, 45.46, 55.12, 55.49, 110.32, 110.48, 117.59, 120.74, 125.30, 134.41, 146.62, 157.55, 157.78, 171.30, 177.82. HRMS (ESI) m/z: calcd for $C_{30}H_{27}O_6H^+$, 483.1802; found, 483.1807 (Δ=1.03 ppm).

1-Naphthyl α-2,4-di(2-nitrophenyl)cyclobutane-1,3-dicarboxylate (4c)

White solid; 38% yield; mp 189.0-190.0° C. $^1$H NMR (500 MHz, dmso-$d_6$) δ 4.37 (s, 1H). 4.68 (s, 1H), 4.89 (s, 1H), 5.04 (s, 1H), 7.79 (m, 15H), 13.23 (s, 1H). 13C NMR (125 MHz, dmso-$d_6$) δ 40.3, 40.7, 42.2, 43.0, 118.1, 121.3, 124.5, 125.7, 126.4, 128.0, 129.6, 132.2, 132.4, 133.0, 146.3, 148.9, 171.1, 173.6.

1-Naphthyl α-2,4-di(4-tertbuytldimethylsiyloxylphenyl)cyclobutane-1,3-dicarboxylate (4d-i)

White solid; 64% yield; mp 169-170° C.; $^1$H NMR (300 MHz, acetone-$d_6$) δ 0.24 (s, 6H), 0.27 (s, 6H), 1.01 (s, 9H), 1.04 (s, 9H), 4.04 (m, 1H), 4.45 (m, 1H), 4.60 (m, 2H), 6.50 (d, J=7.50 Hz, 1H), 6.64 (m, 4H), 7.30 (m, 8H), 7.74 (d, J=8.19 Hz, 1H), 7.89 (d, J=8.19 Hz, 1H); 13C NMR (100 MHz, acetone-$d_6$) δ −5.2, −5.1, 17.9, 17.9, 25.2, 40.9, 41.4, 46.9, 47.1, 117.9, 119.7, 120.1, 121.4, 125.2, 125.7, 126.2, 126.3, 127.7, 129.0, 129.4, 132.0, 132.2, 134.5, 146.8, 154.7, 155.1, 170.7, 172.2.

1-Naphthyl α-2,4-di(4-tertbuytldimethylsiyloxylphenyl)cyclobutane-1,3-dicarboxylate (4d)

To a solution of compound 4d-i (94 mg, 0.14 mmol) with THF (10 mL) and acetic acid (0.5 mL) was added 1 M TBAF (0.5 mL) and the reaction mixture was concentrated after completion. The reaction mixture was purified by flash chromatography to give 4d as white solid (48 mg, 76%); mp>230° C.; 1H NMR (300 MHz, acetone-$d_6$) δ 4.00 (dd, J=10.0, 7.5 Hz, 1H), 4.40 (dd, J=10.2, 7.5 Hz, 1H), 4.62-4.51 (m, 2H), 6.61 (d, J=7.5 Hz, 1H), 6.88 (q, J=7.6 Hz, 4H), 7.15 (d, J=8.5 Hz, 1H), 7.49-7.43 (m, 7H), 7.73 (d, J=8.1 Hz, 1H), 7.87 (d, J=8.2 Hz, 1H), 8.30 (s, 1H), 8.49 (s, 1H); 13C NMR (100 MHz, acetone-ds) δ 40.97, 41.40, 47.03, 47.40, 115.06, 115.54, 118.05, 121.56, 125.25, 125.62, 126.14, 126.24, 126.93, 127.56, 128.99, 129.42, 129.99, 130.25, 134.47, 146.95, 156.45, 156.94, 170.85, 172.27.

(1R,2S)-2-Phenylcyclohexyl α-2,4-di(2-methoxylphenyl)cyclobutane-1,3-dicarboxylate (4e)

White solid; 48% yield; mp 163.0-165.0° C. 1H NMR (500 MHz, chloroform-d) δ 0.72 (td, J=12.8, 3.4 Hz, 1H), 1.27 (ddd, J=40.6, 20.3, 8.1 Hz, 2H), 1.39-1.56 (m, 2H), 1.66 (t, J=13.7 Hz, 2H), 1.82 (d, J=13.2 Hz, 1H), 2.51-2.40 (m, 1H), 3.60 (s, 3H), 3.67 (s, 4H), 3.81 (dd, J=10.5, 6.2 Hz, 1H), 3.85-3.93 (m, 1H), 4.39-4.29 (m, 1H), 4.69 (dd, J=10.7, 6.6 Hz, 1H), 6.71 (d, J=8.1 Hz, 1H), 6.76 (d, J=8.1 Hz, 1H), 6.82 (t, J=7.4 Hz, 1H), 6.87 (d, J=6.8 Hz, 1H), 6.94 (t, J=7.4 Hz, 1H), 7.09 (dd, J=16.6, 7.2 Hz, 3H), 7.13-7.24 (m, 5H). $^{13}$C NMR (125 MHz, chloroform-d) δ 24.7, 25.8, 31.4, 37.2, 44.5, 45.8, 54.9, 55.2, 76.0, 110.0, 110.1, 120.2, 126.4, 127.5, 128.0, 143.2, 157.3, 171.6, 178.5. HRMS (ESI) m/z: calcd for $C_{32}H_{35}O_6H^+$, 515.2428, found, 515.2434 (Δ=1.2 ppm).

(1R,2S)-2-Phenylcyclohexyl α-2,4-di(2-chlorophenyl)cyclobutane-1,3-dicarboxyliate (4f)

White solid; 30% yield; 1H NMR (500 MHz, chloroform-d) δ 1.32-1.6 (m, 4H), 1.80 (d, J=12.7 Hz, 1H), 1.85-2.02 (m, 2H), 2.15-2.33 (m, 1H), 2.64-2.81 (m, 1H), 3.52 (t, J=8.4 Hz, 1H), 3.50-3.77 (m, 2H), 4.48 (dd, J=16.4, 9.8 Hz, 1H), 4.75-4.89 (m, 1H), 5.16 (dt, J=17.2, 7.6 Hz, 1H), 6.78-6.96 (m, 2H), 6.99 (t, J=7.5 Hz, 1H), 7.02-7.11 (m, 3H), 7.13-7.31 (m, 7H). $^{13}$C NMR (125 MHz, chloroform-d) δ 24.9, 25.9, 32.2, 41.5, 49.7, 49.9, 126.2, 126.6, 127.5, 127.7, 128.0, 128.5, 129.7, 134.7, 143.0, 171.0. HRMS (ESI) m/z: calcd for $C_{30}H_{29}Cl_2O_4H^+$, 523.1437, found, 523.1443 (Δ=0.10 ppm).

(1R,2S)-2-Phenylcyclohexyl α-2,4-di(2,6-dichlorophenyl)cyclobutane-1,3-dicarboxylate (4g)

White solid; 30% yield; mp 209.0-201.5° C. $^1$H NMR (700 MHz, chloroform-d) δ 1.40 (dd, J=14.4, 11.3 Hz, 1H), 1.44-1.61 (m, 3H), 1.79 (d, J=13.2 Hz, 1H), 1.88 (d, J=10.1 Hz, 1H), 1.97 (d, J=13.4 Hz, 1H), 2.18-2.26 (m, 1H), 2.76 (td, J=12.1, 3.6 Hz, 1H), 4.45-4.52 (m, 1H), 4.70-4.78 (m, 1H), 5.04 (dd, J=11.6, 9.3 Hz, 1H), 5.21 (td, J=10.4, 4.2 Hz, 1H), 5.27 (dd, J=11.8, 8.1 Hz, 1H), 6.95 (t, J=8.0 Hz, 1H), 6.99 (t, J=8.0 Hz, 1H), 7.04 (d, J=8.0 Hz, 2H), 7.12 (d, J=7.5 Hz, 2H), 7.20 (t, J=7.1 Hz, 1H), 7.30-7.25 (m, 5H). $^{13}$C NMR (175 MHz, chloroform-d) δ 25.0, 25.9, 32.1, 42.3, 49.8, 76.7, 126.6, 127.8, 128.1, 128.5, 129.0, 134.1, 134.3, 143.3, 171.5, 177.5. HRMS (ESI) m/z: calcd for $C_{30}H_{27}Cl_4O_4H^+$, 591.0658, found, 591.0661 (Δ=0.50 ppm).

(1R,2S)-2-Phenylcyclohexyl α-2,4-di(2-bromophenyl)cyclobutane-1,3-dicarboxylate (4h)

White solid; 29% yield; mp 136.0-138.0° C.; $^1$H NMR (500 MHz, acetone-$d_6$) δ 1.33-1.44 (m, 1H), 1.44-1.54 (m, 2H), 1.62 (dd, J=12.9, 3.1 Hz, 1H), 1.76 (d, J=12.9 Hz, 1H), 1.86 (dd, J=28.6, 11.6 Hz, 2H), 2.09 (s, 1H), 2.16 (d, J=9.6 Hz, 1H), 2.71 (td, J=12.2, 3.6 Hz, 1H), 3.61 (dd, J=10.1, 7.5 Hz, 1H), 3.74 (dd, J=10.0, 7.6 Hz, 1H), 4.44-4.54 (m, 1H), 4.82 (dd, J=9.6, 7.7 Hz, 1H), 5.10 (td, J=10.2, 4.0 Hz, 1H), 7.01 (dd, J=12.9, 7.1 Hz, 3H), 7.11 (dt, J=15.3, 7.4 Hz, 4H), 7.21 (d, J=3.9 Hz, 4H), 7.34 (d, J=7.7 Hz, 1H), 7.41 (d, J=7.8 Hz, 1H). $^{13}$C NMR (125 MHz, acetone-$d_6$) δ 25.4, 26.5, 32.9, 34.7, 43.4, 50.4, 76.9, 125.7, 125.9, 127.2, 127.9, 128.4, 129.1, 139.0, 144.1, 171.9, 173.2, HRMS (ESI) m/z: calcd for $C_{30}H_{29}Br_2O_4H^+$, 611.0427, found, 611.0424 (Δ=0.49 ppm).

(1R,2S)-2-Phenylcyclohexyl α-2,4-di(2-nitrophenyl)cyclobutane-1,3-dicarboxylate (4i)

White solid; 36% yield; mp 200.0-202.0° C.; 1H NMR (500 MHz, acetone-$d_6$) δ 1.35-1.45 (m, 1H), 1.49 (dd, J=21.7, 11.8 Hz, 2H), 1.64 (dd, J=12.9, 2.9 Hz, 1H), 1.77 (d, J=12.9 Hz, 1H), 1.86 (dd, J=25.5, 11.5 Hz, 2H), 1.96 (s, 1H), 2.70 (td, J=12.2, 3.4 Hz, 1H), 3.73 (dd, J=10.4, 6.0 Hz, 1H), 3.92 (t, J=9.6 Hz, 1H), 4.76 (t, J=9.4 Hz, 1H), 4.85 (dd, J=10.0, 6.0 Hz, 1H), 5.01-5.13 (m, 1H), 7.14 (d, J=7.6 Hz, 2H), 7.20 (d, J=4.1 Hz, 4H), 7.34-7.25 (m, 2H), 7.37 (t, J=7.4 Hz, 2H), 7.52 (t, J=7.5 Hz, 1H), 7.68 (d, J=7.8 Hz, 1H), 7.72 (d, J=8.0 Hz, 1H). 13C NMR (125 MHz, acetone-$d_6$) δ 25.4, 26.5, 32.8, 34.4, 40.9, 50.5, 77.3, 125.2, 125.5, 127.2, 128.5, 128.8, 129.1, 130.1, 130.2, 134.0, 144.0, 149.7, 151.0, 171.4, HRMS (ESI-TOF) (m/z): calcd for $C_{30}H_{29}N_2O_8H^+$, 545.1918, found, 545.1921 (Δ=0.55 ppm).

9-Fluorenylmethyl α-2, 4-di(2-methoxyphenyl)cyclobutane-1,3-dicarboxylate (4j)

White solid; 70% yield; mp 160.0-162.0° C.; $^1$H NMR (500 MHz, chloroform-d) δ 3.76 (d, J=11.6 Hz, 4H), 3.80 (s, 3H), 3.96 (dd, J=10.6, 8.0 Hz, 1H), 4.06 (dd, J=10.4, 7.8 Hz, 1H), 4.17-4.10 (m, 2H), 4.66 (dd, J=10.5, 7.1 Hz, 1H), 4.72 (dd, J=10.4, 7.8 Hz, 1H), 6.82 (d, J=8.1 Hz, 1H), 6.86 (d, J=8.1 Hz, 1H), 7.00 (q, J=7.1 Hz, 2H), 7.24 (t, J=7.2 Hz, 1H), 7.36-7.27 (m, 5H), 7.41 (t, J=6.9 Hz, 3H), 7.51 (d, J=7.5 Hz, 1H), 7.77 (d, J=7.5 Hz, 2H). 13C NMR (125 MHz, chloroform-d) δ 37.1, 37.7, 44.6, 46.9, 55.2, 55.3, 66.4, 110.1, 110.3, 120.0, 125.1, 127.1, 127.7, 141.2, 141.3144.0, 144.4, 157.5, 157.6, 172.6, 178.6. HRMS (ESI) m/z: calcd for $C_{34}H_{31}O_6H^+$, 538.2208; found, 538.2228 (Δ=3.72 ppm).

9-Fluorenylmethyl α-2, 4-di(2-chlorophenyl)cyclobutane-1,3-dicarboxylate (4k)

White solid; 55% yield; mp 186.5-187.5° C. $^1$H NMR (500 MHz, DMSO-$d_6$), δ 4.01 (dd, J=9.7, 7.0 Hz, 1H), 4.10-4.20 (m, 1H), 4.23 (t, J=7.0 Hz, 1H), 4.38 (p, J=10.6 Hz, 2H), 4.60-4.70 (m, 1H), 4.70-4.82 (m, 1H), 7.04-7.20 (m, 4H), 7.26 (dt, J=24.3, 8.7 Hz, 4H), 7.34 (d, J=6.2 Hz, 1H), 7.37-7.46 (m, 3H), 7.62 (t, J=7.5 Hz, 2H), 7.87 (dd, J=7.1, 3.2 Hz, 2H), 12.74 (s, 1H). $^{13}$C NMR (125 MHz, DMSO-$d_6$) δ 41.2, 41.6, 42.5, 46.2, 66.2, 120.2, 125.2, 133.5, 140.7, 143.4, 143.6, 172.1, 173.7. HRMS (ESI) m/z: calcd for $C_{32}H_{25}Cl_2O_4H^+$, 543.1124, found, 543.1123 (Δ=0.18 ppm).

As Scheme 1 shows, the general procedure for the synthesis of α-truxillic acid mono-esters 3 commenced with the photochemical reaction of trans-cinnamic acid through irradiation in solid state at 360 nm for 3-5 days, depending on the scale. This reaction proceeded through head-to-tail [2+2] cycloaddition to give α-truxillic acid (1a) in 93-95% yield. Reaction of 1a with thionyl chloride in the presence of a catalytic amount of dimethylformamide (DMF) under reflux afforded α-truxillic dichloride (2a), which was used directly to the subsequent reactions.

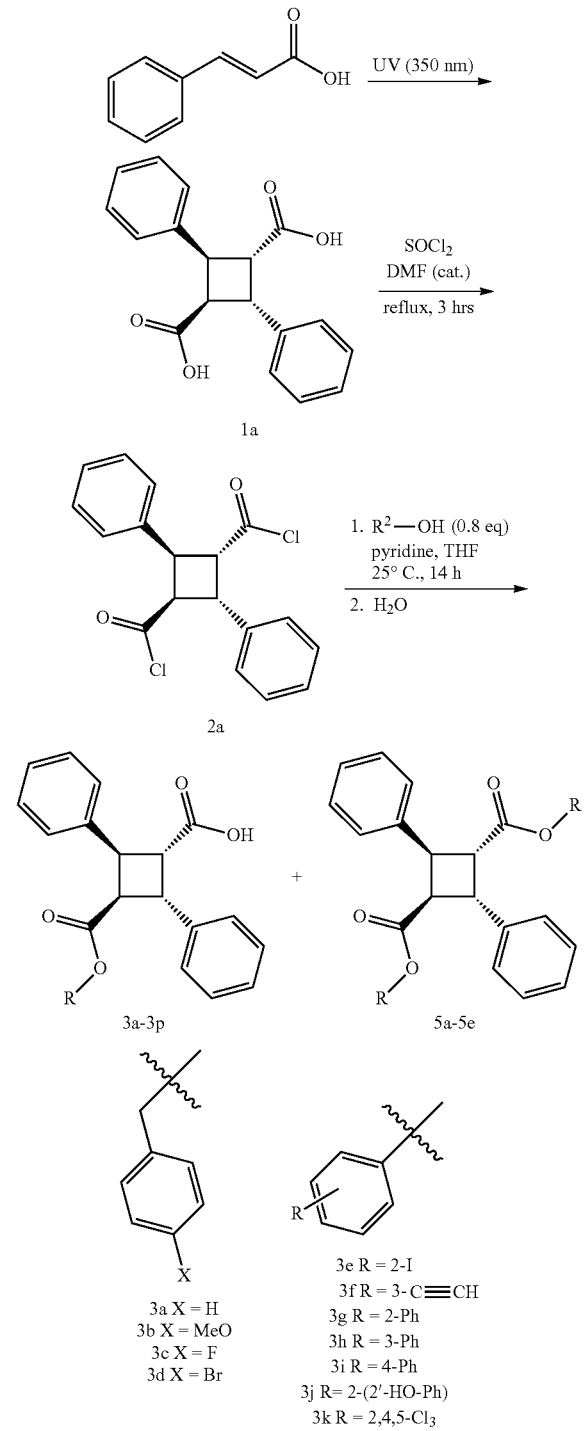

Scheme 1. Synthesis of α-truxillic acid mono-esters (3)

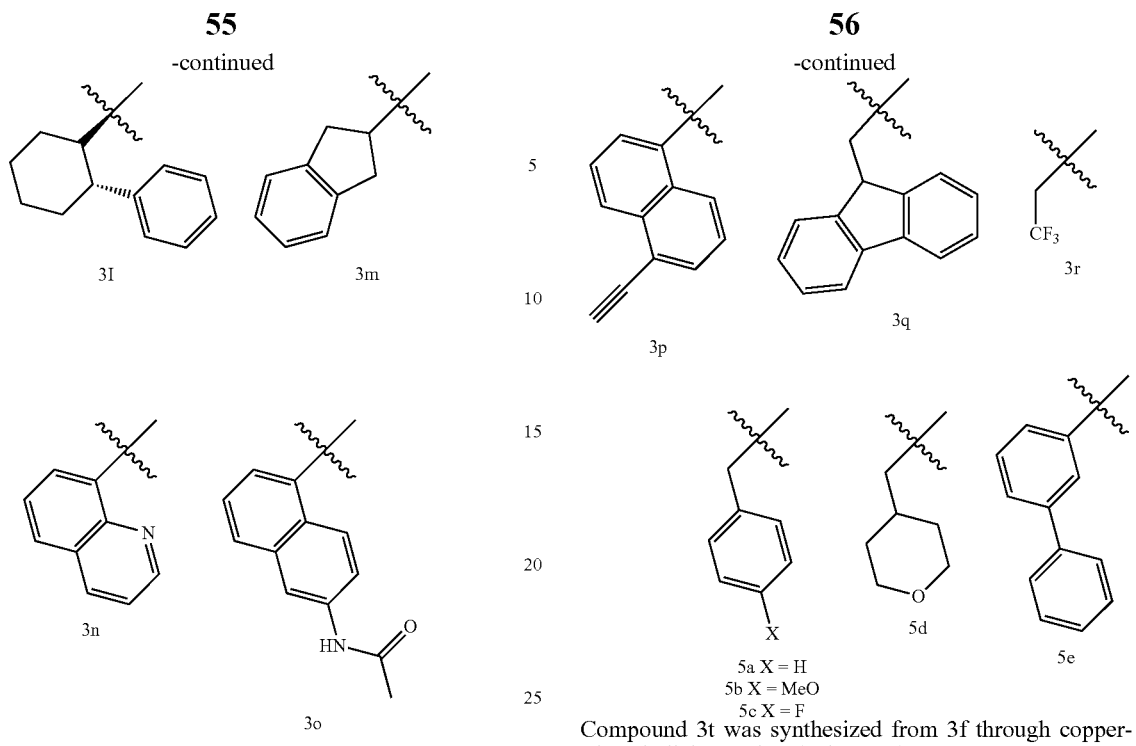
Compound 3t was synthesized from 3f through copper-catalyzed click reaction (Scheme 2).
Scheme 2. Synthesis of 3t.
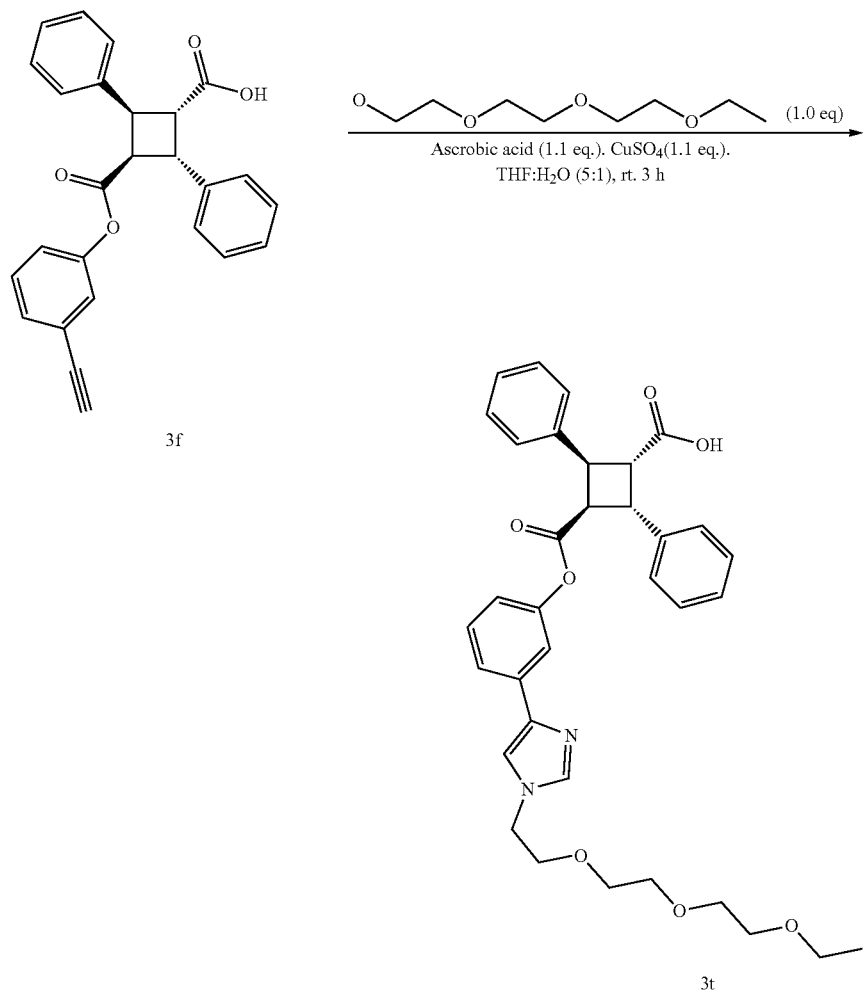

A series of α-truxillic acid mono-esters bearing substituents in the phenyl moieties 4 was synthesized in the same manner as that for 3 from the corresponding substituted trans-cinnamic acids as shown in Scheme 3.

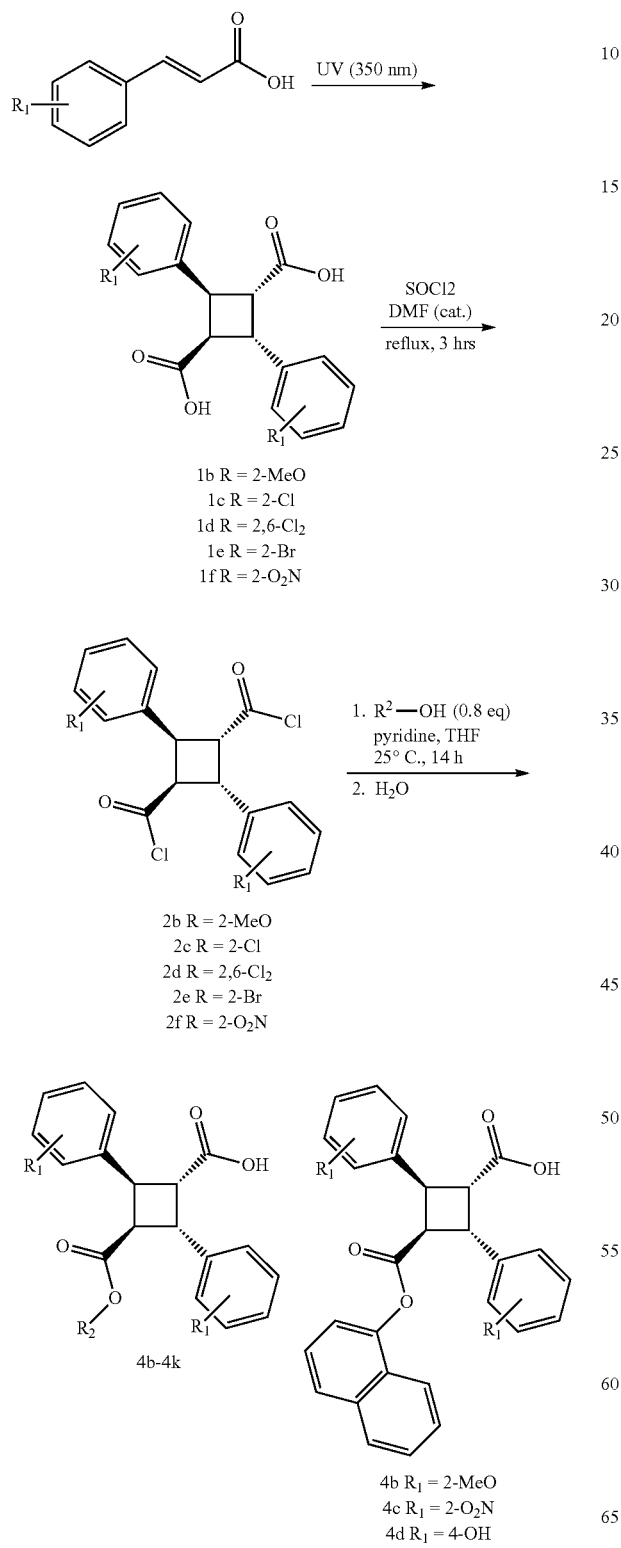

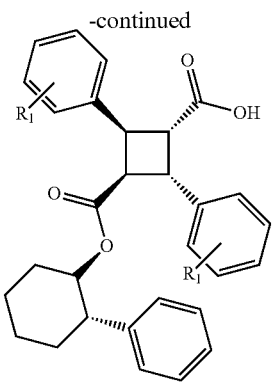

4e R₁ = 2-MeO
4f R₁ = 2-Cl
4g R₁ = 2,6-Cl₂
4h R₁ = 2-Br
4i R₁ = 2-NO₂

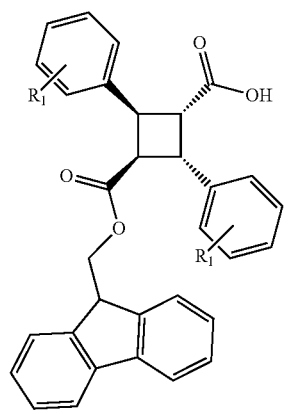

4j R₁ = 2-MeO
4k R₁ = 2-Cl

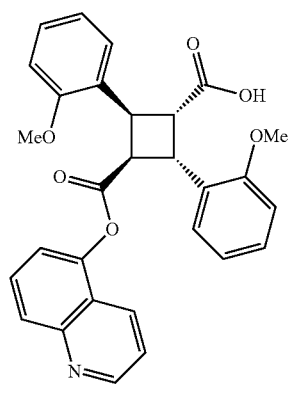

4l

Compound 4a was synthesized from commercially available 4-hydroxy-3-methoxycinnamic acid with modification in the mono-esterification step, where water-soluble carbodiimide, EDC.HCl, was used as the condensation reagent (Scheme 4).

Scheme 4. Synthesis of 4a.

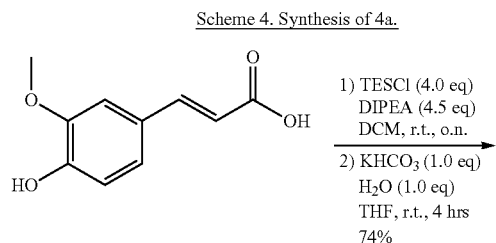

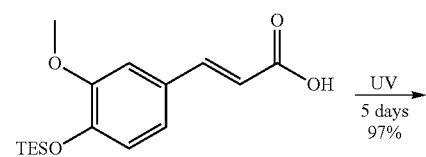

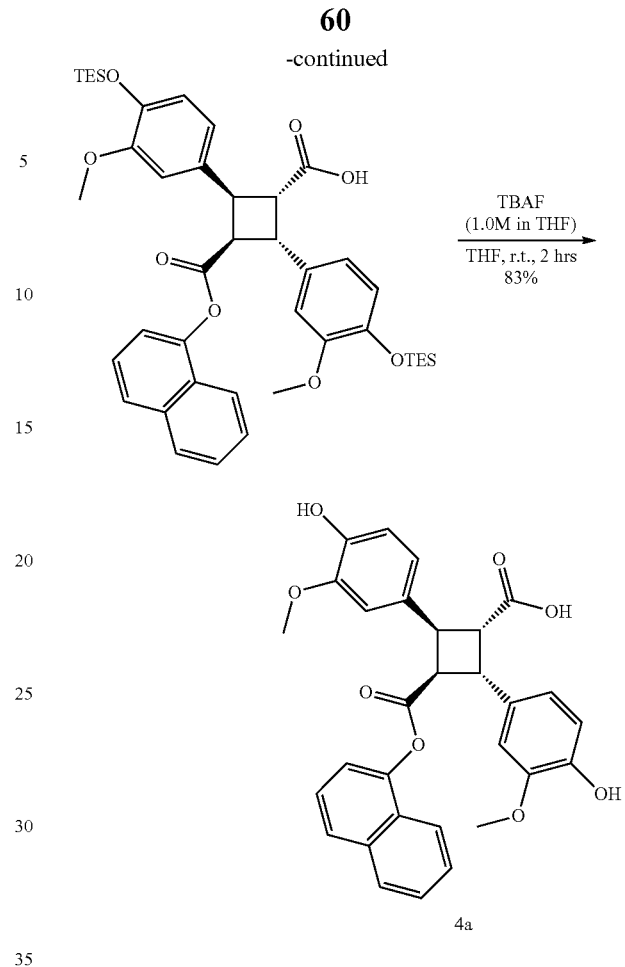

Compound 31 (racemic) was found to have a binding affinity to FABP5 better than 3A by a factor of 4-5. However, 31 has four possible stereoisomers due to the chiral center in its ester moiety as well as α-truxllic acid moiety. Therefore, isolation of these four stereoisomers of 31 was attempted by using two pure enantiopures of 2-phenyl-1-cyclohexanol and fractional recrystallization. This efforts led to the successful isolations of two pure stereoisomers 31-A and 31-B, bearing (1R,2S)-2-phenylcyclohex-1-yl and (1S,2R)-2-phenylcyclohex-1-yl groups, respectively. Also, a diasteremer mixture of 31-A and 31-C, as well as 31-B and 31-D, was obtained and all those samples were subjected to the fluorescence displacement assays. Interestingly, all these four samples showed the same binding affinity to FABP5 within the standard diviation. The procedures for the synthesis of 31 stereoisomers is illustrated in Scheme 5 and the structures of each diastereomer are recited in Scheme 6.

Scheme 5. Synthesis of 31.

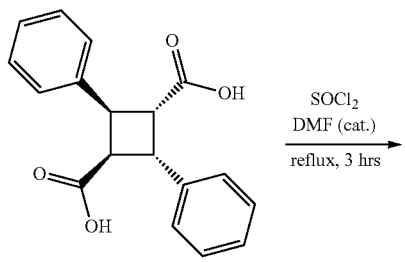

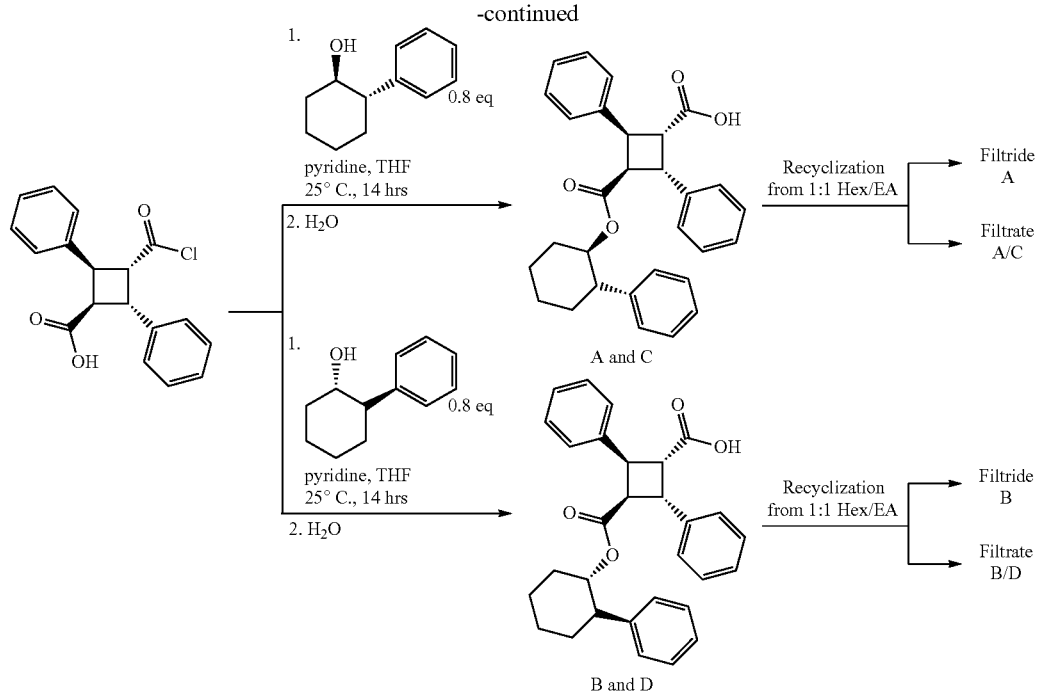
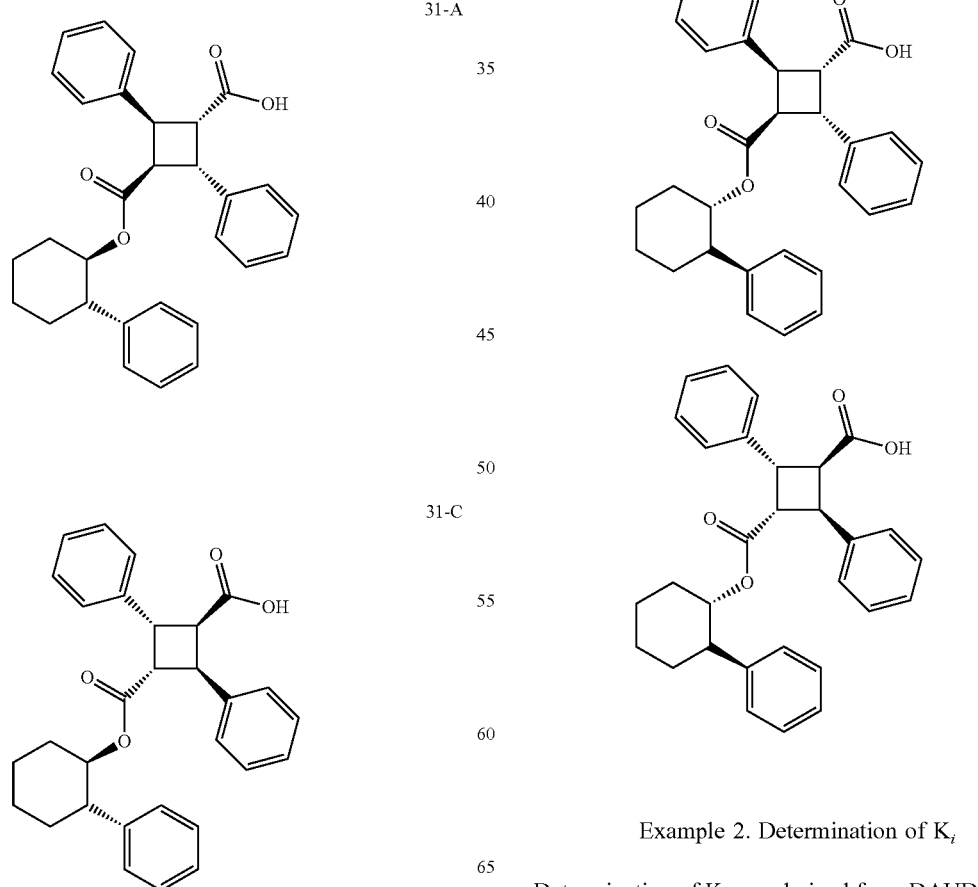
Scheme 6. Structures of each diastereomer 31-A to 31-D.
Example 2. Determination of $K_i$
Determination of $K_i$ was derived from DAUDA or NBD-stearate displacement assays (see Table 1).

TABLE 1

In vitro affinities (K_i) of FABP inhibitors (1: unsubstituted and substituted α-truxillic acid; 3: α-truxillic acid mono ester; 4: substituted α-truxillic acid mono ester)

| Compound | FABP3 Ki | FABP5 Ki | FABP7 Ki |
|---|---|---|---|
| 3 | 2.70 ± 0.42 μM | 0.81 ± 0.09 μM | 0.45 ± 0.07 μM |
| 3-A | 3.26 ± 0.70 μM | 0.78 ± 0.14 μM | 0.89 ± 0.24 μM |
| 3-B | 2.82 ± 0.10 μM | 0.80 ± 0.14 μM | 0.66 ± 0.16 μM |
| 3a | >10 μM | 3.81 ± 0.53 μM | 0.53 ± 0.12 μM |
| 3b | >10 μM | 2.15 ± 0.10 μM | 1.14 ± 0.06 μM |
| 3c | >10 μM | 2.42 ± 0.18 μM | 1.65 ± 0.21 μM |
| 3d | >10 μM | 1.58 ± 0.16 μM | 1.25 ± 0.03 μM |
| 3e | 1.18 ± 0.10 μM | 1.34 ± 0.21 μM | 0.94 ± 0.34 μM |
| 3f | >10 μM | 0.89 ± 0.15 μM | 0.78 ± 0.12 μM |
| 3g | 0.70 ± 0.42 μM | 0.77 ± 0.08 μM | 0.35 ± 0.12 μM |
| 3h | 9.75 ± 0.79 μM | 0.85 ± 0.22 μM | 0.74 ± 0.17 μM |
| 3i | 3.93 ± 0.16 μM | 2.52 ± 0.36 μM | 2.27 ± 0.03 μM |
| 3j | 3.52 ± 0.53 μM | 1.59 ± 0.43 μM | 0.54 ± 0.18 μM |
| 3k | 2.98 ± 0.85 μM | 0.80 ± 0.11 μM | 0.54 ± 0.02 μM |
| 3l | 1.08 ± 0.37 μM | 0.21 ± 0.02 μM | 0.40 ± 0.03 μM |
| 3l-A | — | 0.20 ± 0.03 μM | — |
| 3l-B | — | 0.18 ± 0.03 μM | — |
| 3l-C | — | 0.21 ± 0.02 μM | — |
| 3l-D | — | 0.18 ± 0.01 μM | — |
| 3m | >10 μM | 1.57 ± 0.15 μM | 2.41 ± 0.09 μM |
| 3o | 2.82 ± 0.18 μM | 0.97 ± 0.18 μM | 1.12 ± 0.45 μM |
| 3p | 4.94 ± 0.31 μM | 3.92 ± 0.75 μM | 1.03 ± 0.22 μM |
| 3q | >10 μM | 2.56 ± 0.16 μM | 2.70 ± 0.62 μM |
| 3r | >10 μM | >10 μM | 1.59 ± 0.24 μM |
| 3s | >10 μM | 2.17 ± 0.32 μM | 0.50 ± 0.11 μM |
| 3t | >10 μM | >10 μM | 1.06 ± 0.07 μM |
| 4a | 1.06 ± 0.19 μM | >10 μM | 2.12 ± 0.19 μM |
| 4b | 0.69 ± 0.17 μM | 0.55 ± 0.05 μM | 0.67 ± 0.04 μM |
| 4d | 2.30 ± 0.47 | >10 μM | 1.06 ± 0.34 |
| 4e | 0.40 ± 0.08 μM | 0.68 ± 0.06 μM | 0.40 ± 0.03 μM |
| 4f | >10 μM | 1.70 ± 0.33 μM | >10 μM |
| 4g | >10 μM | 1.23 ± 0.18 μM | 6.32 ± 0.96 μM |
| 4h | >10 μM | 2.76 ± 0.16 μM | >10 μM |
| 4j | >10 μM | 1.72 ± 0.12 μM | >10 μM |
| 4k | >10 μM | 0.89 ± 0.05 μM | 3.54 ± 0.77 μM |

*All values derived from DAUDA, ANS, or NBD-stearate fluorescence binding assays. Ki values represent an average ± S.E. of at least three independent experiments.

The compounds of Table 1 display unexpected selectivity toward FABP3, FABP 5 or FABP 7. Compounds contained herein are selective for one of FABP3, FABP5 or FABP7, or are selective for both FABP5 and FABP7, but not for FABP3.

Example 3. AEA Uptake in Cells

It was previously shown that FABPs are intracellular carriers that shuttle endocannabinoids and related N-acylethanolamines to intracellular sites, such as FAAH for hydrolysis (Kaczocha, M. et al. 2209; Kaczocha, M. et al. 2012). Pharmacological or genetic inhibition of FABPs reduces AEA catabolism in cells, confirming an essential role for these proteins in endocannabinoid inactivation. Therefore, it is examined as to whether the present FABP inhibitors reduce FABP-mediated AEA uptake in cells.

Compounds shown in Table 1 inhibit cellular AEA accumulation and fail to reduce AEA uptake in cells bearing a knockdown of FABP5, the main FABP expressed in HeLa cells. Additionally, the compounds fail to inhibit FAAH. Accordingly, compounds shown in Table 1 selectively inhibit FABP.

Example 4. Antinociceptive and Anti-Inflammatory Effects in Mice

Similar to cannabinoid receptor agonists, inhibitors of endocannabinoid inactivation produce antinociceptive and antinociceptive effects (Cravatt, B. F. et al. 2001; Lichtman, A. H. 1990). Importantly, FAAH inhibitors lack the untoward psychotropic effects of cannabinoid receptor agonists (Cravatt, B. F. et al. 2004), highlighting the therapeutic advantage of pharmacologically targeting endocannabinoid inactivation. Because inhibition of AEA transport to FAAH reduces AEA inactivation, we hypothesized that FABP inhibitors may likewise possess antinociceptive and anti-inflammatory properties. The present compounds are examined using two nociceptive models: the formalin test and carrageenan-induced thermal hyperalgesia.

In the formalin test, injection of formalin results in the induction of two temporally distinct phases of pain with the first phase (0-5 min) representing nociceptor activation and the second phase (15-45 min) representing inflammatory pain and central sensitization. Compounds 4-listed in Table 1 reduce nocifensive behavior during the first phase of the formalin test.

The present compounds alleviate inflammatory pain induced by intraplantar injection of λ-carrageenan. Compounds listed in Table 1 (20 mg/kg, i.p. is used) reduce carrageenan-induced thermal hyperalgesia and paw edema.

Example 5. Additional In Vivo Mouse Studies and Pharmacokinetic Data

Compound listed in Table 1 are administered by a single injection and plasma and brain concentrations were analyzed over 24 hours. Compounds shown in Table 1 also reduce the first and second phases of formalin-induced nociception in mice. Compounds listed in Table 1 reduce acetic acid-induced writhing in mice. Compounds listed in Table 1 also elevate brain levels of the endocannabinoid anandamide (AEA).

Example 6. Optical Resolution of α-Truxillic Acid Monoesters

As shown below (Scheme 7), starting from a racemic mixture, high enantiomeric excess of each of the two enantiomers of compound 17 can be achieved by chiral resolution via recrystallization.

Scheme 7.

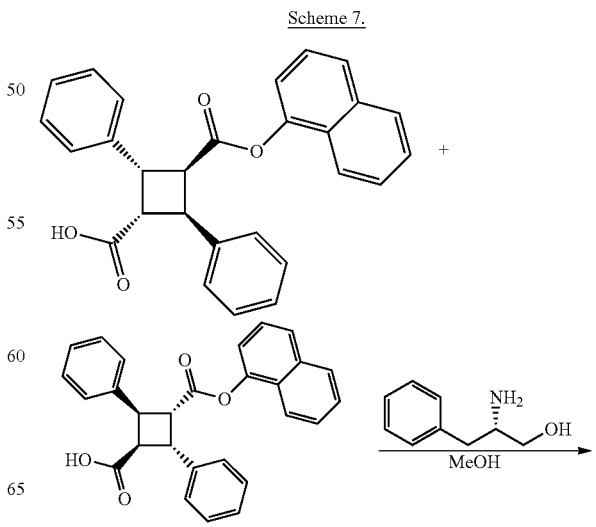

65
-continued
66
-continued
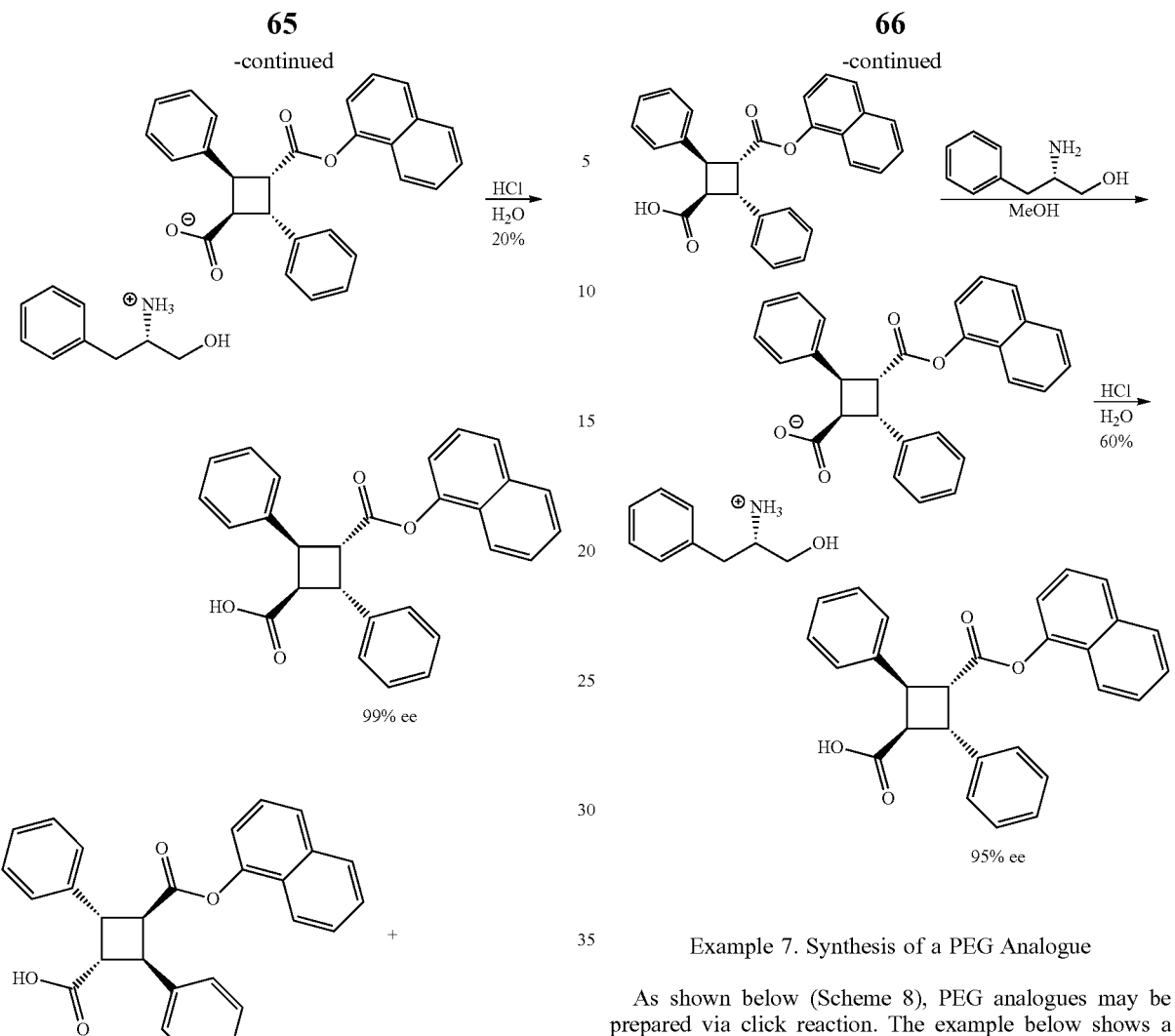
Example 7. Synthesis of a PEG Analogue
As shown below (Scheme 8), PEG analogues may be prepared via click reaction. The example below shows a PEG analogue which was prepared from a PEG-azide and an alkyne-containing α-Truxillic Acid Monoester.
Scheme 8.
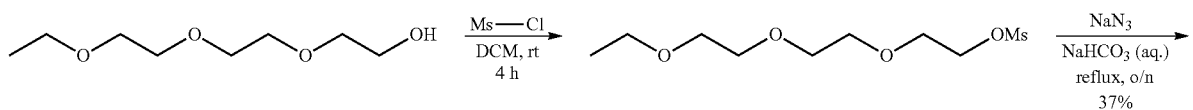
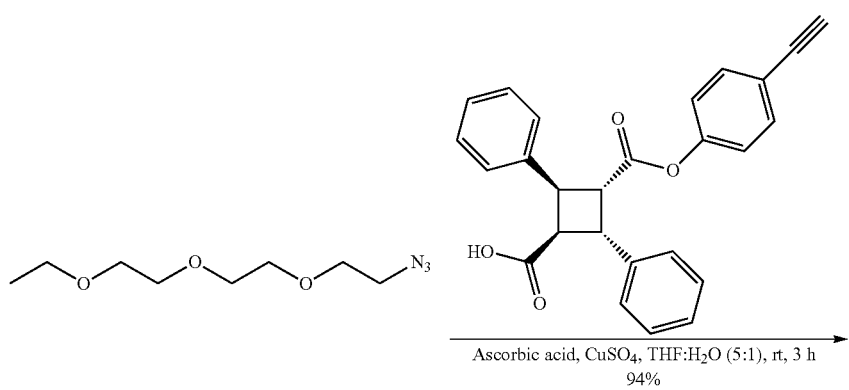

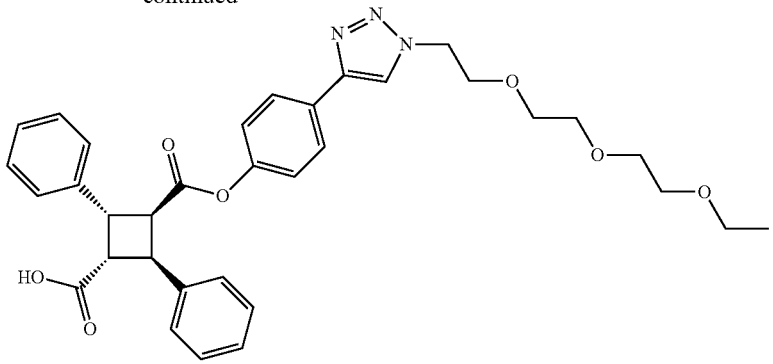

Discussion

The design of truxillic acid based compounds targeting early stage (neurogenic pain response) and late stage (inflammatory pain response) has coincidently been studied recently based on the structure of the natural product (−)-incarvillateine. This natural product was first isolated from the plant species *Incarvillea sinensis*, which has been known in traditional Chinese medicine to treat rheumatism and pain. Interestingly, the isolated (−)-incarvillateine was found to possess antinociceptive properties on the same level as morphine.

Recently research (Chi, Y. et al. 2005) was carried out to identify potential leads for commercialization purposes focusing on di-esters and di-carboxylic acid derivatives. Despite the lack of target identification, α and β-truxillic acid di-ester and di-carboxylic acid derivatives were designed, synthesized and tested against early and late stage pain in formalin induced mouse models to study the effects of each analogue in-vivo. The results of the SAR study clearly showed that α-truxillic acid alone provided the best antinociceptive agent in both early and late stage pain. Although the para-hydroxyl functionalization on the phenyl rings slightly improved late stage pain relief it drastically reduced early stage pain relief.

As described herein, α-2,4-diphenyl-cyclobutane-1,3-dicarboxylic acid mono-esters are reversible inhibitors of FABPs. These compounds bind to FABPs and block the shuttling of endocannabinoids within the cell and thereby increase the endogenous levels of the endocannabinoid anandamide by circumventing degradation by FAAH. Increased levels of anandamide result in the activation of the CB1 pathway leading to antinociceptive pain relief and reduction of inflammation which is shown in a formalin induced mouse model (in-vivo results).

REFERENCES

Ahn, K. et al. (2009) Discovery and characterization of a highly selective FAAH inhibitor 1bat reduces inflammatory pain. Chem Biol 16, 411-420.

Barf, T., Lehmann, F., Hammer, K., Haile, S., Axen, E., Medina, C., Uppenberg, J., Svensson, S., Rondahl, L., and Lundback, T. (2009) N-Benzyl-indolocarboxylic acids: Design and synthesis of potent and selective adipocyte fatty-acid binding protein (A-F ABP) inhibitors. Bioorg Med Chem Lett, 19, 1745-1748.

Chi, Y. M., Nakamura, M., Yoshizawa, T., Zhao, X. Y., Yan, W. M., Hashimoto, F., Kinjo, J., Nohara, T., and Sakurada, S. (2005) Anti-inflammatory activities of alpha-truxillic acid derivatives and their monomer components. Biol Pharm Bull 28, 1776-1778.

Chi, Y. M., Nakamura, M., Zhao, X. Y., Yoshizawa, T., Yan, W. M., Hashimoto, F., Kinjo, 1, Nohara, T., and Sakurada, S. (2006) Antinociceptive activities of alpha-truxillic acid and beta-truxinic acid derivatives. Biol Pharm Bull 29, 580-584.

Chmurzynska, A. et al. (2006) Chmurzynska A (2006) The multigene family of fatty acid-binding proteins (FABPs): function, structure and polymorphism. J Appl Genet 47, 39-48.

Cravatt B F, Demarest K, Patricelli M P, Bracey M H, Giang D K, et al. (2001) Supersensitivity to anandamide and enhanced endogenous cannabinoid signaling in mice lacking fatty acid amide hydrolase. Proceedings of the National Academy of Sciences of the United States of America 98: 9371-9376.

Cravatt B F, Lichtman A H (2004) The endogenous cannabinoid system and its role in nociceptive behavior. Journal of neurobiology 61, 149-160.

Furuhashi, M. and Hotamisligil, G. S. (2008) Fatty acid-binding proteins: role in metabolic diseases and potential as drug targets. Nat Rev Drug Discov 7, 489-503.

Howlett, A. C., Reggio, P. H., Childers, S. R., Hampson, R. E., Ulloa, N. M., and Deutsch, D. G. (2011) Endocannabinoid tone versus constitutive activity of cannabinoid receptors. Br J Pharmacol 163, 1329-1343.

Kaczocha, M., Glaser, S. T., and Deutsch, D. G. (2009) Identification of intracellular carriers for the endocannabinoid anandamide. Proc Natl Acad Sci USA 106, 6375-6380.

Kaczocha, M., Vivieca, S., Sun, J., Glaser, S. T., and Deutsch, D. G. (2012) Fatty Acid-binding Proteins Transport N-Acylethanolamines to Nuclear Receptors and Are Targets of Endocannabinoid Transport Inhibitors. J Biol Chem 287, 3415-3424.

Lichtman A H, Martin B R (1990) Spinal action of cannabinoid-induced antinociception. NIDA Res Monogr 105: 422-424.

Nakamura M, Chi Y M, Yan W M, Nakasugi Y, Yoshizawa T, et al. (1999) Strong Antinociceptive Effect of Incarvillateine, a Novel Monoterpene Alkaloid from Incarvillea sinensis. J Nat Prod 62: 1293-1294.

Shoichet B K (2004) Virtual screening of chemical libraries. Nature 432: 862-865.

Sulsky, R. et al. (2007) Potent and selective biphenyl azole inhibitors of adipocyte fatty acid binding protein (aF-ABP). Bioorg Med Chem Lett 17, 3511-3515.

What is claimed is:

1. A method of inhibiting the activity of a Fatty Acid Binding Protein (FABP) comprising contacting the FABP with a compound having the structure:

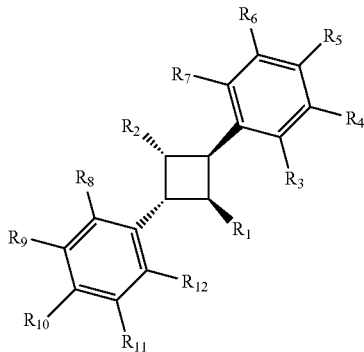

wherein one of $R_1$ or $R_2$ is —C(=O)OH and the other of $R_1$ or $R_2$ is —C(=O)$OR_{13}$ or —C(=O)O-alkyl-$R_{14}$, wherein $R_{13}$ is cycloalkyl, aryl or heteroaryl, and $R_{14}$ is $CF_3$, cycloalkyl, cycloheteroalkyl, aryl or heteroaryl; and $R_3$, $R_4$, $R_5$, $R_6$, Ry, $R_8$, $R_9$, $R_{10}$, $R_{11}$ and $R_{12}$ are each independently, H—$OR_{15}$ or halogen wherein $R_{15}$ is H, $C_{1-10}$ alkyl, $C_{2-10}$ alkenyl, $C_{2-10}$ alkynyl, aryl, or heteroaryl, wherein when one of $R_1$ or $R_2$ is —C(=O)OH and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)$OR_{13}$ where $R_{13}$ is 1-naphthyl or 2-naphthyl or —C(=O)O-alkyl-$R_{14}$ where the alkyl is a branched $C_2$ alkyl and the $R_{14}$ is phenyl, or an enantiomer or racemate thereof;

or a pharmaceutically acceptable salt thereof.

2. The method of claim 1, wherein the compound has the structure

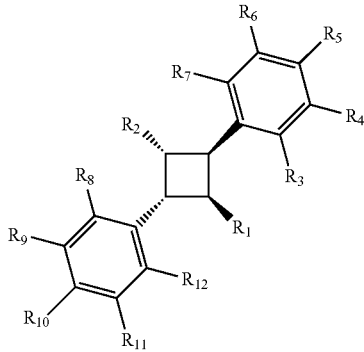

wherein one of $R_1$ or $R_2$ is —C(=O)OH and the other of $R_1$ or $R_2$ is —C(=O)$OR_{13}$ or —C(=O) O-alkyl-$R_{14}$, wherein $R_{13}$ is cycloalkyl, aryl or heteroaryl, and $R_{14}$ is $CF_3$, cycloalkyl, aryl or heteroaryl; and $R_3$, $R_4$, $R_5$, $R_6$, $R_7$, $R_8$, $R_9$, $R_{10}$, $R_{11}$ and $R_{12}$ are each independently, H—$OR_{15}$ or halogen wherein $R_{15}$ is H, $C_{1-10}$ alkyl, $C_{2-10}$ alkenyl, $C_{2-10}$ alkynyl, aryl, or heteroaryl, wherein when one of $R_1$ or $R_2$ is —C(=O)OH and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)$OR_{13}$ where $R_{13}$ is 1-naphthyl or 2-naphthyl, or —C(=O)O-alkyl-$R_{14}$ where the alkyl is a branched $C_2$ alkyl and the $R_{14}$ is phenyl, or is an enantiomer or racemate thereof;

or is a pharmaceutically acceptable salt thereof.

3. The method of claim 1, wherein when one of $R_1$ or $R_2$ of the compound is —C(=O)OH and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)$OR_{13}$ where $R_{13}$ is tolyl, 1-naphthyl or 2-naphthyl, or —C(=O)O-alkyl-$R_{14}$ where the alkyl is a branched $C_2$ alkyl and the $R_{14}$ is phenyl.

4. The method of claim 1, wherein when one of $R_1$ or $R_2$ of the compound is —C(=O)OH and the other of $R_1$ or $R_2$ is —C(=O)$OR_{13}$ where $R_{13}$ is 1-naphthyl or 2-naphthyl, then one, two, or four of $R_3$, $R_4$, $R_5$, $R_6$, $R_7$, $R_8$, $R_9$, $R_{10}$, $R_{11}$ and $R_{12}$ is other than —H.

5. The method of claim 1, wherein (a) one of $R_1$ or $R_2$ of the compound is —C(=O)$R_{13}$, wherein $R_{13}$ is cycloalkyl, aryl or heteroaryl; and the other of $R_1$ or $R_2$ is —C(=O)OH;

(b) one of $R_1$ or $R_2$ of the compound is —C(=O)O-alkyl-$R_{14}$, wherein $R_{14}$ is $CF_3$, cycloalkyl, aryl or heteroaryl; and the other of $R_1$ or $R_2$ is —C(=O)OH;

(c) one of $R_1$ or $R_2$ of the compound is —C(=O)O—($C_{1-6}$ alkyl)-$R_{14}$, wherein $R_{14}$ is $CF_3$, cycloalkyl, aryl or heteroaryl; and the other of $R_1$ or $R_2$ is —C(=O)OH; or (d) one of $R_1$ or $R_2$ of the compound is —C(=O)O—$CH_3$—$R_{14}$, wherein $R_{14}$ is $CF_3$, cycloalkyl, aryl or heteroaryl; and the other of $R_1$ or $R_2$ is —C(=O)OH.

6. The method of claim 1, wherein the aryl of the compound is a substituted aryl.

7. The method of claim 6, wherein the aryl of the compound is substituted with a halogen, —OH, heteroaryl, $C_2$-$C_6$ alkynyl or —O(alkyl), amide, aryl, hydroxyaryl, F, Cl, Br, —OH, I, —NHC(O)$CH_3$, triazolyl, $C_2$ alkylnyl, phenyl, o-hydroxyphenyl or —$OCH_3$.

8. The method of claim 1, wherein the heteroaryl of the compound is a substituted heteroaryl.

9. The method of claim 8, wherein the heteroaryl is substituted with a halogen, —OH, heteroaryl, $C_2$-$C_6$ alkynyl or —O(alkyl), amide, aryl or hydroxyaryl, F, Cl, Br, —OH, I, —NHC(O)$CH_3$, triazolyl, $C_2$ alkylnyl, phenyl, o-hydroxyphenyl or —$OCH_3$.

10. The method of claim 1, wherein the cycloalkyl of the compound is a substituted cycloalkyl.

11. The method of claim 10, wherein the cycloalkyl of the compound is substituted with a phenyl or a fused benzo group.

12. The method of claim 1, wherein the cycloalkyl of the compound is:
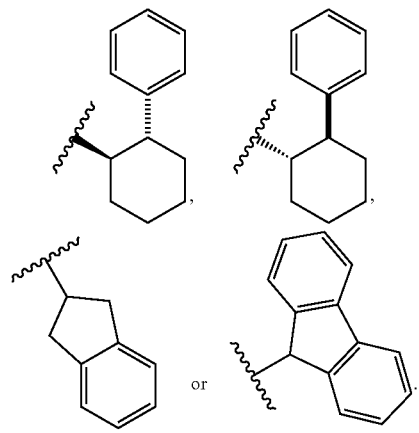
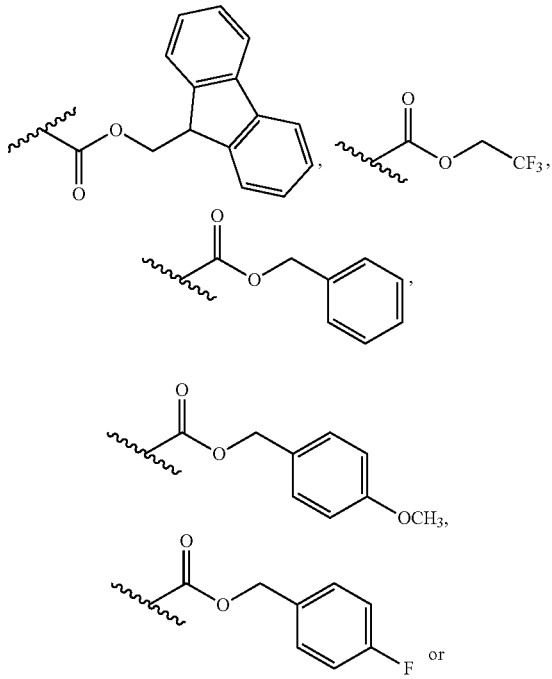
13. The method of claim 1, wherein one of $R_1$ or $R_2$ of the compound is:
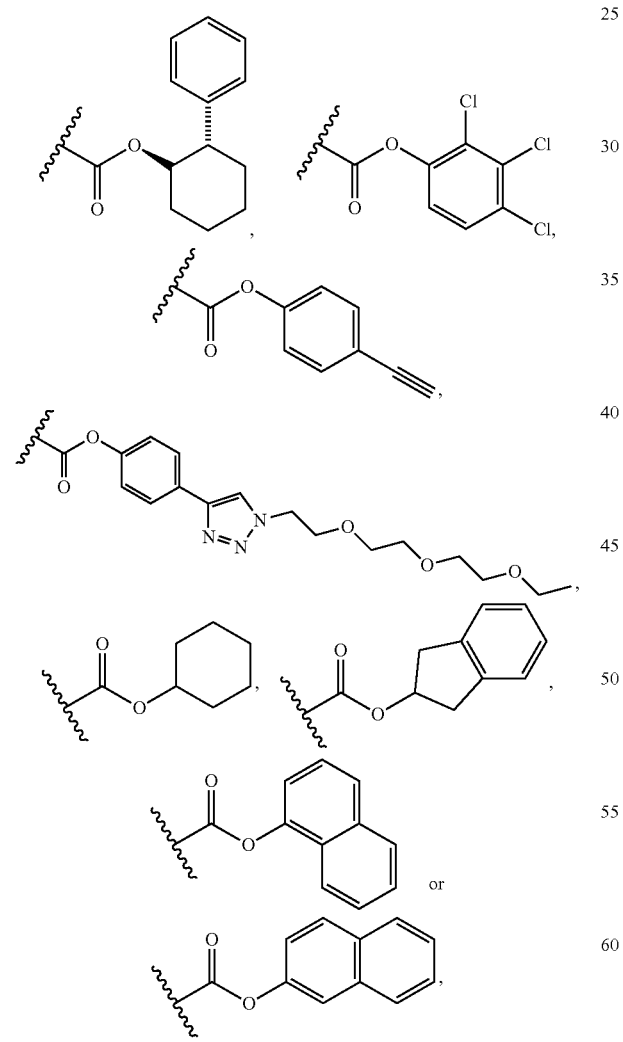
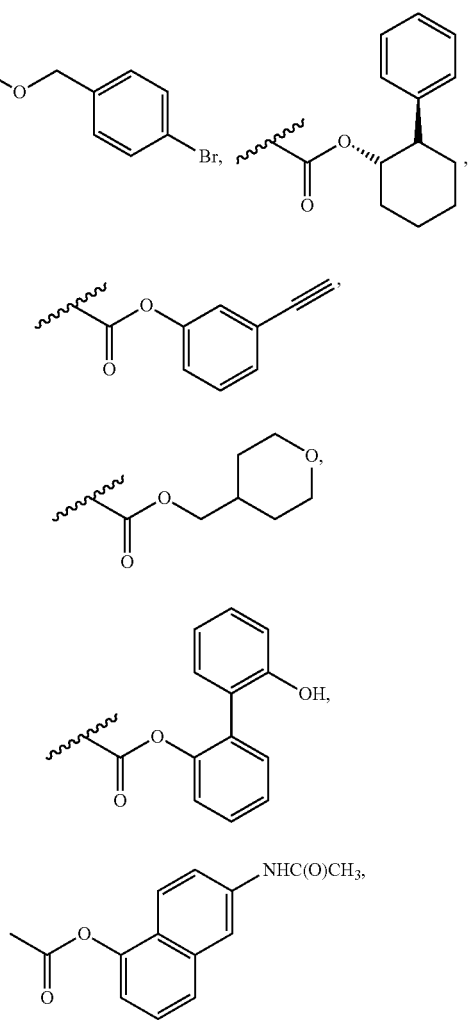
and
the other of $R_1$ or $R_2$ of the compound is —C(═O)OH; or wherein one of $R_1$ or $R_2$ of compound is

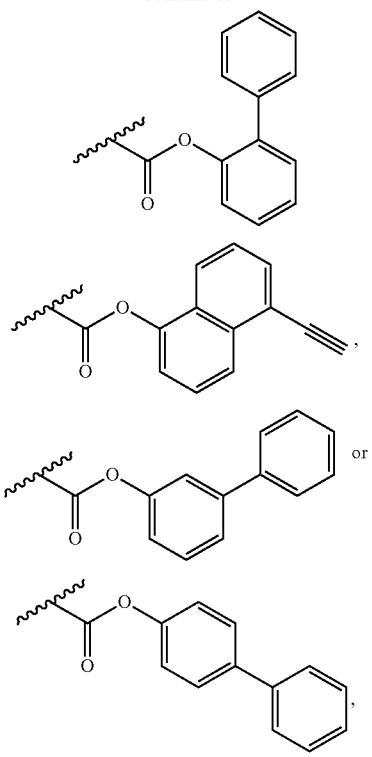

and the other of $R_1$ or $R_2$ of the compound is —C(=O)OH.

14. The method of claim 1, wherein
   (a) $R_3$, $R_4$, $R_5$, $R_6$, $R_7$, $R_8$, $R_9$, $R_{10}$, $R_{11}$ and $R_{12}$ of the compound are each independently, —H, halogen or —OR$_{15}$, wherein $R_{15}$ is —H or $C_{1-10}$ alkyl;
   (b) $R_3$, $R_4$, $R_5$, $R_6$, $R_7$, $R_8$, $R_9$, $R_{10}$, $R_{11}$ and $R_{12}$ of the compound are each independently, —H or —NO$_2$; or
   (c) wherein $R_3$, $R_4$, $R_6$, $R_7$, $R_8$, $R_9$, $R_{11}$ and $R_{12}$ of the compound are each —H; and $R_5$ and $R_{10}$ are each halogen or —OR$_{15}$, wherein $R_{15}$ is —H, $C_{1-10}$ alkyl, $C_{2-10}$ alkenyl, $C_{2-10}$ alkynyl, aryl, or heteroaryl.

15. The method of claim 1, wherein one, two, or four of $R_3$, $R_4$, $R_5$, $R_6$, $R_7$, $R_8$, $R_9$, $R_{10}$, $R_{11}$ and $R_{12}$ of the compound is other than —H.

16. The method of claim 1, wherein the compound is the (S,S) enantiomer or the compound is the (R,R) enantiomer.

17. The method of claim 1, wherein the compound has the following structure:

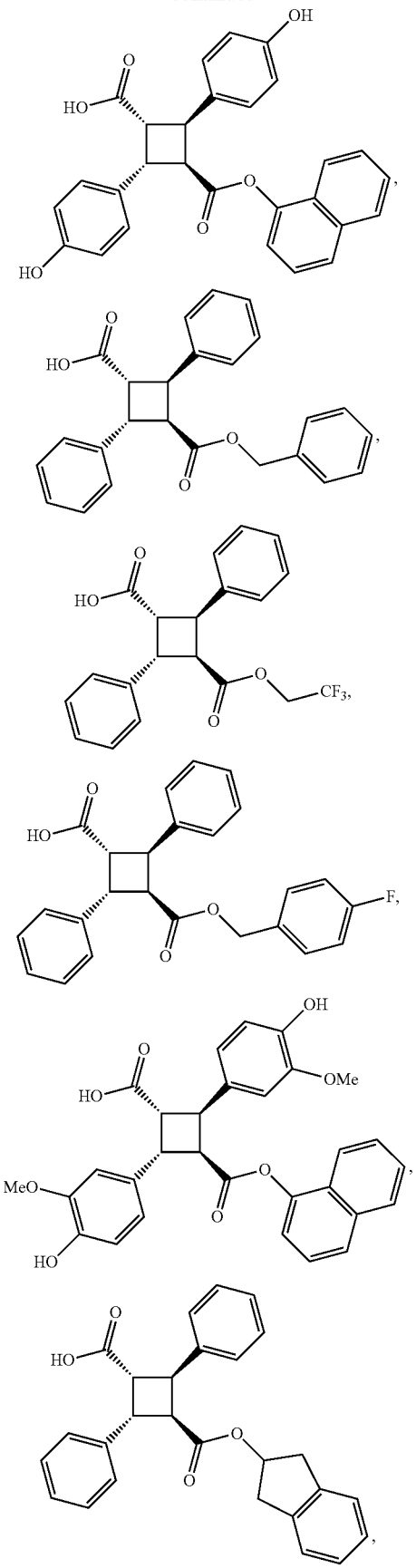

75
-continued
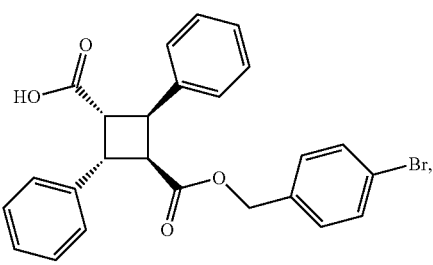
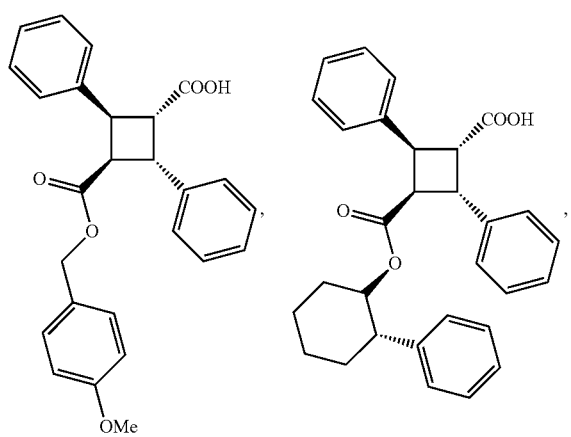
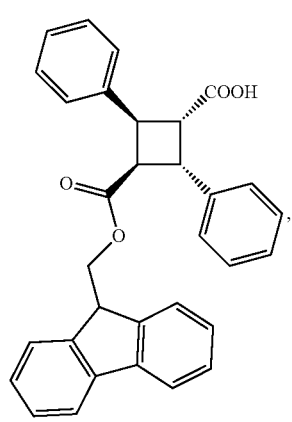
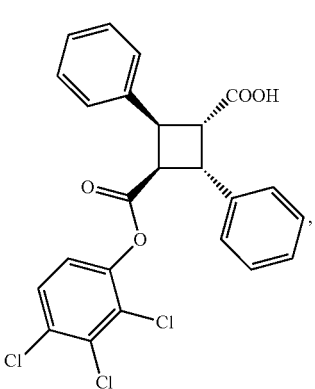
76
-continued
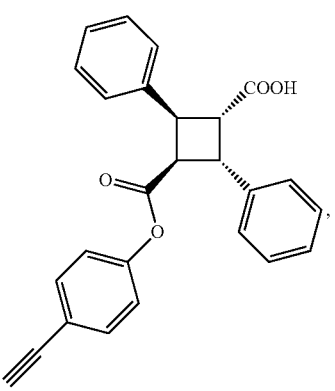
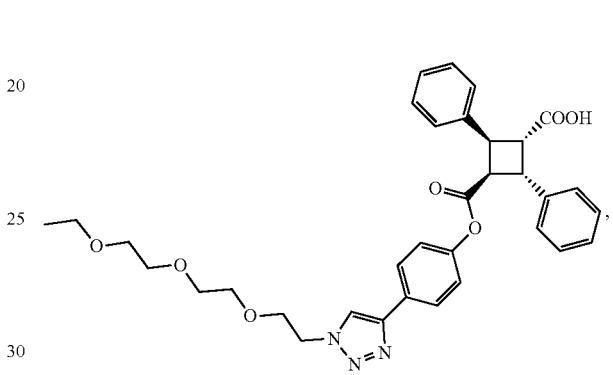
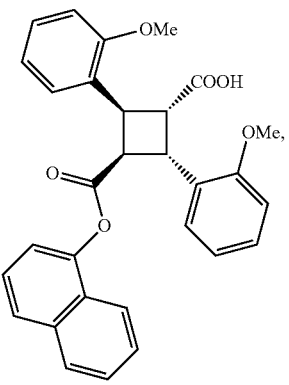
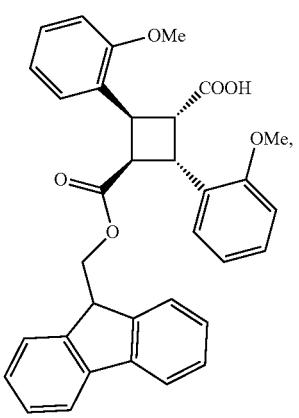

77
-continued
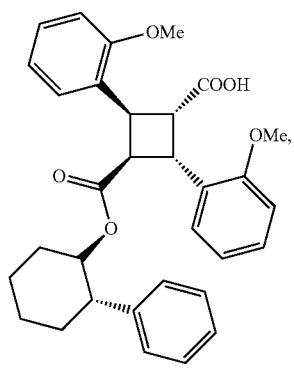
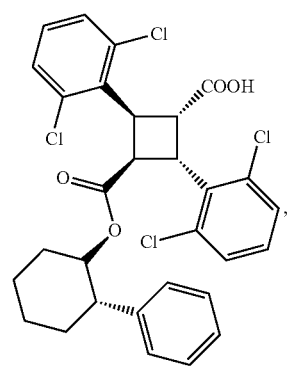
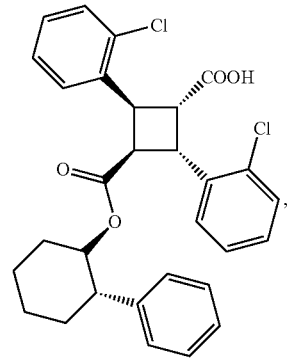
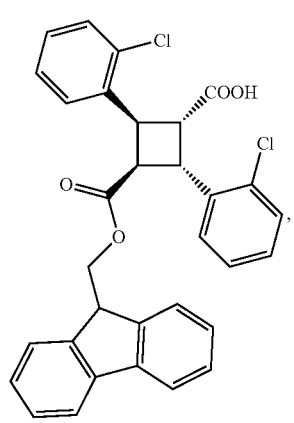
78
-continued
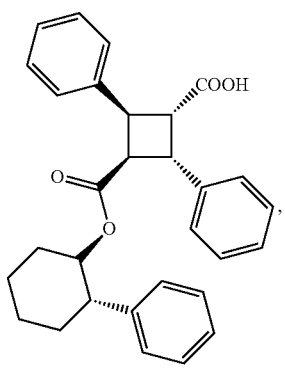
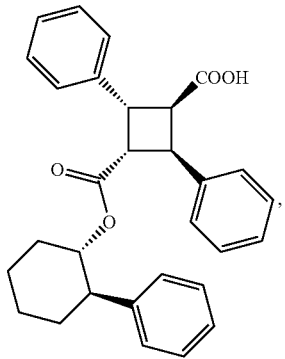
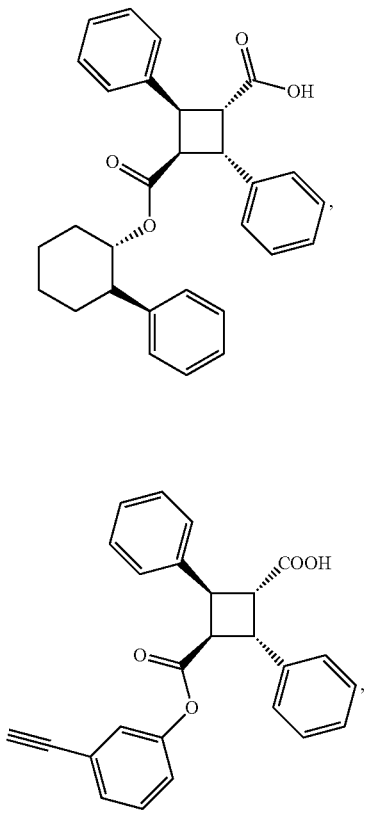

79
-continued
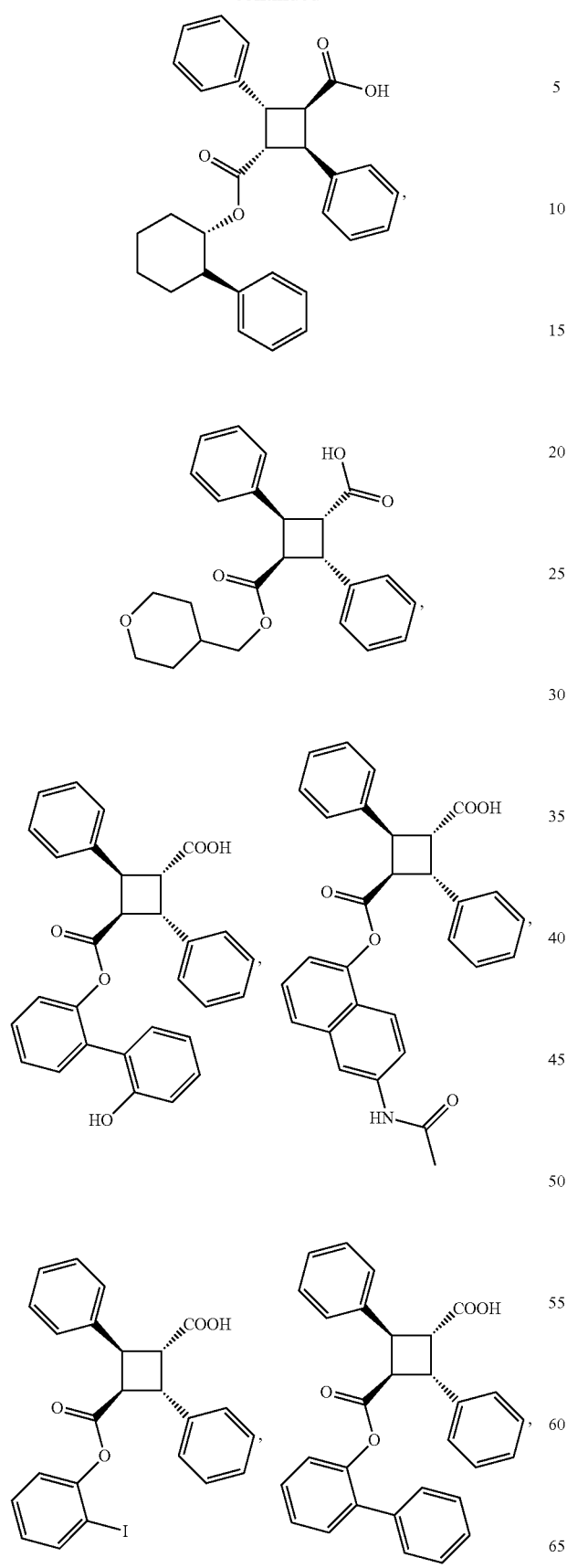
80
-continued
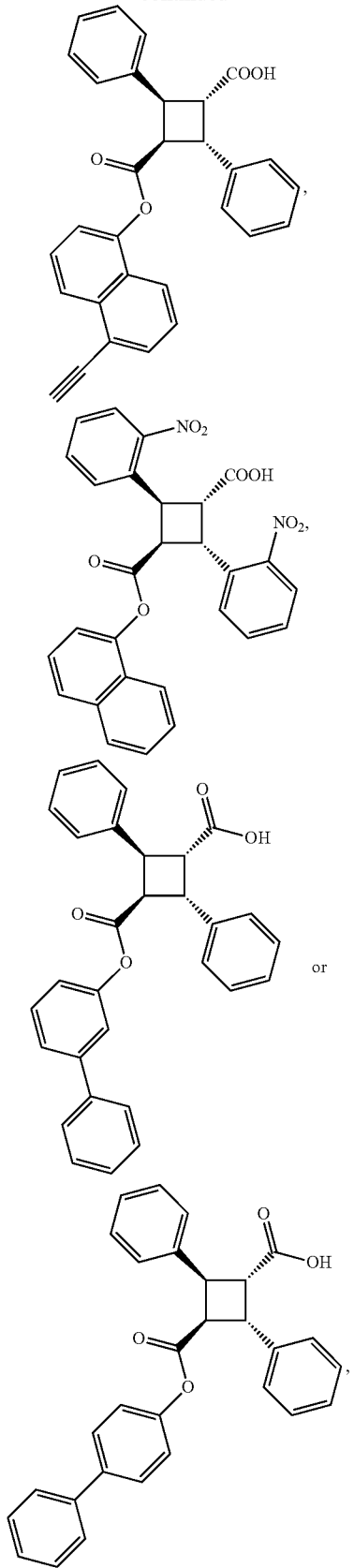
or is an enantiomer or racemate thereof;
or is a pharmaceutically acceptable salt thereof.

18. The method of claim 1, wherein the compound inhibits binding of an FABP ligand to the FABP.

19. The method of claim 18, wherein the FABP ligand is an endocannabinoid ligand.

20. The method of claim 18, wherein the FABP ligand is anandamide (AEA) or 2-arachidonoylglycerol (2-AG).

* * * * *